US012741112B2

(12) United States Patent
Eves et al.

(10) Patent No.: US 12,741,112 B2
(45) Date of Patent: Sep. 22, 2026

(54) PATIENT INTERFACE SYSTEM

(71) Applicant: RESMED PTY LTD, Bella Vista (AU)

(72) Inventors: Matthew Eves, Sydney (AU); Jack Mckenzie Anderson, Sydney (AU); Vanessa Gray, Sydney (AU); Stewart Joseph Wagner, Sydney (AU); Chiew Khuen Wong, Sydney (AU)

(73) Assignee: RESMED PTY LTD, Bella Vista (AU)

( * ) Notice: Subject to any disclaimer, the term of this patent is extended or adjusted under 35 U.S.C. 154(b) by 933 days.

(21) Appl. No.: 17/903,701

(22) Filed: Sep. 6, 2022

(65) Prior Publication Data

US 2023/0073765 A1 Mar. 9, 2023

(30) Foreign Application Priority Data

| | | |
|---|---|---|
| Sep. 6, 2021 | (AU) | 2021902875 |
| Feb. 14, 2022 | (AU) | 2022900315 |
| Feb. 17, 2022 | (AU) | 2022900357 |

(51) Int. Cl.
*A61M 16/06* (2006.01)

(52) U.S. Cl.
CPC .... *A61M 16/0683* (2013.01); *A61M 16/0622* (2014.02)

(58) Field of Classification Search
CPC .......... A61M 16/0605; A61M 16/0616; A61M 16/0622; A61M 16/0683; A61M 16/0816;
(Continued)

(56) References Cited

U.S. PATENT DOCUMENTS 4,782,832 A 11/1988 Trimble et al.
4,944,310 A 7/1990 Sullivan
(Continued)

FOREIGN PATENT DOCUMENTS

WO WO 98/04310 A1 2/1998
WO WO 98/034665 A1 8/1998
(Continued)

OTHER PUBLICATIONS

Extended European Search Report dated Jan. 30, 2023 issued in European Application No. 22194116 (8 pages).
(Continued)

*Primary Examiner* — Annette Dixon
(74) *Attorney, Agent, or Firm* — NIXON & VANDERHYE, PC

(57) ABSTRACT

The present technology relates to a patient interface for delivering breathable gas to a patient. The patient interface may comprise a cushion module including a plenum chamber. The plenum chamber may be substantially flexible. The plenum chamber may be configured so that a superior portion is able to move relative to an inferior portion in order to adjust an orientation of a superior portion of a seal-forming structure relative to an inferior portion of the seal-forming structure. The patient interface may further comprise a positioning and stabilising structure to provide a force to hold the cushion module in a therapeutically effective position on the patient's head. The positioning and stabilising structure may comprise a strap arranged so that the strap overlies the cushion module, the strap passes around the sides of the patient's head inferior to the patient's ears, and the strap overlies a posterior region of the patient's neck.

31 Claims, 37 Drawing Sheets

(58) Field of Classification Search

CPC .......... A61M 16/0866; A61M 16/0875; A61M 16/208; A61M 2202/0085; A61M 2202/0208; A61M 2202/0225; A61M 2207/00; A62B 18/02; A62B 18/084; A62B 18/10; A62B 9/02; A63B 21/0004; A63B 21/00061; A63B 21/00065; A63B 21/0085; A63B 21/4003; A63B 2213/005; A63B 23/18; A63B 69/0028

See application file for complete search history.

(56) References Cited

U.S. PATENT DOCUMENTS 5,687,715 A 11/1997 Landis
6,532,959 B1 3/2003 Berthon-Jones
6,581,594 B1 * 6/2003 Drew ................ A61M 16/0633 128/207.12
7,866,944 B2 1/2011 Kenyon et al.
8,636,479 B2 1/2014 Kenyon et al.
8,638,014 B2 1/2014 Sears et al.
8,733,349 B2 5/2014 Bath et al.
10,300,235 B2 5/2019 Romagnoli et al.
2008/0264422 A1 * 10/2008 Fishman ............... A61M 16/06 128/207.11
2009/0044808 A1 2/2009 Guney et al.
2009/0050156 A1 2/2009 Ng et al.
2010/0000534 A1 1/2010 Kooij et al.
2010/0319700 A1 12/2010 Ng et al.
2012/0080035 A1 4/2012 Guney et al.
2013/0139822 A1 * 6/2013 Gibson ............. A61M 16/0616 128/205.25
2013/0319420 A1 * 12/2013 Danford ................. A62B 18/10 128/206.21
2017/0326320 A1 11/2017 Baigent et al.
2019/0298958 A1 10/2019 O'Connor
2023/0211106 A1 * 7/2023 Tebbutt .............. A61M 16/0611 128/206.21

FOREIGN PATENT DOCUMENTS

WO WO 2000/078381 A1 12/2000
WO WO 2004/071565 8/2004
WO WO 2004/073778 A1 9/2004
WO WO 2005/063328 A1 7/2005
WO WO 2006/074513 A1 7/2006
WO WO 2006/130903 A1 12/2006
WO WO 2009/052560 A1 4/2009
WO WO 2010/135785 A1 12/2010
WO WO 2012/140514 10/2012
WO WO 2012/171072 A1 12/2012
WO 2013/006913 A1 1/2013
WO WO 2013/020167 2/2013
WO WO 2015/020535 2/2015
WO WO 2020/191463 10/2020

OTHER PUBLICATIONS

"*Respiratory Physiology*", by John B. West, Lippincott Williams & Wilkins, 9th edition published 2012 (8 pages).

Extended European Search Report dated Sep. 18, 2025 issued in European Application No. 25164508.1 (9 pages).

* cited by examiner

Copyright 2012 ResMed Limited

Copyright 2012 ResMed Limited

Copyright 2012 ResMed Limited

Copyright 2012 ResMed Limited

Copyright 2012 ResMed Limited

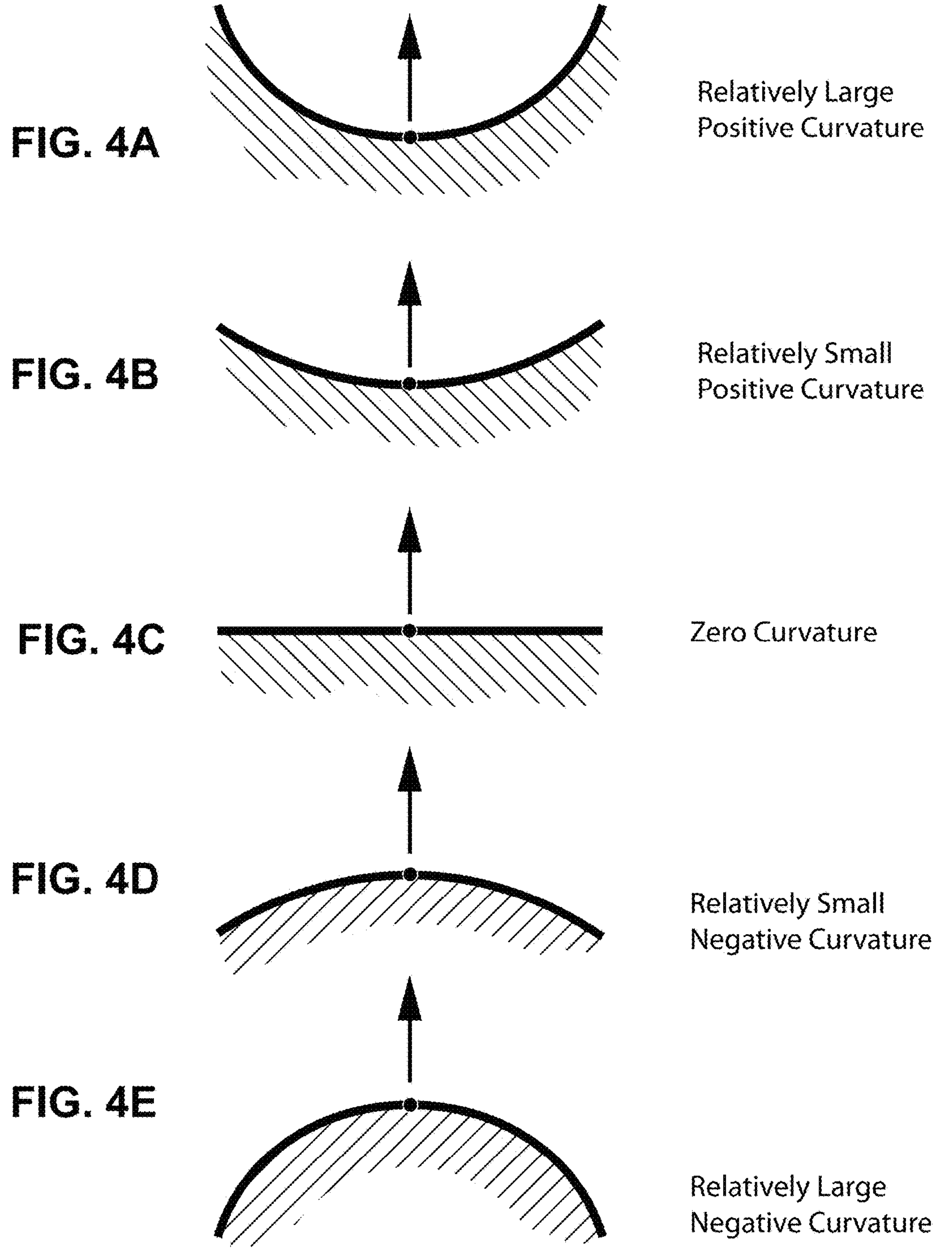
Copyright 2015 ResMed Limited

PATIENT INTERFACE SYSTEM

CROSS-REFERENCE TO RELATED APPLICATION(S)

This application claims priority to Australian Provisional Application No. 2021902875, filed Sep. 6, 2021, Australian Provisional Application No. 2022900315 filed Feb. 14, 2022, and Australian Provisional Application No. 2022900357, filed Feb. 17, 2022, the entire contents of each of which are hereby incorporated by reference.

1 BACKGROUND OF THE TECHNOLOGY

1.1 Field of the Technology

The present technology relates to one or more of the screening, diagnosis, monitoring, treatment, prevention and amelioration of respiratory-related disorders. The present technology also relates to medical devices or apparatus, and their use.

In particular, the present technology relates to patient interfaces for use in respiratory therapy systems for delivering respiratory therapy to patients.

1.2 Description of the Related Art

1.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient CO2 to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

1.2.2 Therapies

Various respiratory therapies, such as Continuous Positive Airway Pressure (CPAP) therapy, Non-invasive ventilation (NIV), Invasive ventilation (IV), and High Flow Therapy (HFT) have been used to treat one or more of the above respiratory disorders.

1.2.2.1 Respiratory Pressure Therapies

Respiratory pressure therapy is the application of a supply of air to an entrance to the airways at a controlled target pressure that is nominally positive with respect to atmosphere throughout the patient's breathing cycle (in contrast to negative pressure therapies such as the tank ventilator or cuirass).

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube or endotracheal tube. In some forms, the comfort and effectiveness of these therapies may be improved.

1.2.2.2 Flow Therapies

Not all respiratory therapies aim to deliver a prescribed therapeutic pressure. Some respiratory therapies aim to deliver a prescribed respiratory volume, by delivering an inspiratory flow rate profile over a targeted duration, possibly superimposed on a positive baseline pressure.

Another form of flow therapy is long-term oxygen therapy (LTOT) or supplemental oxygen therapy. Doctors may prescribe a continuous flow of oxygen enriched air at a specified oxygen concentration (from 21%, the oxygen fraction in ambient air, to 100%) at a specified flow rate (e.g., 1 litre per minute (LPM), 2 LPM, 3 LPM, etc.) to be delivered to the patient's airway.

1.2.3 Respiratory Therapy Systems

These respiratory therapies may be provided by a respiratory therapy system or device. Such systems and devices may also be used to screen, diagnose, or monitor a condition without treating it.

A respiratory therapy system may comprise a Respiratory Pressure Therapy Device (RPT device), an air circuit, a humidifier, a patient interface, an oxygen source, and data management.

1.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance. Feedback from some patients has shown that a patient may be more likely to comply with therapy if a patient interface is designed in a way that it does not look overly 'medical' in appearance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

1.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a single element that surrounds both nares in use. Such single element may be designed to, for example, overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

There is a need for a seal-forming structure to provide an effective seal when used by patients having facial features with a range of different shapes and sizes while being low cost and easy to manufacture, and easy and comfortable for a patient to use.

1.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use. There is a need for a positioning and stabilising structure that is easy and intuitive for a patient to use.

1.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus RPT devices may also act as flow therapy devices. Examples of RPT devices include a CPAP device and a ventilator.

1.2.3.3 Air Circuit

An air circuit is a conduit or a tube constructed and arranged to allow, in use, a flow of air to travel between two components of a respiratory therapy system such as the RPT device and the patient interface. In some cases, there may be separate limbs of the air circuit for inhalation and exhalation. In other cases, a single limb air circuit is used for both inhalation and exhalation.

1.2.3.4 Humidifier

Delivery of a flow of air without humidification may cause drying of airways. The use of a humidifier with an RPT device and the patient interface produces humidified gas that minimizes drying of the nasal mucosa and increases patient airway comfort. In addition, in cooler climates, warm air applied generally to the face area in and about the patient interface is more comfortable than cold air.

1.2.3.5 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focused airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

2 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

An aspect of certain forms of the present technology is to provide apparatus that improve the compliance of patients with respiratory therapy.

One aspect of the present technology comprises a patient interface for use in delivering breathable gas to a patient.

One aspect of the technology comprises a positioning and stabilising structure for a patient interface for use in delivering breathable gas to a patient. The positioning and stabilising structure may be configured to provide a force to hold a cushion module in a therapeutically effective position on the patient's head. The positioning and stabilising structure may comprise a strap configured to be arranged, in use, so that an anterior portion of the strap overlies an anterior surface of the cushion module across the width of the cushion module, the strap passes around the sides of the patient's head inferior to the patient's ears, and a posterior portion of the strap overlies a posterior region of the patient.

In some forms the posterior portion of the strap overlies a posterior region of the patient's neck. In some forms, no part of the positioning and stabilising structure is positioned superior to the patient's ears in use.

One aspect of the technology comprises a positioning and stabilising structure for a patient interface for use in delivering breathable gas to a patient. The positioning and stabilising structure may be configured to provide a force to hold a cushion module in a therapeutically effective position on the patient's head. The positioning and stabilising structure may comprise a strap configured to be arranged, in use, so that an anterior portion of the strap overlies an anterior surface of the cushion module across the width of the cushion module, the strap passes around the sides of the patient's head inferior to the patient's ears, and a posterior portion of the strap overlies a posterior region of the patient's neck. No part of the positioning and stabilising structure may be configured to be positioned superior to the patient's ears in use.

One aspect of the technology comprises a positioning and stabilising structure for a patient interface for use in delivering breathable gas to a patient. The positioning and stabilising structure may be configured to provide a force to hold a cushion module in a therapeutically effective position on the patient's head. The positioning and stabilising structure may comprise a strap configured to be arranged, in use, so that an anterior portion of the strap overlies an anterior surface of the cushion module across the width of the cushion module, the strap passes around the sides of the patient's head inferior to the patient's ears, and a posterior portion of the strap overlies a posterior region of the patient's neck. The strap may be configured to maintain the seal-forming structure in the therapeutically effective position when the cushion module is pressurised to a therapeutic pressure in the absence of other straps.

One aspect of the technology comprises a positioning and stabilising structure for a patient interface for use in delivering breathable gas to a patient. The positioning and stabilising structure may be configured to provide a force to hold the seal-forming structure in a therapeutically effective position on the patient's head. The positioning and stabilising structure may comprise a strap configured to be arranged, in use, so that an anterior portion of the strap overlies an anterior surface of a cushion module across the width of the cushion module, the strap passes around the sides of the patient's head, and a posterior portion of the strap overlies a posterior region of the patient. The positioning and stabilising structure may further comprise one or more support members provided to the anterior portion of the strap. The one or more support members may be rigid or semi-rigid. The one or more support members may be configured to provide or substantially maintain a curvature of the anterior portion when the anterior portion is put under tension. The curvature of the anterior portion may cup around the cushion module.

In one form, the one or more support members may be provided to a side of the anterior portion of the strap which is configured to face towards the patient in use.

In one form, at least one of the one or more support members may be arranged to span across a length of the anterior portion of the strap.

In one form, the one or more support members may comprise a first support member portion and a second support member portion. Each of the first support member portion and second support member portion may be positioned so that, in use, the first support member portion contacts a first lateral side of the cushion module and the second support member portion contacts a second lateral side of the cushion module, the first lateral side of the cushion module being opposite the second lateral side of the cushion module.

One aspect of the technology comprises a positioning and stabilising structure for a patient interface for use in delivering breathable gas to a patient. The positioning and stabilising structure may be configured to provide a force to hold the seal-forming structure in a therapeutically effective position on the patient's head. The positioning and stabilising structure may comprise a strap configured to be arranged, in use, so that an anterior portion of the strap overlies the anterior surface of a cushion module across the width of the cushion module, the strap passes around the sides of the patient's head, and a posterior portion of the strap overlies a posterior region of the patient. The strap may comprise a gas permeable portion. The strap may be configured so that, in use, the gas permeable portion overlies a vent structure so that the continuous flow of gases exhaled by the patient passes through the gas permeable portion.

In one form, the gas permeable portion may be formed from a porous material.

One aspect of the technology comprises a patient interface for use in delivering breathable gas to a patient. The patient interface may comprise a cushion module comprising a chassis portion and a seal-forming structure together forming a plenum chamber pressurisable to a therapeutic pressure of at least 4 $cmH_2O$ above ambient air pressure, the chassis portion having a width in a direction perpendicular to a sagittal plane of the patient when the patient interface is worn in use, and including a plenum chamber inlet port configured to receive a flow of breathable gas at the therapeutic pressure for breathing by the patient, the seal-forming structure being configured to form a seal with a region of the patient's face surrounding an entrance to the patient's airways, said seal-forming structure having an opening therein such that the flow of breathable gas is delivered to the entrance to the patient's airways, the seal-forming structure being configured to maintain said therapeutic pressure in the plenum chamber throughout the patient's respiratory cycle in use. The patient interface may further comprise a vent structure to allow a continuous flow of gases exhaled by the patient from an interior of the plenum chamber to ambient, said vent structure being configured to maintain the therapeutic pressure in the plenum chamber in use. The patient interface may further comprise a positioning and stabilising structure to provide a force to hold the seal-forming structure in a therapeutically effective position on the patient's head. The positioning and stabilising structure may comprise a strap configured to be arranged, in use, so that an anterior portion of the strap overlies an anterior surface of the chassis portion across the width of the chassis portion, the strap passes around the sides of the patient's head inferior to the patient's ears, and a posterior portion of the strap overlies a posterior region of the patient's neck, and wherein no part of the positioning and stabilising structure is configured to be positioned superior to the patient's ears in use.

In one form, the strap may comprise a first end and a second end. The strap may be configured so that the first end is able to be secured to the second end so that the strap forms a loop.

In one form, the strap may comprise a cushion engaging portion between the first end and the second end. The cushion engaging portion may be mid-way between the first end and the second end. The strap may be configured to be arranged, in use, so that the anterior portion of the strap overlying the anterior surface of the chassis portion comprises the cushion engaging portion, and the posterior portion of the strap overlying the posterior region of the patient's neck comprises the first end and the second end.

In one form, the chassis portion may have a height in a direction perpendicular to the Frankfort horizontal plane of the patient when the patient interface is worn in use. A height of the strap in the cushion engaging portion may be such that, in use, the strap covers a majority of the height of the chassis portion.

In one form, the anterior portion of the strap may have formed therein an opening. The opening may be configured to accommodate a conduit for conveying the flow of breathable gas to the plenum chamber inlet port.

In one form, the anterior portion may have a curvature so that, in use, the anterior portion cups around the chassis portion.

In one form, the positioning and stabilising structure may comprise one or more support members provided to the anterior portion of the strap. The one or more support members may be rigid or semi-rigid. The one or more support members may be configured to provide or substantially maintain the curvature of the anterior portion when the anterior portion is put under tension.

In one form, the one or more support members may be provided to a side of the anterior portion configured to face towards the patient in use.

In one form, at least one of the one or more support members may be arranged to span across a length of the anterior portion.

In one form, the one or more support members may comprise a first support member portion and a second support member portion. Each of the first support member portion and second support member portion may be positioned so that, in use, the first support member portion contacts a first lateral side of the chassis portion and the second support member portion contacts a second lateral side of the chassis portion, the first lateral side of the chassis portion being opposite the second lateral side of the chassis portion.

In one form, the strap may comprise a first elastic region in a region of the strap that, in use, is positioned between the anterior portion of the strap and the posterior portion of the strap on a first lateral side of the patient's head, and a second elastic region in a region of the strap that, in use, is positioned between the anterior portion of the strap and the posterior portion of the strap on a second lateral side of the patient's head, the first lateral side of the patient's head being opposite the second lateral side of the patient's head.

In one form, the first elastic region and the second elastic region may be provided along an edge of the strap.

In one form, the edge of the strap may be a superior edge of the strap when the patient interface is in use.

In one form, the chassis portion may be flexible.

In one form, the vent structure may be in the anterior surface of the chassis portion.

In one form, the strap may comprise a gas permeable portion. The strap may be configured so that, in use, the gas permeable portion overlies the vent structure so that the continuous flow of gases exhaled by the patient passes through the gas permeable portion.

In one form, the gas permeable portion may be formed from a porous material.

Another aspect of the present technology provides a patient interface for use in delivering breathable gas to a patient. The patient interface may comprise a cushion module comprising a plenum chamber and a seal-forming structure, the plenum chamber pressurisable to a therapeutic pressure of at least 4 cmH2O above ambient air pressure and including a plenum chamber inlet port configured to receive a flow of breathable gas at the therapeutic pressure for breathing by the patient, the seal-forming structure being configured to form a seal with a region of the patient's face surrounding an entrance to the patient's airways, said seal-forming structure having an opening therein such that the flow of breathable gas is delivered to the entrance to the patient's airways, the seal-forming structure being configured to maintain said therapeutic pressure in the plenum chamber throughout the patient's respiratory cycle in use. The patient interface may further comprise a vent structure to allow a continuous flow of gases exhaled by the patient from an interior of the plenum chamber to ambient, said vent structure being configured to maintain the therapeutic pressure in the plenum chamber in use. The patient interface may further comprise a positioning and stabilising structure to provide a force to hold the seal-forming structure in a therapeutically effective position on the patient's head. The positioning and stabilising structure may comprise: a strap comprising an anterior portion structured to overlie an anterior surface of the cushion module, and a posterior portion structured to overlie a posterior region of the patient's neck, wherein the strap is structured and arranged to maintain the seal-forming structure in the therapeutically effective position when the plenum chamber is pressurised to a therapeutic pressure in the absence of other straps.

In some forms, the strap comprises a first end and a second end, wherein the first end is attachable to the second end so that the strap forms a loop, and the strap comprises a cushion engaging portion mid-way between the first end and the second end.

In some forms, the cushion module has a height in a direction perpendicular to the Frankfort horizontal plane of the patient when the patient interface is worn in use, and a height of the strap in the cushion engaging portion is such that the strap is structured and arranged to cover a majority of the height of the cushion module in use.

In some forms, the anterior portion of the strap has a curvature structured to cup around the cushion module.

In some forms, the positioning and stabilising structure comprises one or more support members provided to the anterior portion of the strap.

In some forms, the one or more support members may be configured to provide or substantially maintain a curvature of the anterior portion when the anterior portion is put under tension.

In some forms, the strap comprises a first elastic region positioned between the anterior portion of the strap and the posterior portion of the strap on a first lateral side of the patient's head in use, and a second elastic region positioned between the anterior portion of the strap and the posterior portion of the strap on a second lateral side of the patient's head in use.

In some forms, the strap comprises a first substantially inextensible portion positioned between the anterior portion of the strap and the posterior portion of the strap on the first lateral side of the patient's head in use, and a second substantially inextensible portion positioned between the anterior portion of the strap and the posterior portion of the strap on the second lateral side of the patient's head in use.

In some forms, the first elastic region and the second elastic region are provided adjacent one of a superior edge and an inferior edge of the strap and the first substantially inextensible portion and the second substantially inextensible portion are provided adjacent the other of the superior edge and the inferior edge of the strap.

One aspect of the technology provides a patient interface for use in delivering breathable gas to a patient. The patient interface may comprise a cushion module comprising a chassis portion and a seal-forming structure together forming a plenum chamber pressurisable to a therapeutic pressure of at least 4 cm$H_2O$ above ambient air pressure the chassis portion being flexible and having a width in a direction perpendicular to a sagittal plane of the patient when the patient interface is worn in use, and including a plenum chamber inlet port configured to receive a flow of breathable gas at the therapeutic pressure for breathing by the patient, the seal-forming structure being configured to form a seal with a region of the patient's face surrounding an entrance to the patient's airways, said seal-forming structure having an opening therein such that the flow of breathable gas is delivered to the entrance to the patient's airways, the seal-forming structure being configured to maintain said therapeutic pressure in the plenum chamber throughout the patient's respiratory cycle in use. The patient interface may further comprise a vent structure to allow a continuous flow of gases exhaled by the patient from an interior of the plenum chamber to ambient, said vent structure being configured to maintain the therapeutic pressure in the plenum chamber in use. The patient interface may further comprise a positioning and stabilising structure to provide a force to hold the seal-forming structure in a therapeutically effective position on the patient's head. The positioning and stabilising structure may comprise a strap configured to be arranged, in use, so that an anterior portion of the strap overlies an anterior surface of the chassis portion across the width of the chassis portion, the strap passes around the sides of the patient's head, and a posterior portion of the strap overlies a posterior region of the patient. The positioning and stabilising structure may further comprise one or more support members provided to the anterior portion of the strap. The one or more support members may be rigid or semi-rigid. The one or more support members may be configured to provide or substantially maintain a curvature of the anterior portion when the anterior portion is put under tension. The curvature of the anterior portion may cup around the cushion module.

In one form, the one or more support members may be provided to a side of the anterior portion configured to face towards the patient in use.

In one form, at least one of the one or more support members may be arranged to span across a length of the anterior portion.

In one form, the one or more support members may comprise a first support member portion and a second support member portion. Each of the first support member portion and second support member portion may be positioned so that, in use, the first support member portion contacts a first lateral side of the chassis portion and the second support member portion contacts a second lateral side of the chassis portion, the first lateral side of the chassis portion being opposite the second lateral side of the chassis portion.

In one form, the strap may be configured, in use, to pass around the sides of the patient's head inferior to the patient's ears with the posterior portion of the strap overlies a posterior region of the patient's neck. No part of the positioning and stabilising structure may be configured to be positioned superior to the patient's ears.

In one form, the strap may comprise a first end and a second end. The strap may be configured so that the first end is able to be secured to the second end so that the strap forms a loop.

In one form, the strap may comprise a cushion engaging portion between the first end and the second end, wherein the strap is configured to be arranged, in use, so that the anterior portion of the strap overlying the anterior surface of the chassis portion comprises the cushion engaging portion, and the posterior portion of the strap overlying the posterior region of the patient's neck comprises the first end and the second end. In some forms, the cushion engaging portion is approximately mid-way between the first end and the second end of the strap.

In some forms, the one or more support members comprises a peripheral support member positioned at or proximate a periphery of the cushion engaging portion of the strap. The peripheral support member may lie at or proximate to and along the periphery of the cushion engaging portion of the strap. The peripheral support member may be configured to maintain a peripheral shape of the cushion engaging portion of the strap. The peripheral support member may be provided at lateral sides of the cushion engaging portion and at a superior side of the cushion engaging portion. The peripheral support member may be located proximate to but spaced from an edge of the cushion engaging portion. The peripheral support member may be encapsulated between a first outer layer and a second outer layer of the strap. The peripheral support member may be immovable relative to the first outer layer and second outer layer. The peripheral support member may be formed from TPU or EVA, by way of example only.

In one form, the chassis portion may have a height in a direction perpendicular to the Frankfort horizontal plane of the patient when the patient interface is worn in use. A height of the strap in the cushion engaging portion may be such that, in use, the strap covers a majority of the height of the chassis portion.

In one form, the anterior portion of the strap may have formed therein an opening, wherein the opening is configured to accommodate a conduit for conveying the flow of breathable gas to the plenum chamber inlet port.

In one form, the strap may comprise a first elastic region in a region of the strap that, in use, is positioned between the anterior portion of the strap and the posterior portion of the strap on a first lateral side of the patient's head, and a second elastic region in a region of the strap that, in use, is positioned between the anterior portion of the strap and the posterior portion of the strap on a second lateral side of the patient's head, the first lateral side of the patient's head being opposite the second lateral side of the patient's head.

In one form, the first elastic region and the second elastic region may be provided along an edge of the strap.

In one form, the edge of the strap may be a superior edge of the strap when the patient interface is in use.

In one form, the vent structure may be in the anterior surface of the cushion module.

In one form, the strap may comprise a gas permeable portion. The strap may be configured so that, in use, the gas permeable portion overlies the vent structure so that the continuous flow of gases exhaled by the patient passes through the gas permeable portion.

In one form, the gas permeable portion may be formed from a porous material.

One aspect of the technology provides a patient interface for use in delivering breathable gas to a patient. The patient interface may comprise a cushion module comprising a chassis portion and a seal-forming structure together forming a plenum chamber pressurisable to a therapeutic pressure of at least 4 $cmH_2O$ above ambient air pressure and including a plenum chamber inlet port configured to receive a flow of breathable gas at the therapeutic pressure for breathing by the patient. The chassis portion may have a width in a direction perpendicular to a sagittal plane of the patient when the patient interface is worn in use. The patient interface may further comprise a vent structure in an anterior surface of the cushion module, the vent structure to allow a continuous flow of gases exhaled by the patient from an interior of the plenum chamber to ambient, said vent structure being configured to maintain the therapeutic pressure in the plenum chamber in use. The seal-forming structure may be configured to form a seal with a region of the patient's face surrounding an entrance to the patient's airways, said seal-forming structure having an opening therein such that the flow of breathable gas is delivered to the entrance to the patient's airways, the seal-forming structure being configured to maintain said therapeutic pressure in the plenum chamber throughout the patient's respiratory cycle in use. The patient interface may further comprise a positioning and stabilising structure to provide a force to hold the seal-forming structure in a therapeutically effective position on the patient's head. The positioning and stabilising structure may comprise a strap configured to be arranged, in use, so that an anterior portion of the strap overlies the anterior surface of the chassis portion across the width of the chassis portion, the strap passes around the sides of the patient's head, and a posterior portion of the strap overlies a posterior region of the patient. The strap may comprise a gas permeable portion. The strap may be configured so that, in use, the gas permeable portion overlies the vent structure so that the continuous flow of gases exhaled by the patient passes through the gas permeable portion.

In one form, the gas permeable portion may be formed from a porous material.

In one form, the strap may comprise a first end and a second end. The strap may be configured so that the first end is able to be secured to the second end so that the strap forms a loop.

In one form, the strap may comprise a cushion engaging portion between the first end and the second end, wherein the strap is configured to be arranged, in use, so that the anterior portion of the strap overlying the anterior surface of the chassis portion comprises the cushion engaging portion, and the posterior portion of the strap overlying the posterior region of the patient's neck comprises the first end and the second end. The cushion engaging portion may be approximately mid-way between the first end and the second end.

In one form, the chassis portion may have a height in a direction perpendicular to the Frankfort horizontal plane of the patient when the patient interface is worn in use. A height of the strap in the cushion engaging portion may be such that, in use, the strap covers a majority of the height of the chassis portion.

In one form, the anterior portion of the strap may have formed therein an opening. The opening may be configured to accommodate a conduit for conveying the flow of breathable gas to the plenum chamber inlet port.

In one form, the anterior portion may have a curvature so that, in use, the anterior portion cups around the chassis portion.

In one form, the positioning and stabilising structure may comprise one or more support members provided to the anterior portion of the strap. The one or more support members may be rigid or semi-rigid. The one or more support members may be configured to provide or substantially maintain the curvature of the anterior portion when the anterior portion is put under tension.

In one form, the one or more support members may be provided to a side of the anterior portion configured to face towards the patient in use.

In one form, at least one of the one or more support members may be arranged to span across a length of the anterior portion.

In one form, the one or more support members may comprise a first support member portion and a second support member portion. Each of the first support member portion and second support member portion may be positioned so that, in use, the first support member portion contacts a first lateral side of the chassis portion and the second support member portion contacts a second lateral side of the chassis portion, the first lateral side of the chassis portion being opposite the second lateral side of the chassis portion.

In one form, the strap may comprise a first elastic region in a region of the strap that, in use, is positioned between the anterior portion of the strap and the posterior portion of the strap on a first lateral side of the patient's head, and a second elastic region in a region of the strap that, in use, is positioned between the anterior portion of the strap and the posterior portion of the strap on a second lateral side of the patient's head, the first lateral side of the patient's head being opposite the second lateral side of the patient's head.

In one form, the first elastic region and the second elastic region may be provided along an edge of the strap.

In one form, the edge of the strap may be a superior edge of the strap when the patient interface is in use.

In one form, the chassis portion may be flexible.

In one form, the vent structure may be in the anterior surface of the cushion module.

One aspect of the technology provides a patient interface for use in delivering breathable gas to a patient. The patient interface may comprise a cushion module comprising a chassis portion and a seal-forming structure together forming a plenum chamber pressurisable to a therapeutic pressure of at least 4 $cmH_2O$ above ambient air pressure and including a plenum chamber inlet port configured to receive a flow of breathable gas at the therapeutic pressure for breathing by the patient, the seal-forming structure being configured to form a seal with a region of the patient's face surrounding an entrance to the patient's airways and comprising a nasal bridge portion configured to form a seal with a nasal bridge region of the patient's face, said seal-forming structure having an opening therein such that the flow of breathable gas is delivered to the entrance to the patient's airways, the seal-forming structure being configured to maintain said therapeutic pressure in the plenum chamber throughout the patient's respiratory cycle in use. The patient interface may further comprise a vent structure to allow a continuous flow of gases exhaled by the patient from an interior of the plenum chamber to ambient, said vent structure being configured to maintain the therapeutic pressure in the plenum chamber in use. The chassis portion may be configured to be substantially flexible and may be configured so that a superior portion of the chassis portion is able to move relative to an inferior portion of the chassis portion in order to adjust an orientation of a superior portion of the seal-forming structure relative to an inferior portion of the seal-forming structure.

In one form, the chassis portion may comprise a flex region having greater flexibility than other regions of the chassis portion, the flex region being configured to enable the superior portion of the chassis portion to move relative to the inferior portion of the cushion module.

In one form, the flex region may extend across substantially the width of the chassis portion. The width of the chassis portion may be in a direction perpendicular to a sagittal plane of the patient when the patient interface is worn in use.

In one form, the flex region may be located in a middle region with respect to a height of the chassis portion. The height of the chassis portion may be in a direction perpendicular to the Frankfort horizontal plane of the patient when the patient interface is worn in use.

In one form, the flex region may be lens-shaped.

In one form, material forming the flex region may have a lesser thickness than material forming the chassis portion in other regions of the chassis portion.

In one form, the patient interface may be configured so that the orientation of the superior portion of the seal-forming structure relative to the inferior portion of the seal-forming structure adjusts when the patient interface is donned by the patient in use to cause the flex region to flex.

In one form, the chassis portion may be formed from silicone.

In one form, the chassis portion may be formed from a fabric.

In one form, the fabric forming the chassis portion may be a first fabric. The flex region may comprise a slit in the first fabric. The chassis portion may comprise a gusset spanning the slit, the gusset being formed from a second fabric.

In one form, the seal-forming structure may be formed from silicone. In another form, the seal-forming structure may be formed from foam.

In one form, the cushion module may comprise a one-piece body comprising the plenum chamber and the seal-forming structure.

In one form, the seal-forming structure may be configured to form a seal with a region of the patient's face surrounding the patient's nares and mouth.

In one form, the plenum chamber inlet port may be configured to receive a conduit for conveying the flow of breathable gas to the plenum chamber with an interference fit.

In one form, the patient interface may further comprise a positioning and stabilising structure to provide a force to hold the seal-forming structure in a therapeutically effective position on the patient's head.

In one form, the positioning and stabilising structure may comprise a strap configured to be arranged, in use, so that an anterior portion of the strap overlies an anterior surface of the chassis portion across the width of the chassis portion, the strap passes around the sides of the patient's head inferior to the patient's ears, and a posterior portion of the strap overlies a posterior region of the patient's neck. No part of the positioning and stabilising structure may be configured to be positioned superior to the patient's ears in use.

In one form, the strap may comprise a first end and a second end. The strap may be configured so that the first end is able to be secured to the second end so that the strap forms a loop.

In one form, the strap may comprise a cushion engaging portion between the first end and the second end, wherein the strap is configured to be arranged, in use, so that the anterior portion of the strap overlying the anterior surface of the chassis portion comprises the cushion engaging portion, and the posterior portion of the strap overlying the posterior region of the patient's neck comprises the first end and the second end. The cushion engaging portion may be approximately mid-way between the first end and the second end of the strap.

In one form, the chassis portion may have a height in a direction perpendicular to the Frankfort horizontal plane of the patient when the patient interface is worn in use. A height of the strap in the cushion engaging portion may be such that, in use, the strap covers a majority of the height of the chassis portion.

In one form, the anterior portion of the strap may have formed therein an opening. The opening may be configured to accommodate a conduit for conveying the flow of breathable gas to the plenum chamber inlet port.

In one form, the anterior portion may have a curvature so that, in use, the anterior portion cups around the chassis portion.

In one form, the positioning and stabilising structure may comprise one or more support members provided to the anterior portion of the strap. The one or more support members may be rigid or semi-rigid. The one or more support members may be configured to provide or substantially maintain the curvature of the anterior portion when the anterior portion is put under tension.

In one form, the one or more support members may be provided to a side of the anterior portion configured to face towards the patient in use.

In one form, at least one of the one or more support members may be arranged to span across a length of the anterior portion.

In one form, the one or more support members may comprise a first support member portion and a second support member portion. Each of the first support member portion and second support member portion may be positioned so that, in use, the first support member portion contacts a first lateral side of the chassis portion and the second support member portion contacts a second lateral side of the chassis portion, the first lateral side of the chassis portion being opposite the second lateral side of the chassis portion.

In one form, the strap may comprise a first elastic region in a region of the strap that, in use, is positioned between the anterior portion of the strap and the posterior portion of the strap on a first lateral side of the patient's head, and a second elastic region in a region of the strap that, in use, is positioned between the anterior portion of the strap and the posterior portion of the strap on a second lateral side of the patient's head, the first lateral side of the patient's head being opposite the second lateral side of the patient's head.

In one form, the first elastic region and the second elastic region may be provided along an edge of the strap.

In one form, the edge of the strap may be a superior edge of the strap when the patient interface is in use.

In one form, the vent structure may be in the anterior surface of the chassis portion.

In one form, the strap may comprise a gas permeable portion. The strap may be configured so that, in use, the gas permeable portion overlies the vent structure so that the continuous flow of gases exhaled by the patient passes through the gas permeable portion.

In one form, the gas permeable portion may be formed from a porous material.

One aspect of the technology comprises a positioning and stabilising structure for a patient interface for use in delivering breathable gas to a patient. The positioning and stabilising structure may be configured to provide a force to hold the seal-forming structure in a therapeutically effective position on the patient's head. The positioning and stabilising structure may comprise a strap configured to be arranged, in use, so that an anterior portion of the strap overlies an anterior surface of a cushion module across the width of the cushion module, the strap passes around the sides of the patient's head, and a posterior portion of the strap overlies a posterior region of the patient. The strap may comprise a first outer layer configured to face towards the patient's face in use, a second outer layer configured to face away from the patient's face in use, and one or more support members provided to the anterior portion of the strap between the first outer layer and the second outer layer.

One aspect of the technology provides a patient interface for use in delivering breathable gas to a patient. The patient interface may comprise a cushion module comprising a chassis portion and a seal-forming structure together forming a plenum chamber pressurisable to a therapeutic pressure of at least 4 $cmH_2O$ above ambient air pressure and including a plenum chamber inlet port configured to receive a flow of breathable gas at the therapeutic pressure for breathing by the patient, the seal-forming structure being configured to form a seal with a region of the patient's face surrounding an entrance to the patient's airways, said seal-forming structure having an opening therein such that the flow of breathable gas is delivered to the entrance to the patient's airways, the seal-forming structure being configured to maintain said therapeutic pressure in the plenum chamber throughout the patient's respiratory cycle in use. The chassis portion may have a width in a direction perpendicular to a sagittal plane of the patient when the patient interface is worn in use. The patient interface may further comprise a vent structure to allow a continuous flow of gases exhaled by the patient from an interior of the plenum chamber to ambient, said vent structure being configured to maintain the therapeutic pressure in the plenum chamber in use. The patient interface may further comprise a positioning and stabilising structure to provide a force to hold the seal-forming structure in a therapeutically effective position on the patient's head. The positioning and stabilising structure may comprise a strap configured to be arranged, in use, so that an anterior portion of the strap overlies an anterior surface of the chassis portion across the width of the chassis portion, the strap passes around the sides of the patient's head, and a posterior portion of the strap overlies a posterior region of the patient. The strap may comprise a first outer layer configured to face towards the patient's face in use, a second outer layer configured to face away from the patient's face in use, and one or more support members provided to the anterior portion of the strap between the first outer layer and the second outer layer.

In some forms, the posterior portion of the strap overlies a posterior region of the patient's neck. In some forms, no portion of the positioning and stabilising structure is positioned superior to the patient's ears.

In some forms, the first and second outer layers are elastically extendable. The first and second outer layers may be formed from foam and/or textile materials. Each of the first and second outer layers may comprise a laminate. Each of the first and second outer layers may comprise a foam inner layer and a textile outer layer. The first and second outer layers may form the entire surface area of the strap.

The one or more support members may be rigid or semi-rigid. The one or more support members may be configured to provide or substantially maintain a curvature of the anterior portion when the anterior portion is put under tension. The support members may be thermoformed.

In one form, the strap may comprise a first end and a second end. The strap may be configured so that the first end is able to be secured to the second end so that the strap forms a loop.

In one form, the strap may comprise a cushion engaging portion between the first end and the second end, wherein the strap is configured to be arranged, in use, so that the anterior portion of the strap overlying the anterior surface of the chassis portion comprises the cushion engaging portion, and the posterior portion of the strap overlying the posterior region of the patient's neck comprises the first end and the second end. The cushion engaging portion may be approximately mid-way between the first end and the second end of the strap.

In some forms, the one or more support members are positioned within the cushion engaging portion. The one or more support members may occupy a majority of the area within the cushion engaging portion. The one or more support members may comprise a first support member portion provided to a superior portion of the cushion engaging portion and a second support member portion provided to an inferior portion of the cushion engaging portion. The first support member portion and the second support member portion may be formed separately.

In some forms, the strap may comprise one or more connection holes to facilitate connection of the strap to the cushion module. The connection holes may be provided through the one or more support members. The cushion module may comprise protrusions configured to be received in the connection holes to attach the strap to the cushion module.

In some forms, the one or more support members comprises a peripheral support member positioned at or proximate a periphery of the cushion engaging portion of the strap. The peripheral support member may lie at or proximate to and along the periphery of the cushion engaging portion of the strap. The peripheral support member may be configured to maintain a peripheral shape of the cushion engaging portion of the strap. The peripheral support member may be provided at lateral sides of the cushion engaging portion and at a superior side of the cushion engaging portion. The peripheral support member may be located proximate to but spaced from an edge of the cushion engaging portion. The peripheral support member may be encapsulated between the first outer layer and the second outer layer of the strap. The peripheral support member may be immovable relative to the first outer layer and second outer layer. The peripheral support member may be formed from TPU or EVA.

In some forms, the strap comprises one or more portions having a lesser extensibility than one or more other portions of the strap. The strap may comprise one or more portions that are substantially inextensible.

In some forms, the strap comprises a pair of substantially inextensible portions located on respective lateral sides of the cushion engaging portion. The strap may comprise a first substantially inextensible portion located between the cushion engaging portion and the first end of the strap and a second substantially inextensible portion located between the cushion engaging portion and the second end of the strap. Each substantially inextensible portion may extend laterally from adjacent the cushion engaging portion to the respective one of the first end of the strap and second end of the strap. The substantially inextensible portions may be located along superior edges of the strap on either lateral side of the cushion engaging portion. The strap may comprise a webbing in each substantially inextensible portion.

In some forms, the strap comprises a pair of low extensibility portions located on respective lateral sides of the strap, the low extensibility portions being more extendable than the substantially inextensible portions but less extendable than the elastic regions. Each low extensibility portion may extend from a respective end of the strap along the strap approximately halfway to a respective lateral edge of the cushion engaging portion. The low extensibility portions may each occupy half of the width of the strap proximate the ends of the strap, and the substantially inextensible portions may each occupy the other half of the width of the strap proximate the ends of the strap. The strap may comprise a webbing in each low extensibility portion.

In some forms, the strap comprises a pair of elastic regions on respective lateral sides of the cushion engaging portion. The elastic regions may each be located proximate an inferior edge of the strap. The first and second outer layers may be elastic and the elastic regions may be formed by the outer layers. The strap may comprise recesses formed in the substantially inextensible portions at the locations of the elastic regions such that only the first and second outer layers define the strap at the elastic regions.

In some examples, the strap may be formed by thermoforming. In some forms, the first outer layer, the second outer layer and the one or more support members are thermoformed together. The support members, substantially inextensible portions and/or the low extensibility portions of the strap may be encapsulated within the first outer layer and second outer layer of the strap.

One aspect of the technology comprises a positioning and stabilising structure for a patient interface for use in delivering breathable gas to a patient. The positioning and stabilising structure may be configured to provide a force to hold a cushion module in a therapeutically effective position on the patient's head. The positioning and stabilising structure may comprise a strap configured to be arranged, in use, so that an anterior portion of the strap overlies an anterior surface of the cushion module across the width of the cushion module, the strap passes around the sides of the patient's head inferior to the patient's ears, and a posterior portion of the strap overlies a posterior region of the patient. The strap may comprise a first elastic region positioned between the anterior portion of the strap and the posterior portion of the strap on a first lateral side of the patient's head in use, and a second elastic region positioned between the anterior portion of the strap and the posterior portion of the strap on a second lateral side of the patient's head in use. The strap may further comprise a first substantially inextensible portion positioned between the anterior portion of the strap and the posterior portion of the strap on the first lateral side of the patient's head in use, and a second substantially inextensible portion positioned between the anterior portion of the strap and the posterior portion of the strap on the second lateral side of the patient's head in use. The first elastic region and the second elastic region may be provided adjacent one of a superior edge and an inferior edge of the strap and the first substantially inextensible portion and the second substantially inextensible portion may be provided adjacent the other of the superior edge and the inferior edge of the strap.

In one form, the first substantially inextensible portion and the second substantially inextensible portion are provided adjacent the superior edge of the strap and the first elastic region and the second elastic region are provided adjacent the inferior edge of the strap.

In one form, the anterior portion of the strap comprises a cushion engaging portion configured to engage the cushion module, and the strap comprises a first end and a second end, the strap being configured so that the first end is able to be secured to the second end so that the strap forms a loop.

In one form, each substantially inextensible portion may extend laterally from adjacent the cushion engaging portion to a respective one of the first end of the strap and the second end of the strap.

In one form, the strap comprises webbing in each substantially inextensible portion.

In one form, the strap comprises a pair of low extensibility portions located on respective lateral sides of the strap, the low extensibility portions being more extendable than the substantially inextensible portions but less extendable than the elastic regions.

In one form, each low extensibility portion extends from a respective one of the first end and the second end of the strap along the strap approximately halfway to a respective lateral edge of the cushion engaging portion.

In one form, the low extensibility portions each occupy half of a width of the strap proximate the ends of the strap, and the substantially inextensible portions may occupy the other half of the width of the strap proximate the ends of the strap, the width of the strap being measured in a direction substantially parallel to a superior-inferior axis of the patient's head.

In one form, the strap comprises webbing in each low extensibility portion.

In one form, the strap comprises a first outer layer configured to face towards the patient's face in use and a second outer layer configured to face away from the patient's face in use.

In some forms, the first and second outer layers are elastically extendable.

In one form, the first and second outer layers are formed from foam and/or textile materials.

In one form, each of the first and second outer layers comprises a laminate.

In one form, each of the first and second outer layers comprises a foam inner layer and a textile outer layer.

In one form, the first and second outer layers form the entire surface area of the strap.

In one form, the first and second outer layers are elastic and the first and second elastic regions are formed by the outer layers.

In one form, the strap comprises recesses formed in the substantially inextensible portions at the locations of the elastic regions such that only the first and second outer layers define the strap at the elastic regions.

In some forms the positioning and stabilising structure further comprises one or more support members provided to the anterior portion of the strap. The one or more support members may be rigid or semi-rigid. The one or more support members may be configured to provide or substantially maintain a curvature of the anterior portion when the anterior portion is put under tension.

In some forms, the one or more support members are between the first outer layer and the second outer layer.

In one form, the support members are thermoformed.

In some forms, the strap comprises a plurality of layers thermoformed together.

In one form, the support members, substantially inextensible portions and/or the low extensibility portions of the strap are encapsulated within the first and second outer layers of the strap.

An aspect of certain forms of the present technology is a medical device that is easy to use, e.g. by a person who does not have medical training, by a person who has limited dexterity, vision or by a person with limited experience in using this type of medical device.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

3 BRIEF DESCRIPTION OF THE DRAWINGS

The present technology is illustrated by way of example, and not by way of limitation, in the figures of the accompanying drawings, in which like reference numerals refer to similar elements including:

3.1 Respiratory Therapy Systems

FIG. 1 shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

3.2 Respiratory System and Facial Anatomy

Figure 1:
Figure 2A:
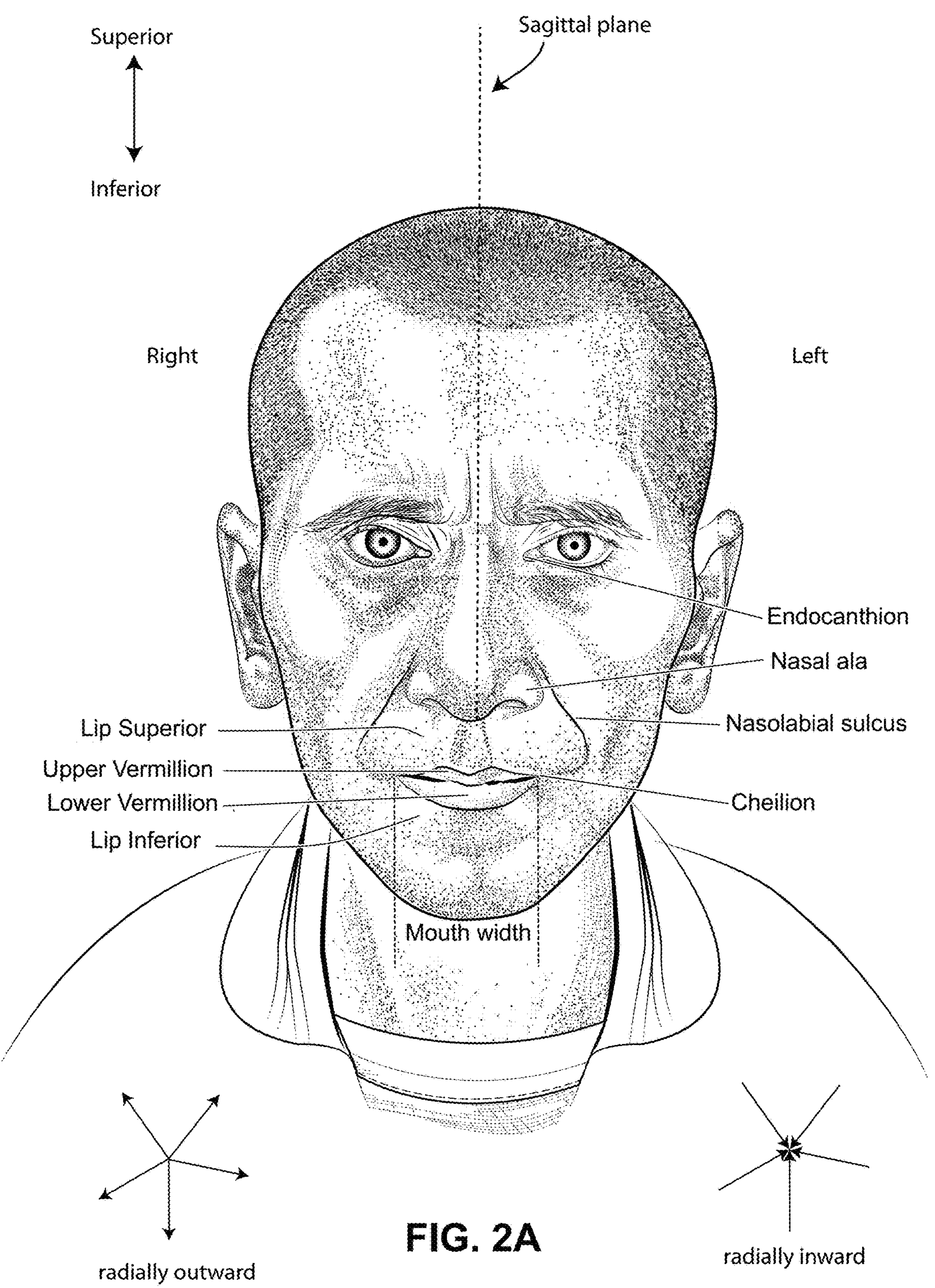
FIG. 2A is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2B:
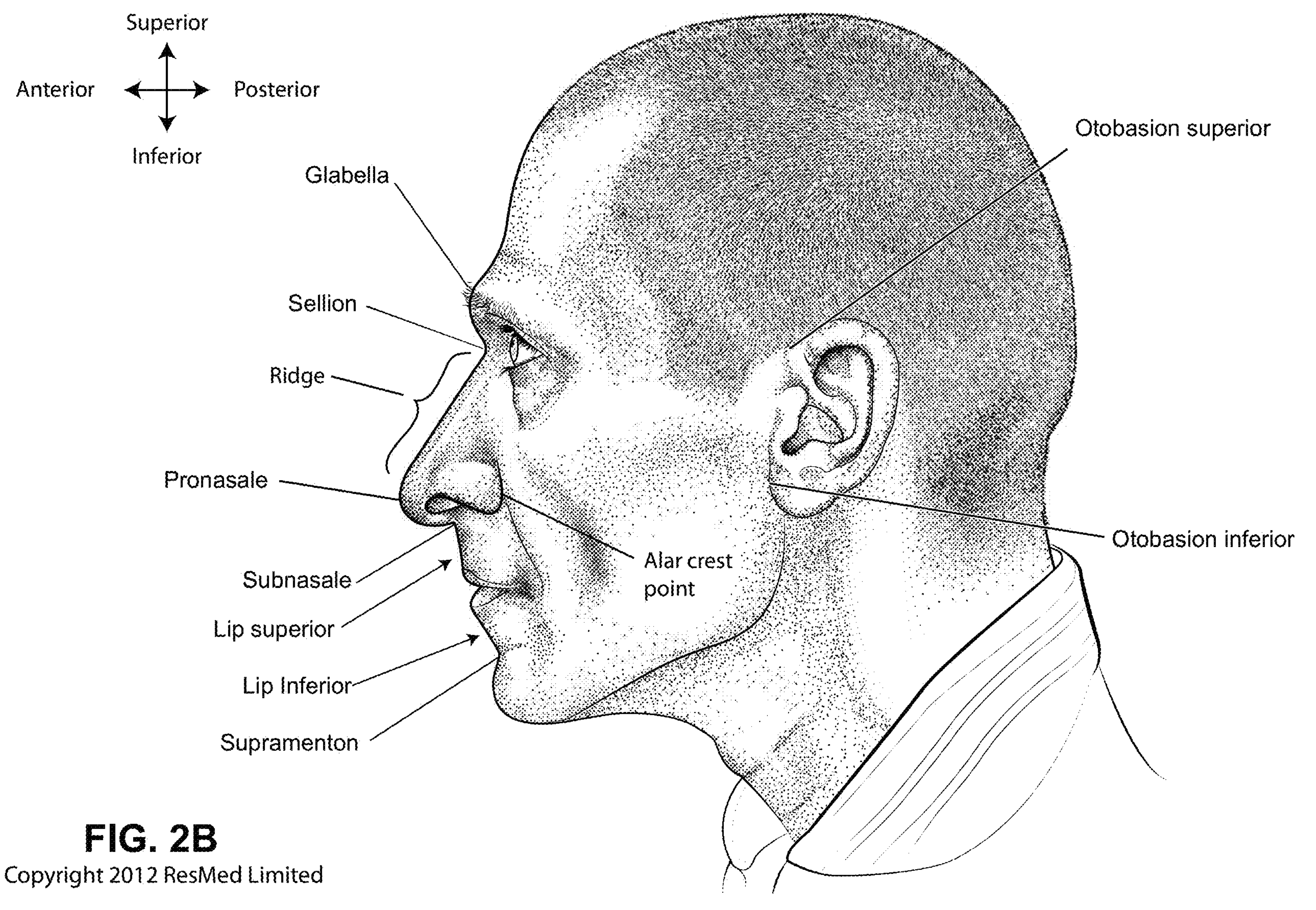
FIG. 2B is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2C:
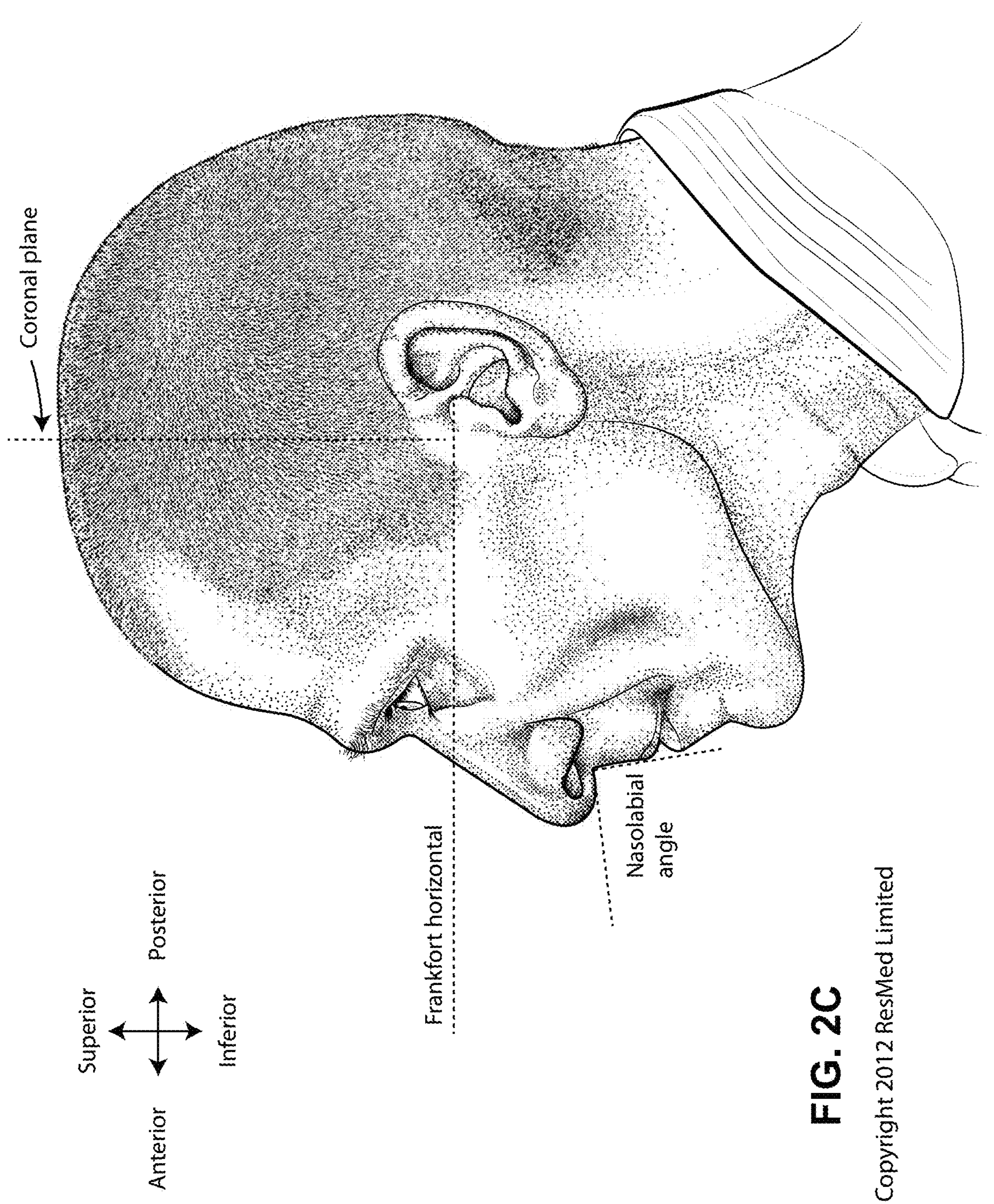

FIG. 2C is a further side view of a head. The approximate locations of the Frankfort horizontal and nasolabial angle are indicated. The coronal plane is also indicated.

Figure 2D:
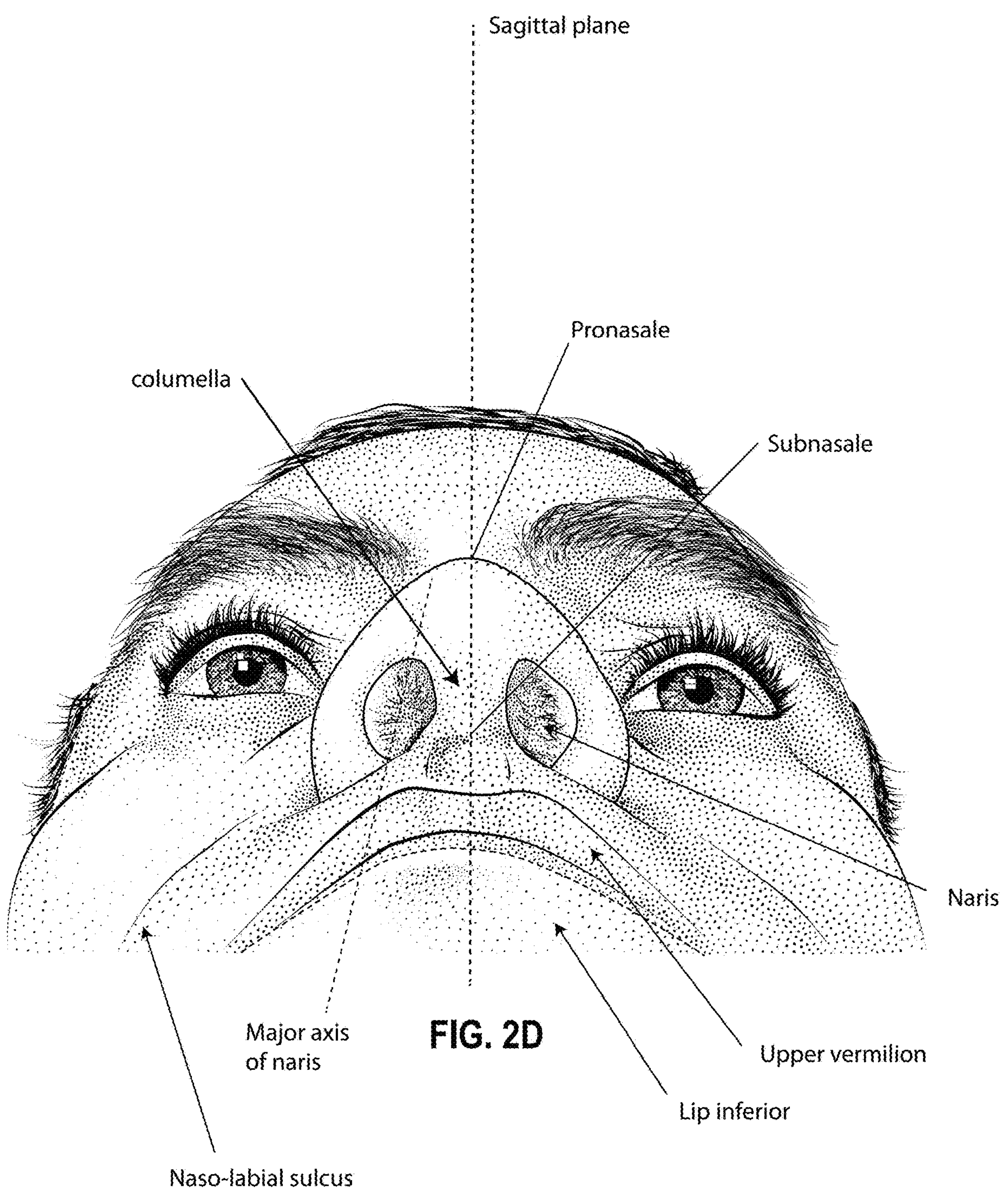

FIG. 2D shows a base view of a nose with several features identified including naso-labial sulcus, lip inferior, upper Vermilion, naris, subnasale, columella, pronasale, the major axis of a naris and the midsagittal plane.

Figures 2E, 2F:
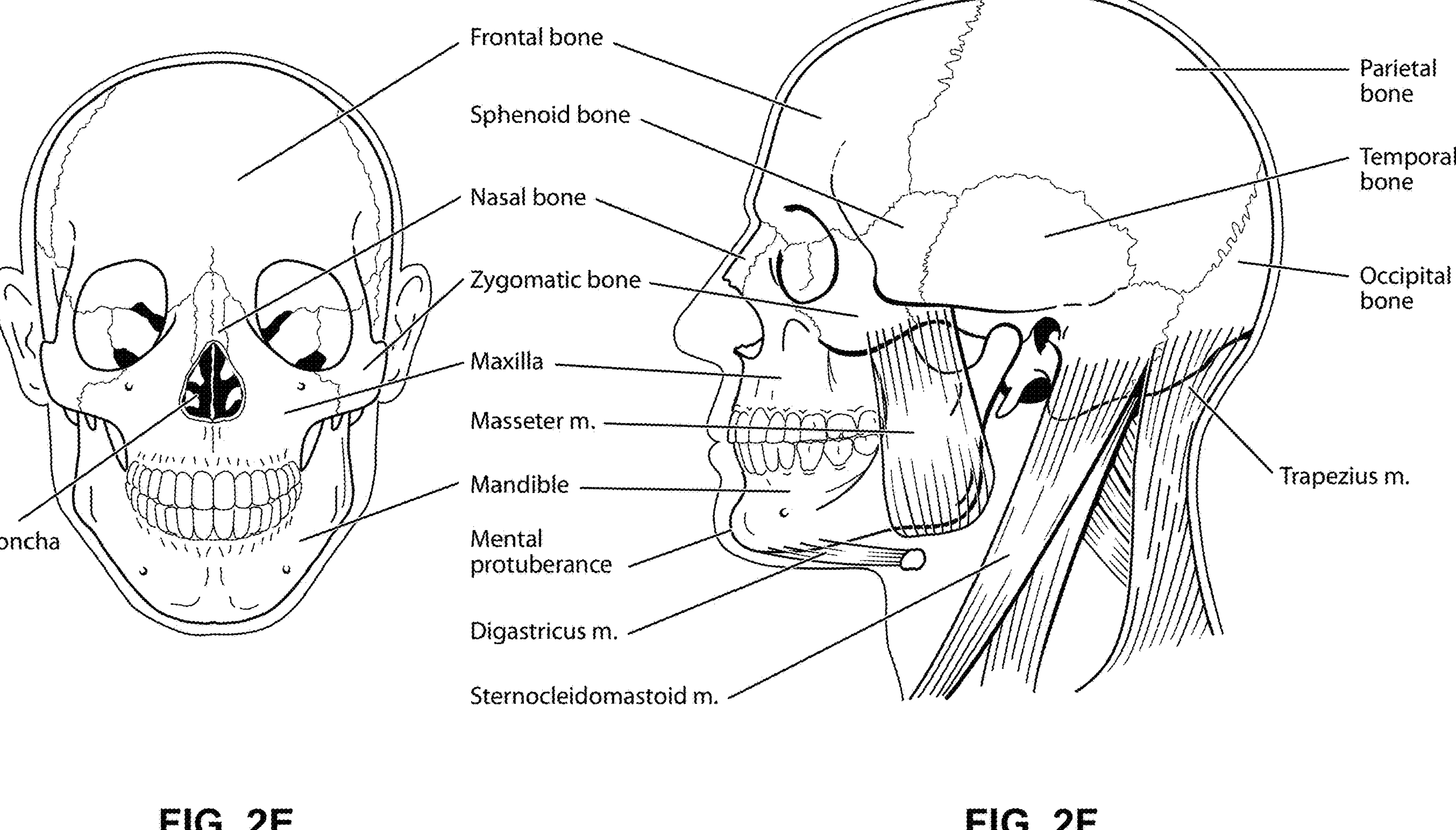

FIG. 2E shows a front view of the bones of a skull including the frontal, nasal and zygomatic bones. Nasal concha are indicated, as are the maxilla, and mandible.

FIG. 2F shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

3.3 Patient Interface

Figure 3:
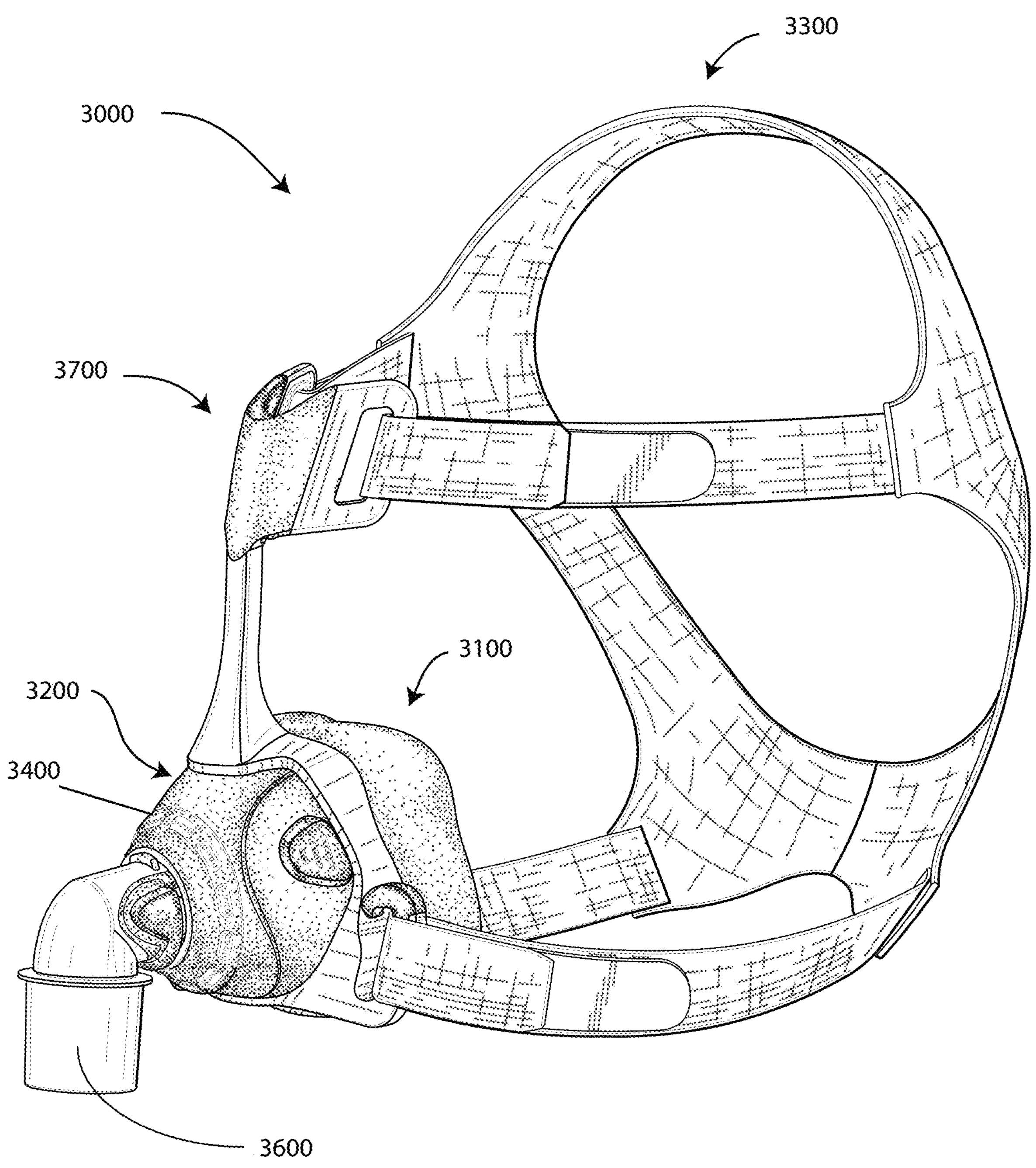

FIG. 3 shows a patient interface in the form of a nasal mask in accordance with one form of the present technology.

FIG. 4A shows a schematic of a cross-section through a structure at a point. An outward normal at the point is indicated. The curvature at the point has a positive sign, and a relatively large magnitude when compared to the magnitude of the curvature shown in FIG. 4B.

FIG. 4B shows a schematic of a cross-section through a structure at a point. An outward normal at the point is indicated. The curvature at the point has a positive sign, and a relatively small magnitude when compared to the magnitude of the curvature shown in FIG. 4A.

FIG. 4C shows a schematic of a cross-section through a structure at a point. An outward normal at the point is indicated. The curvature at the point has a value of zero.

FIG. 4D shows a schematic of a cross-section through a structure at a point. An outward normal at the point is indicated. The curvature at the point has a negative sign, and a relatively small magnitude when compared to the magnitude of the curvature shown in FIG. 4E.

FIG. 4E shows a schematic of a cross-section through a structure at a point. An outward normal at the point is indicated. The curvature at the point has a negative sign, and a relatively large magnitude when compared to the magnitude of the curvature shown in FIG. 4D.

3.4 Humidifier

Figure 5A:
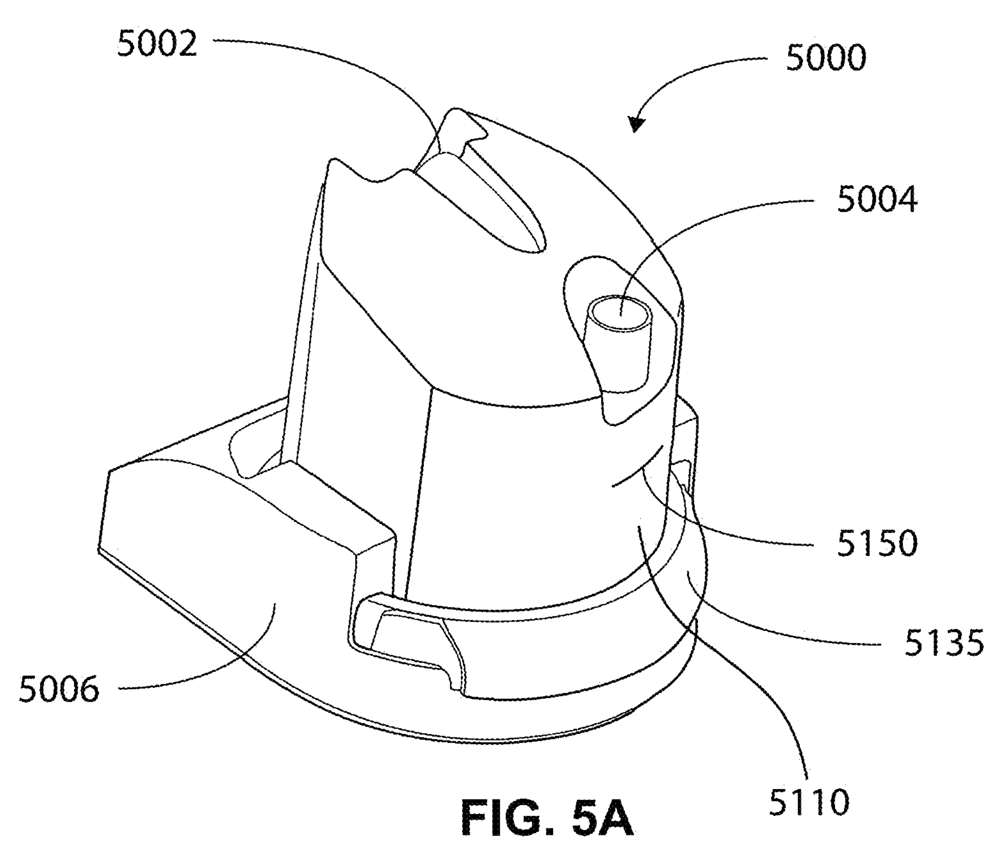

FIG. 5A shows an isometric view of a humidifier in accordance with one form of the present technology.

Figure 5B:
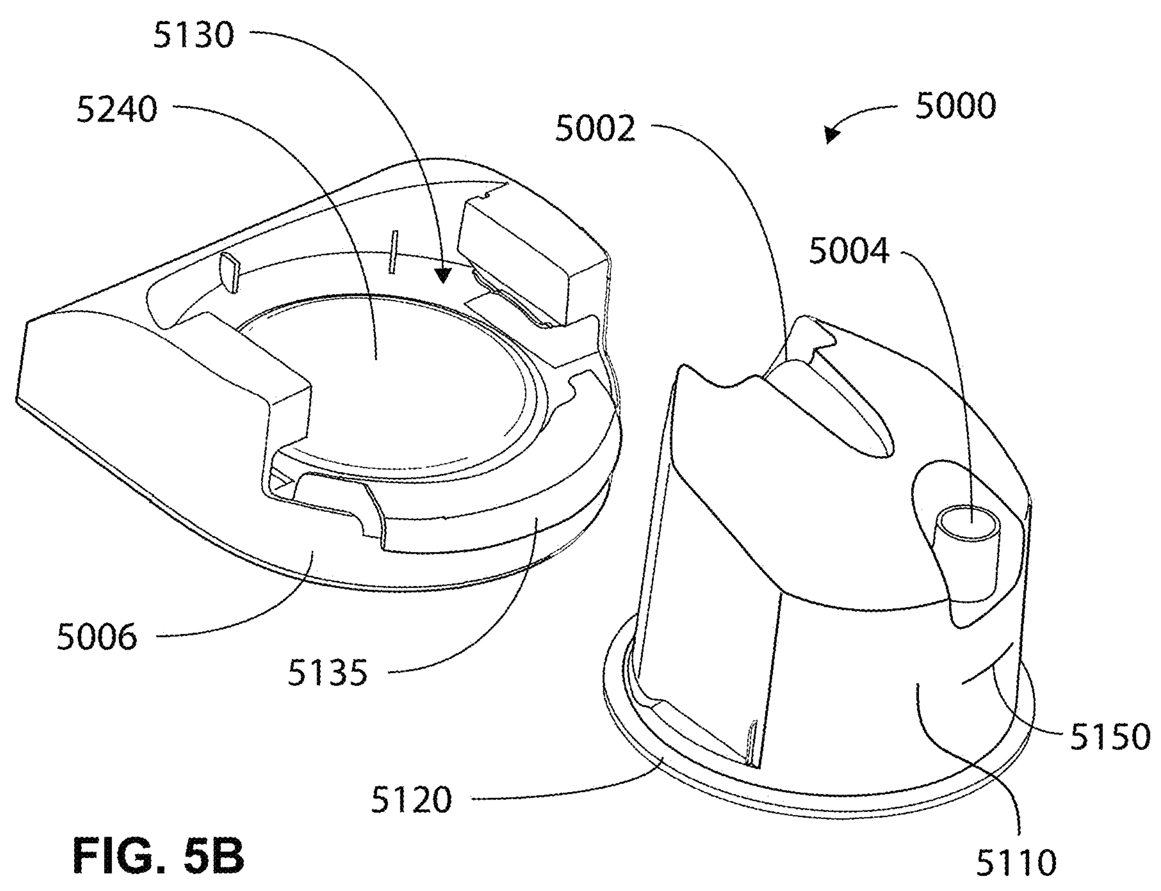

FIG. 5B shows an isometric view of a humidifier in accordance with one form of the present technology, showing a humidifier reservoir 5110 removed from the humidifier reservoir dock 5130.

3.5 Patient Interface

Figure 6A:
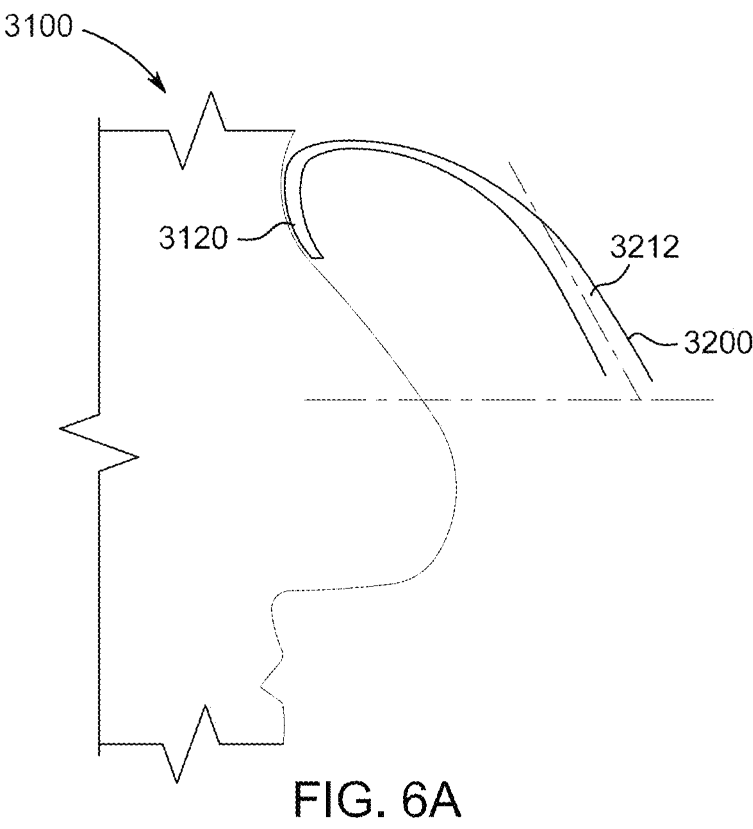

FIG. 6A shows a side view schematic of a seal-forming structure 3100 in contact with a patient's face in a first configuration according to one form of the technology.

Figure 6B:
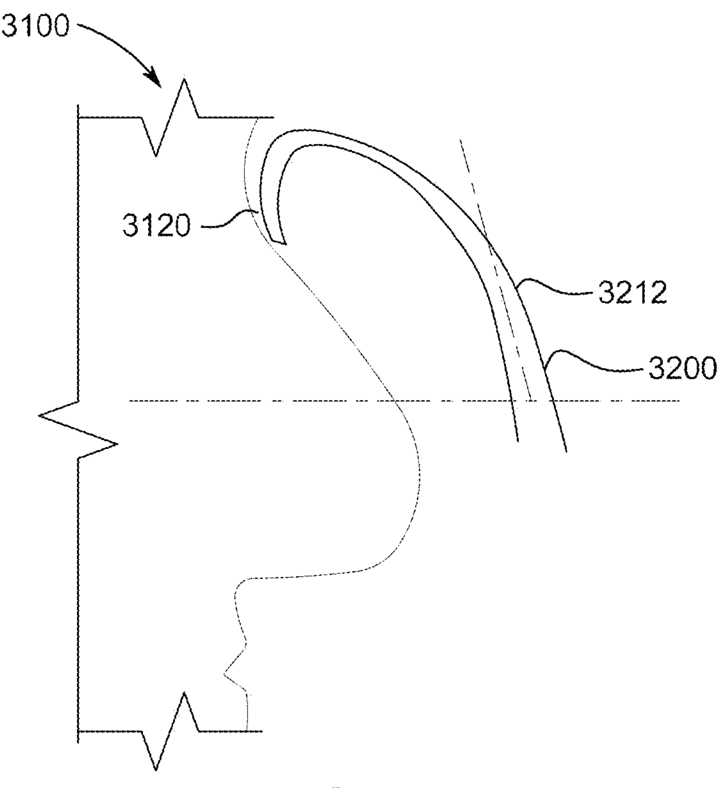

FIG. 6B shows a side view schematic of a seal-forming structure 3100 in contact with a patient's face in a second configuration according to one form of the technology.

Figure 7A:
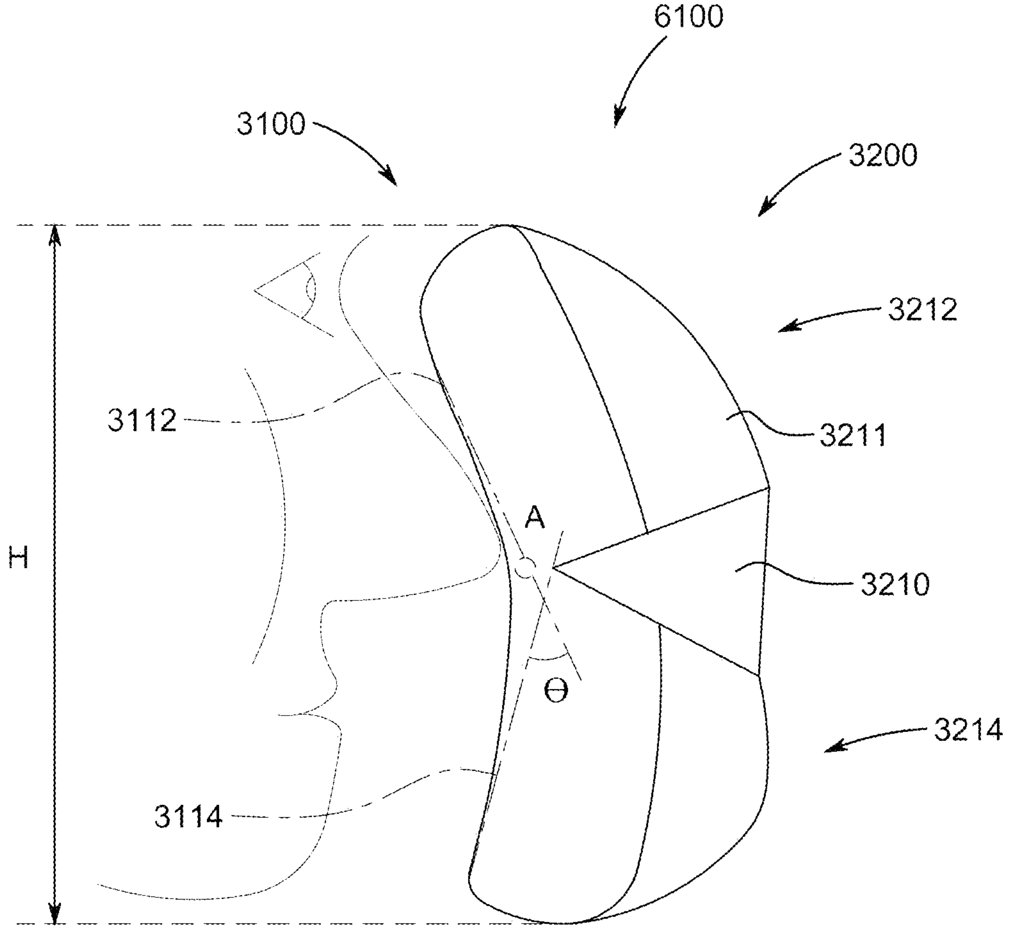

FIG. 7A shows a side view schematic of a cushion module 6100 in approximate engagement with a patient's face in a first configuration according to one form of the technology.

Figure 7B:
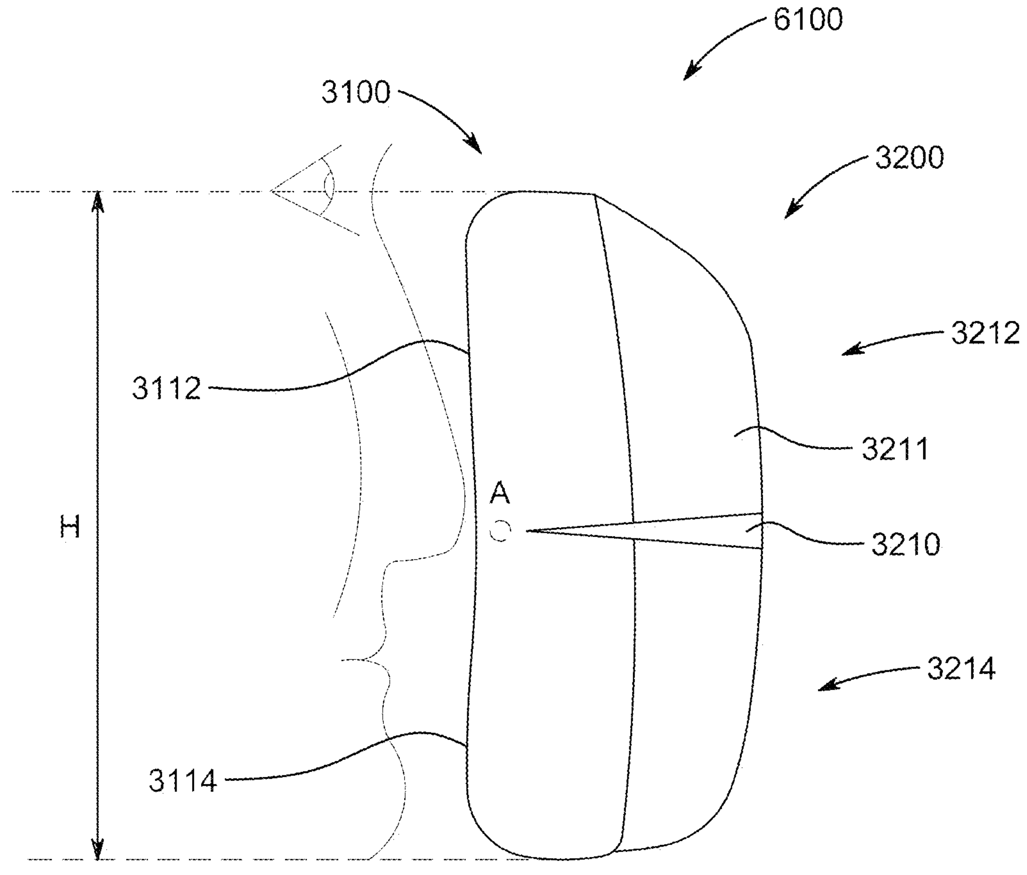

FIG. 7B shows a side view schematic of a cushion module 6100 in approximate engagement with a patient's face in a second configuration according to one form of the technology.

Figure 8A:
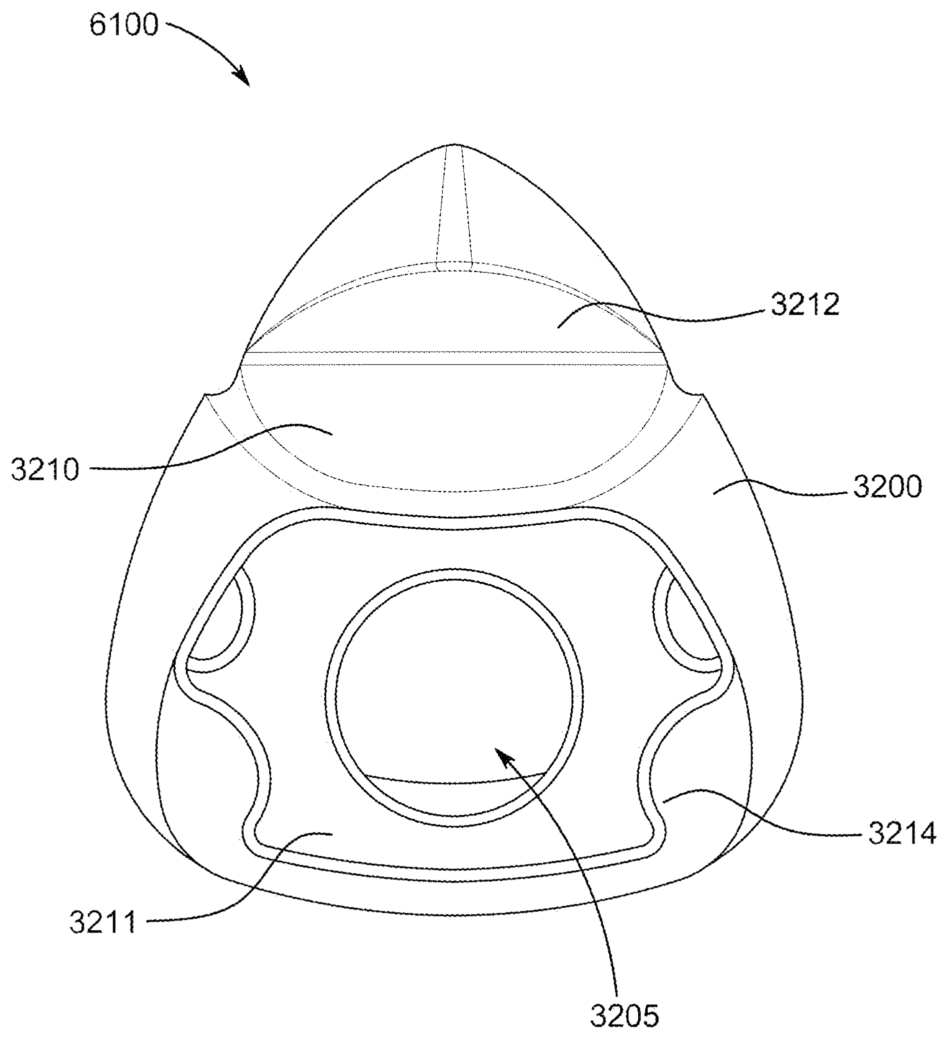

FIG. 8A shows an anterior view of a cushion module 6100 according to one form of the technology.

Figure 8B:
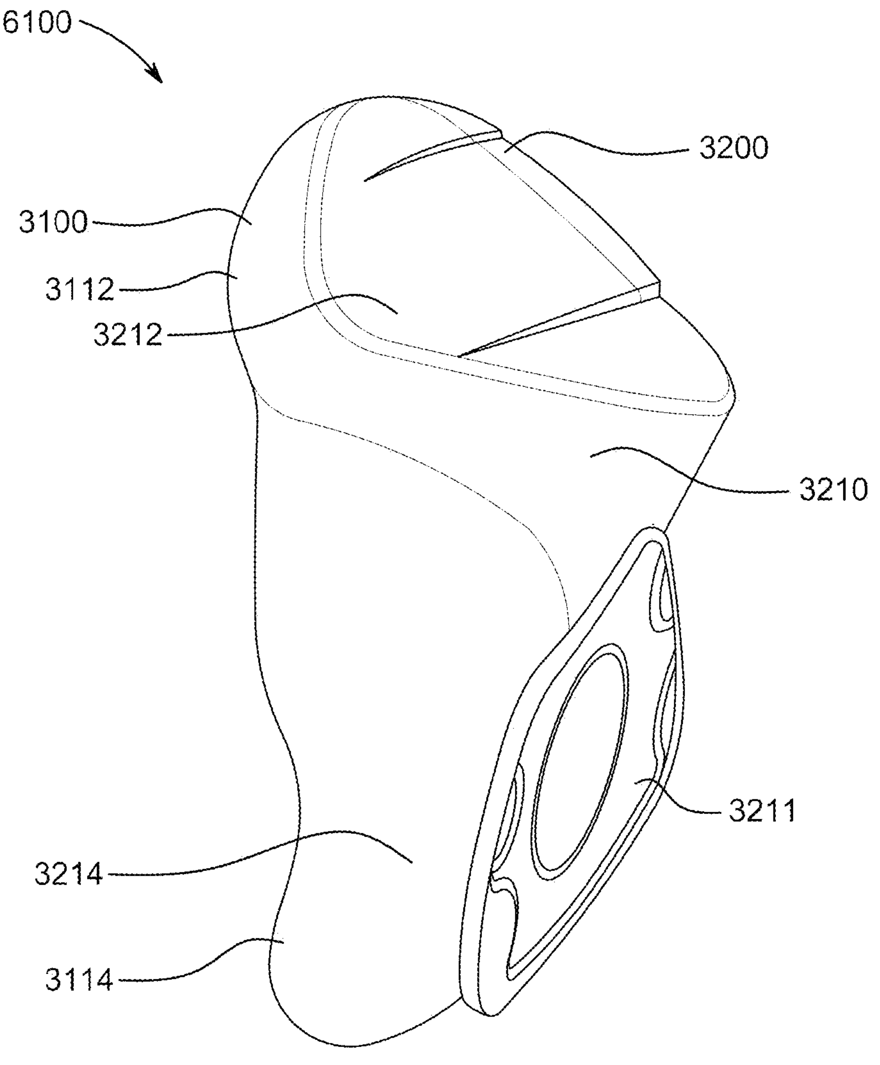

FIG. 8B shows a side view of the cushion module 6100 of FIG. 8A.

Figure 8C:
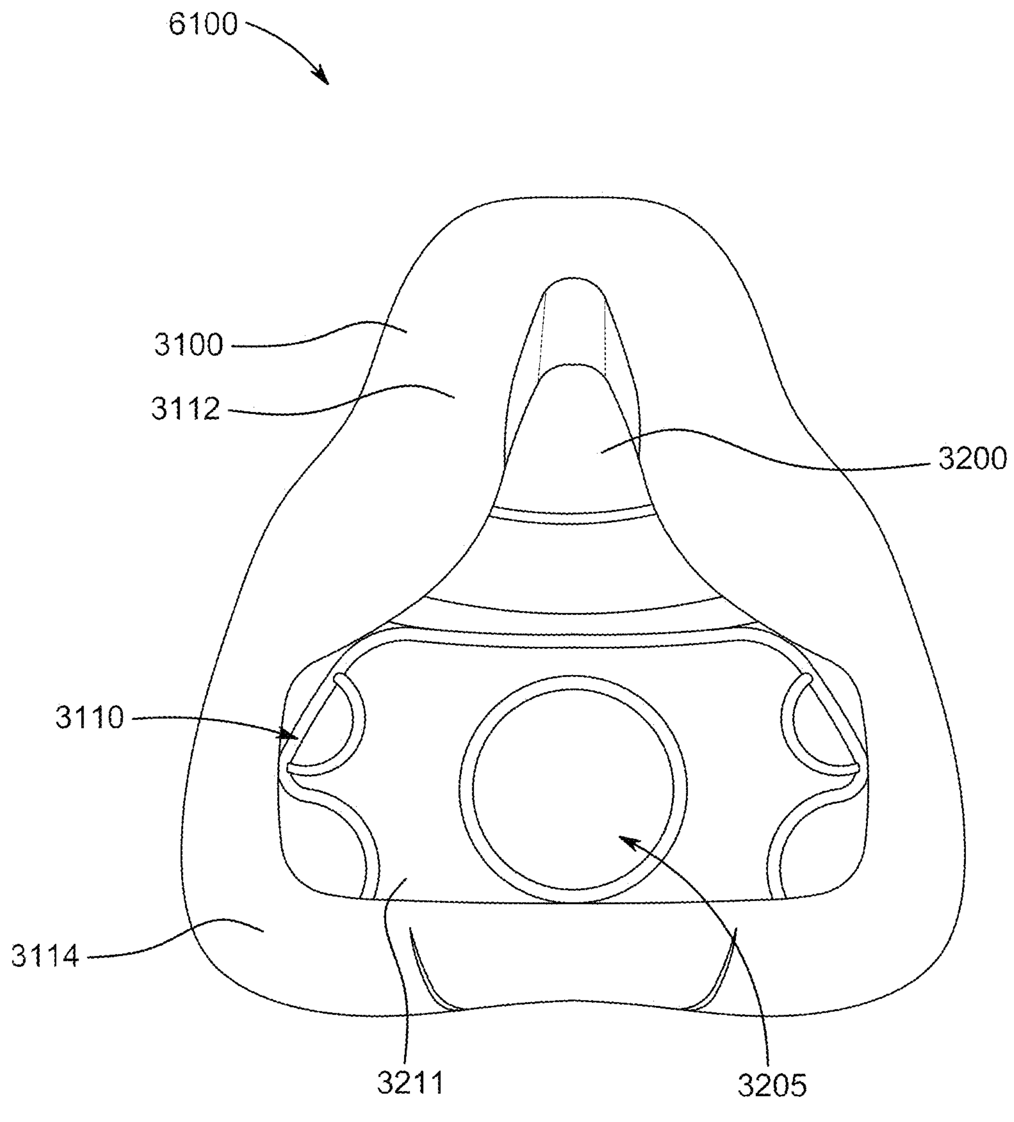

FIG. 8C shows a posterior view of the cushion module 6100 of FIG. 8A.

Figure 9A:
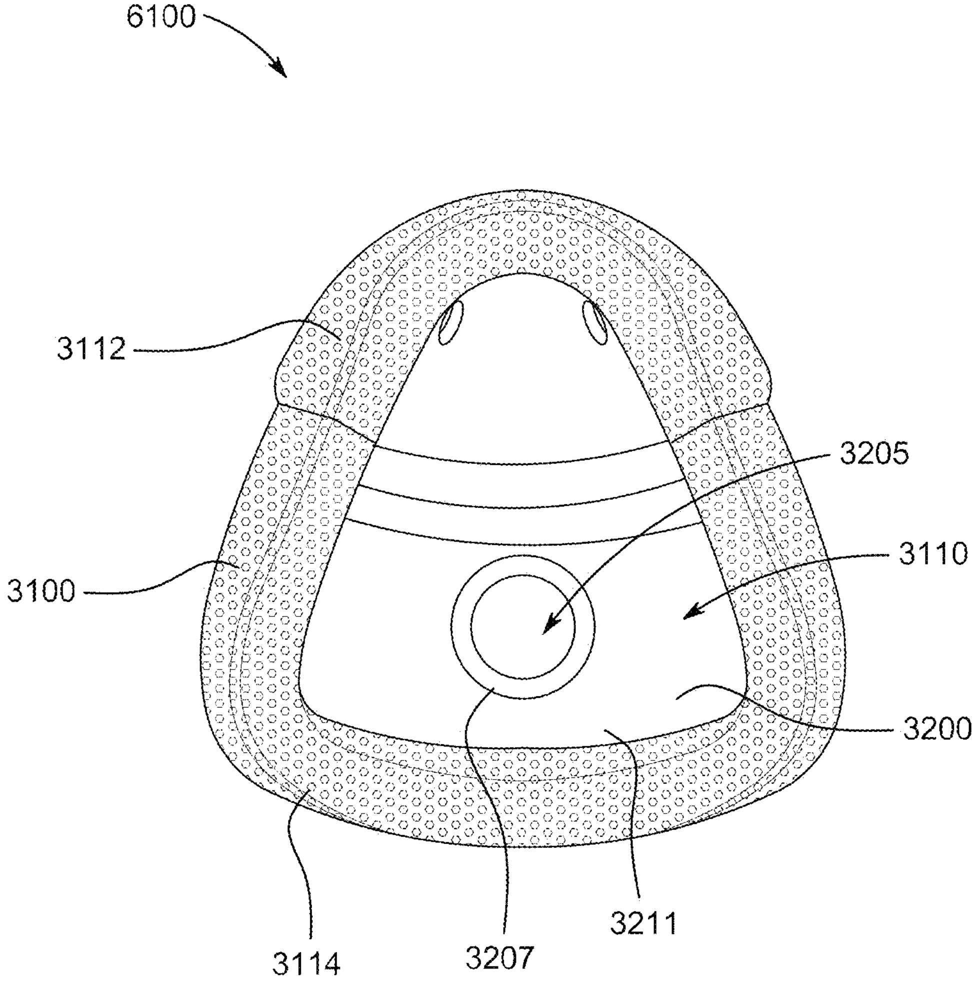

FIG. 9A shows a posterior view of a cushion module 6100 according to one form of the technology.

Figure 9B:
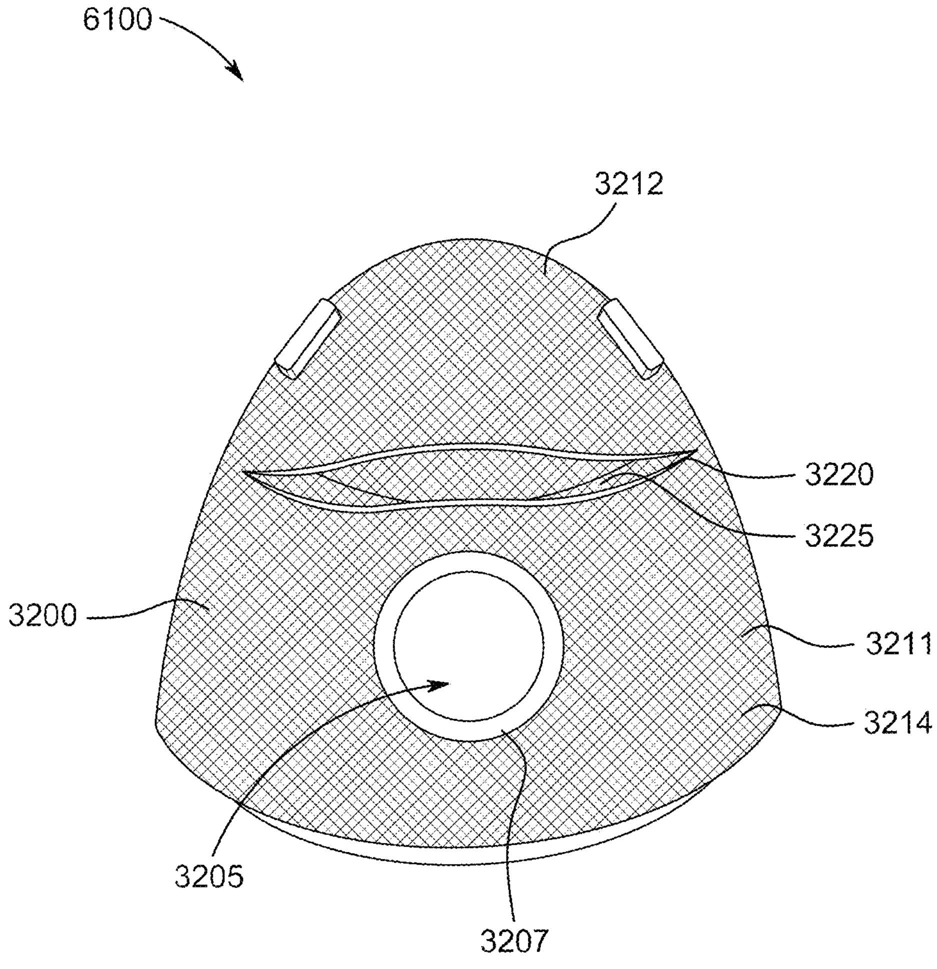

FIG. 9B shows an anterior view of the cushion module 6100 of FIG. 9A.

Figure 9C:
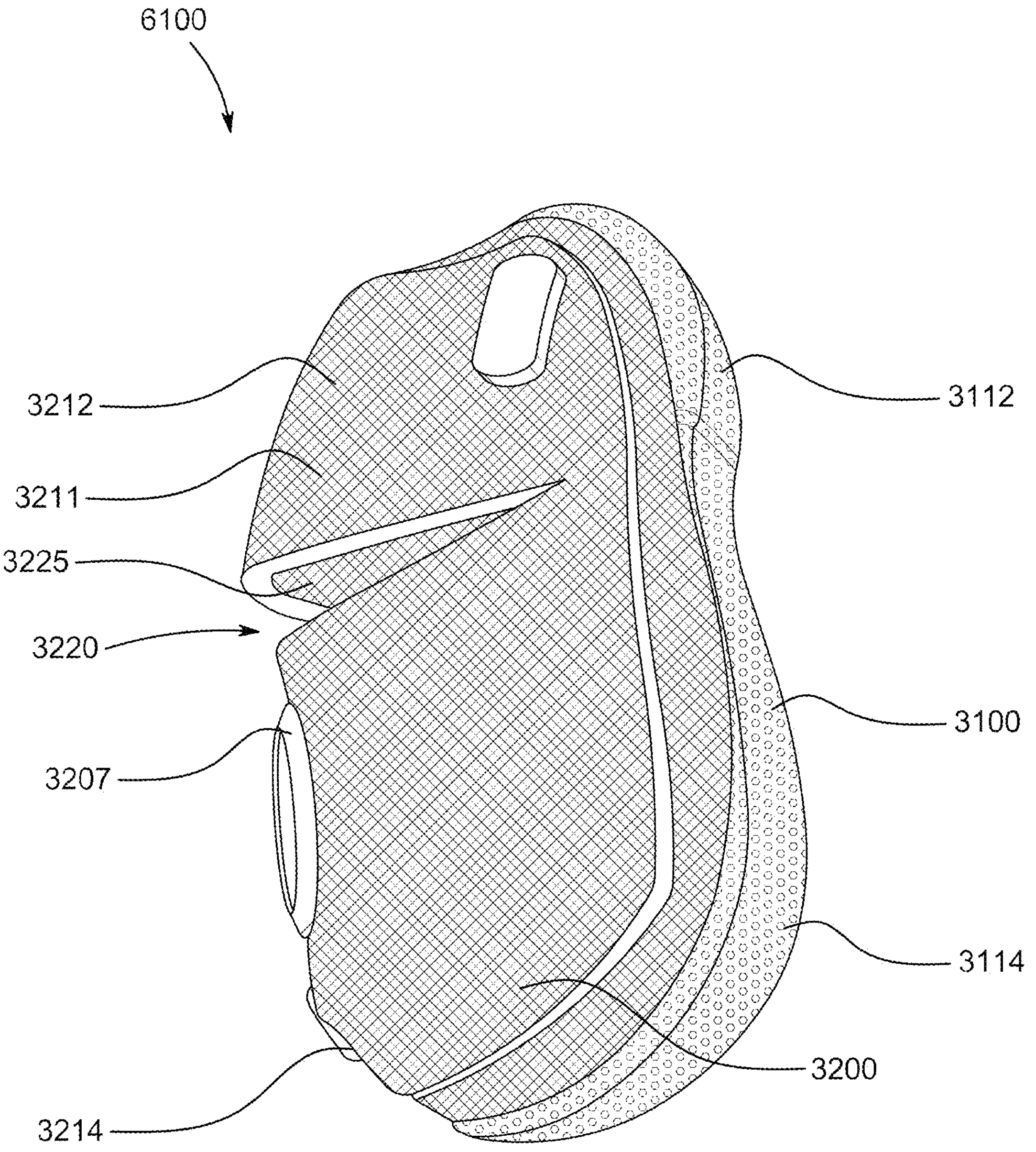

FIG. 9C shows a side view of the cushion module 6100 of FIG. 9A.

Figure 10A:
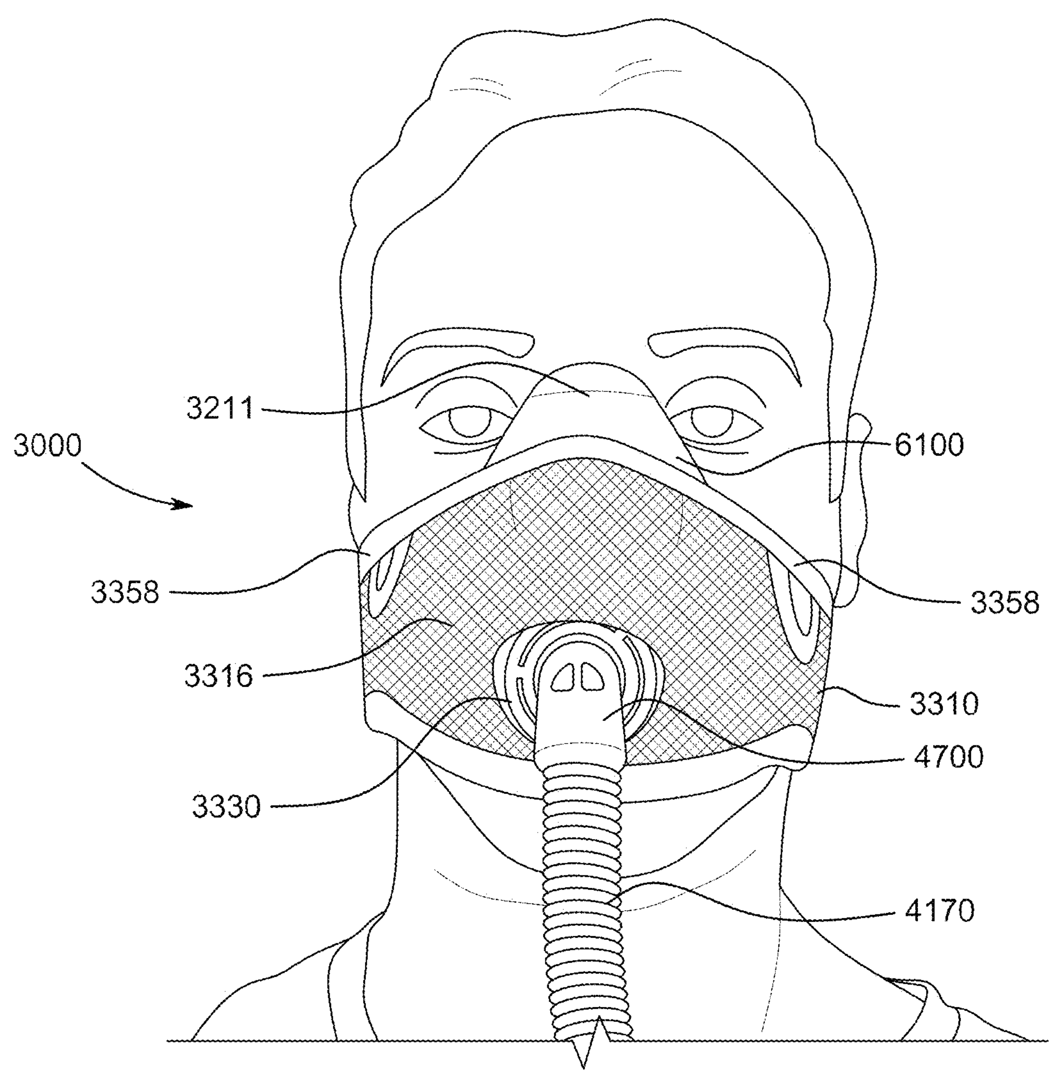

FIG. 10A shows an anterior view of a patient wearing a patient interface 3000 according to one form of the technology.

Figure 10B:
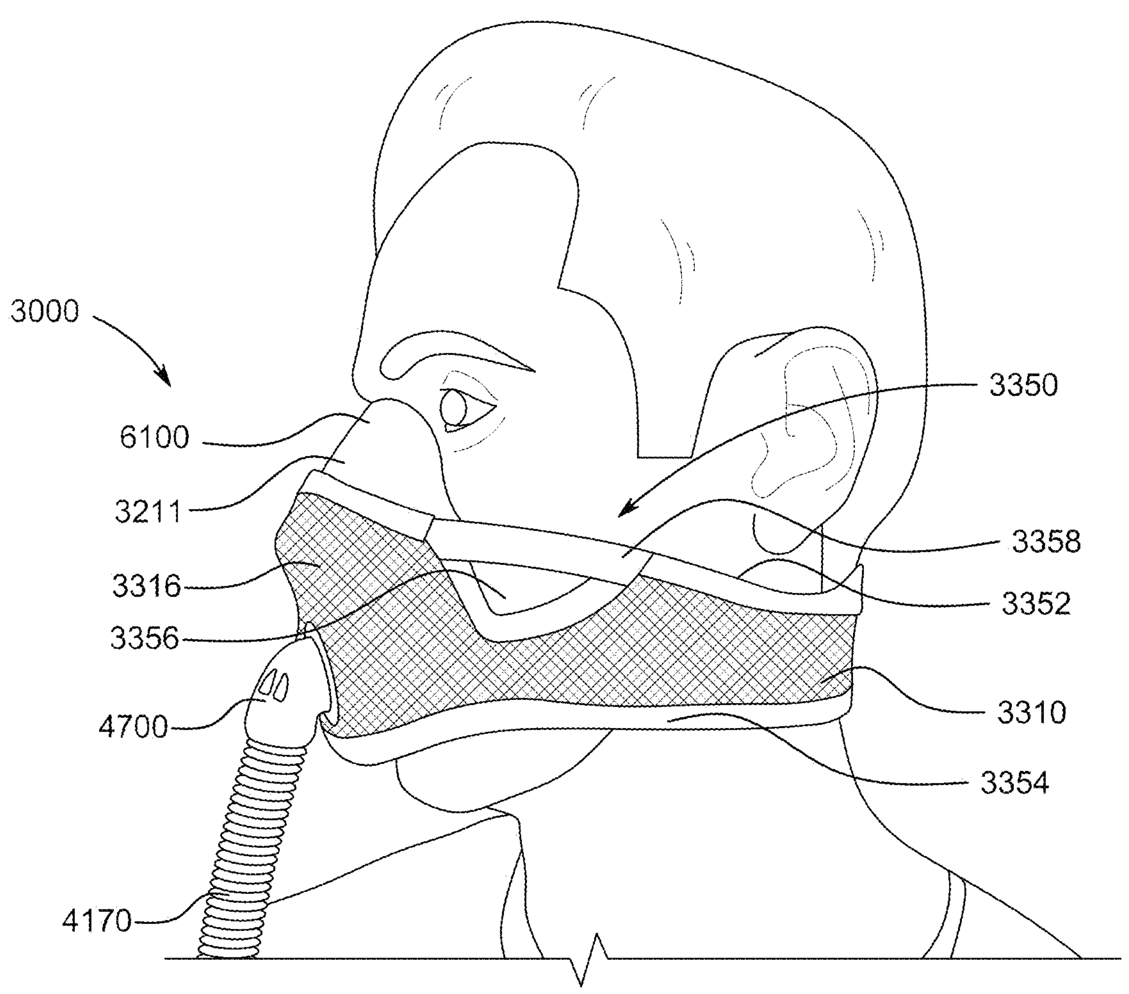

FIG. 10B shows a side view of the patient wearing the patient interface 3000 of FIG. 10A.

Figure 11A:
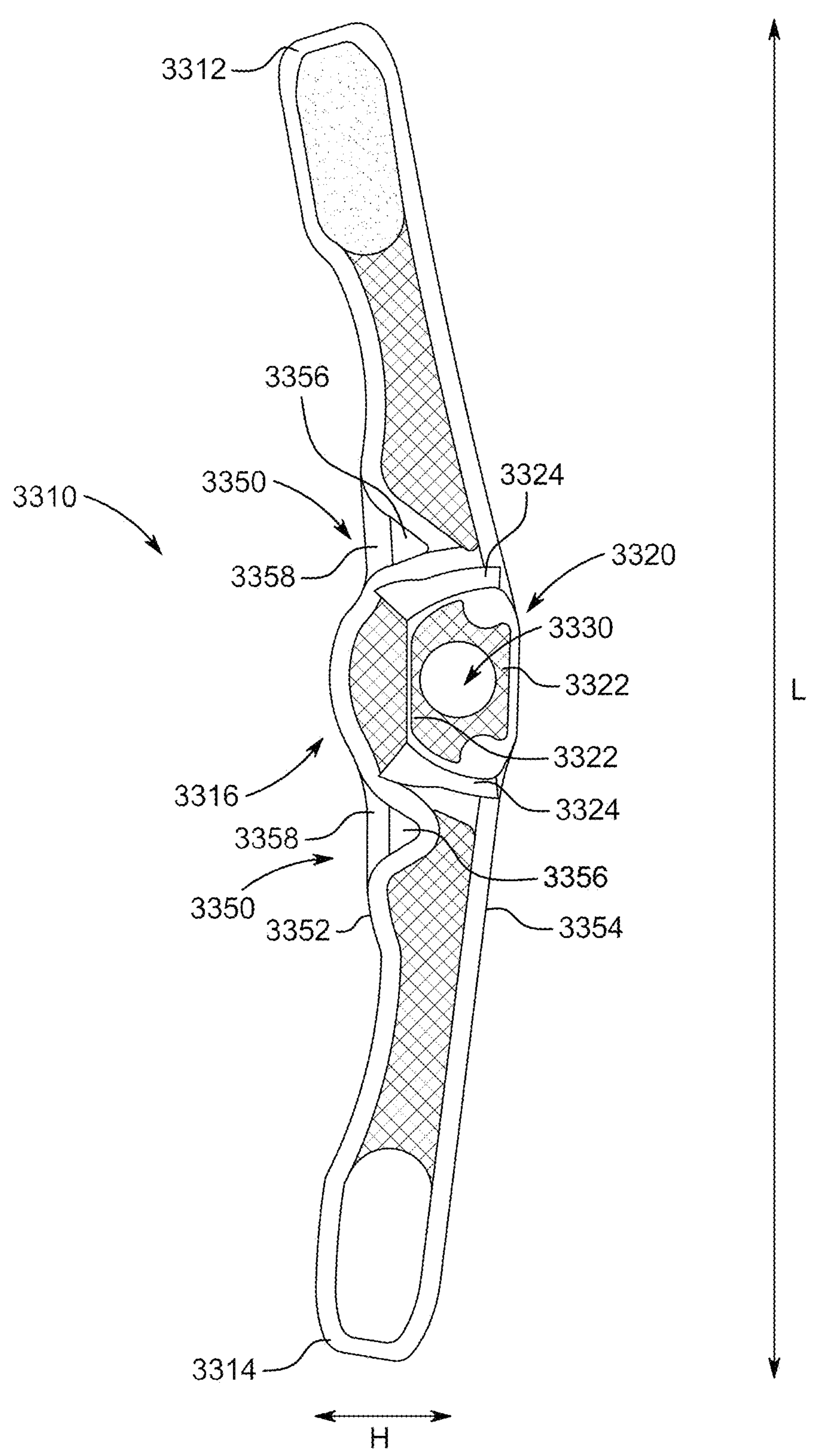

FIG. 11A shows a view of a side of a strap 3310 that faces towards a patient in use according to one form of the technology.

Figure 11B:
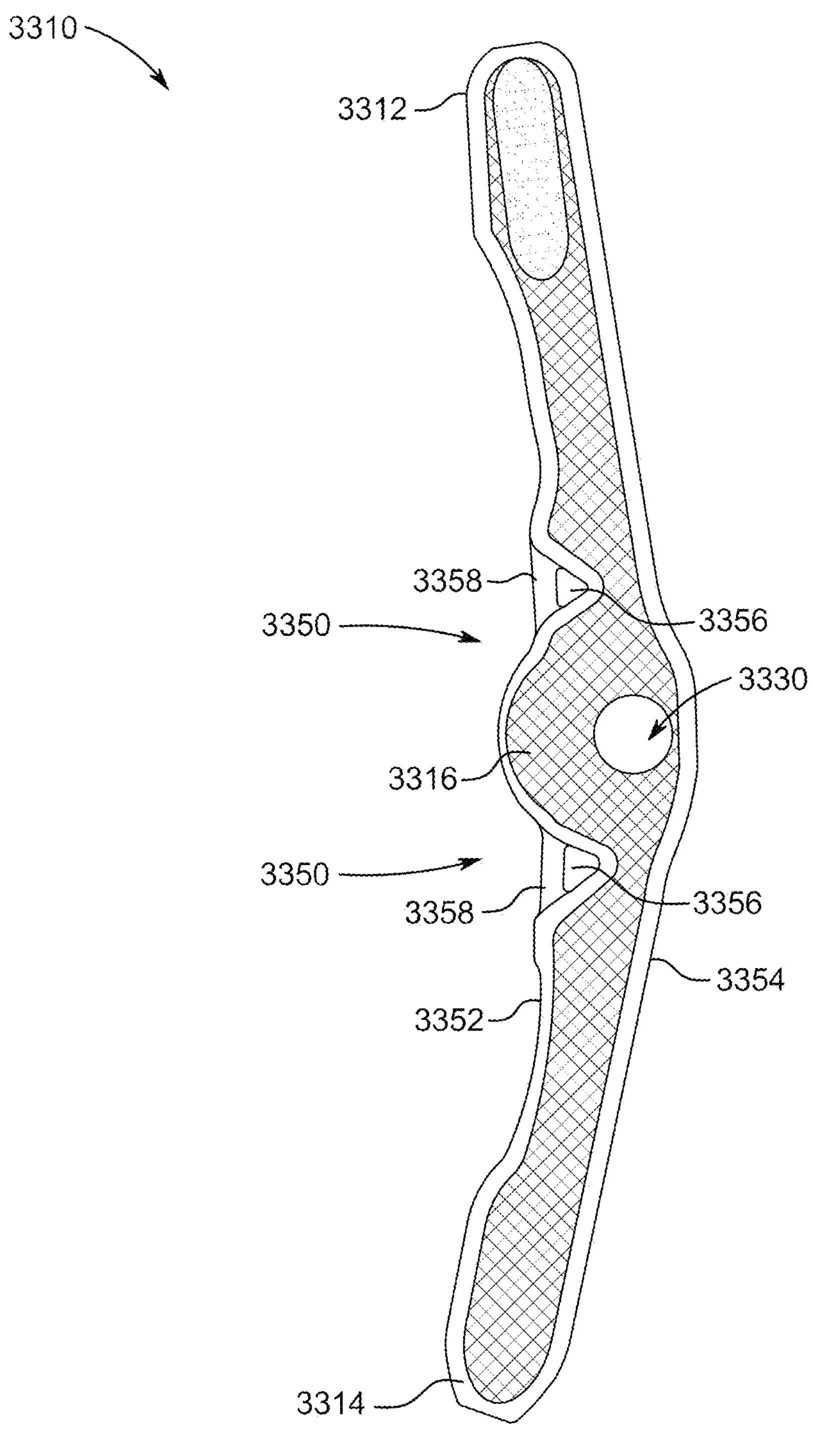

FIG. 11B shows a view of the side of the strap 3310 of FIG. 11A that faces away from the patient in use.

Figure 11C:
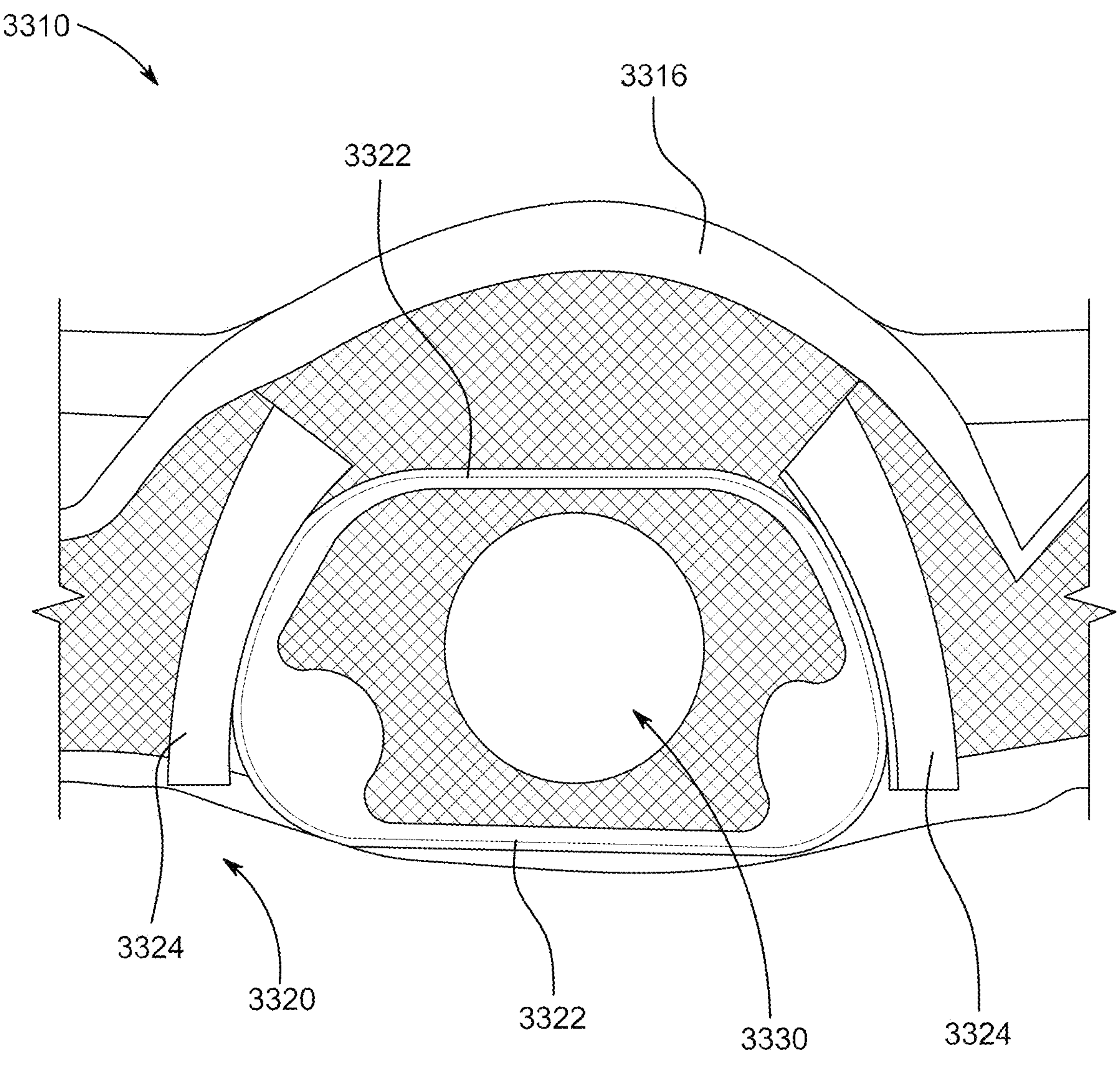

FIG. 11C shows a close-up view of a cushion engaging portion 3316 of the strap 3310 of FIG. 11A.

Figure 12A:
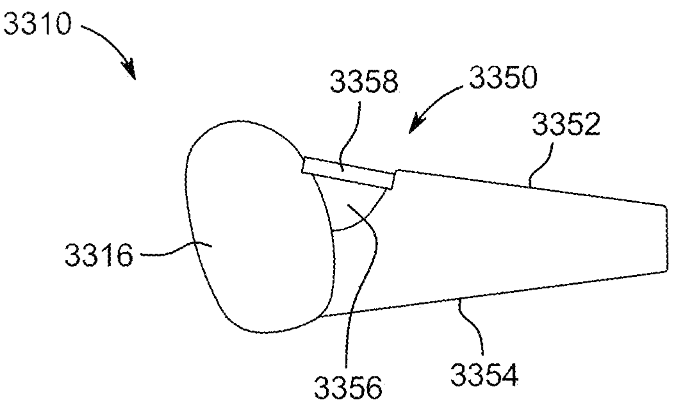

FIG. 12A shows a schematic of an elastic region 3350 of a strap 3310 according to one form of the technology.

Figure 12B:
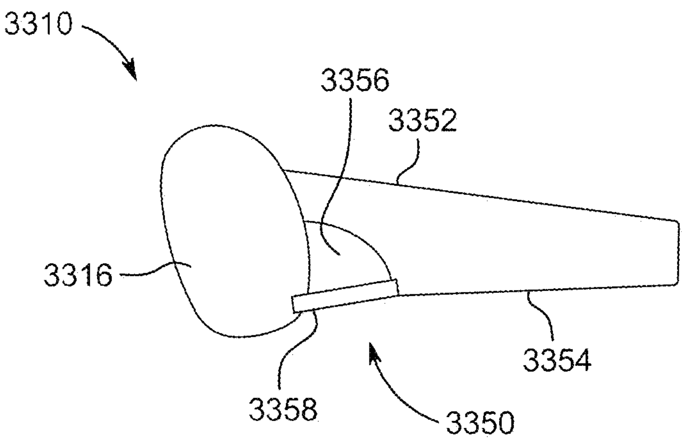

FIG. 12B shows a schematic of an elastic region 3350 of another strap 3310 according to one form of the technology.

Figure 12C:
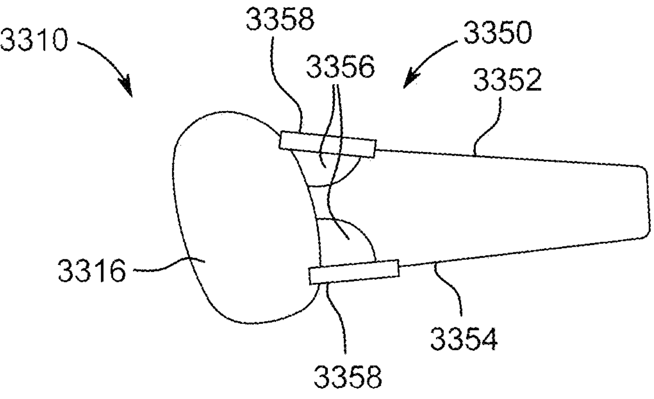

FIG. 12C shows a schematic of an elastic region 3350 of another strap 3310 according to one form of the technology.

Figure 13A:
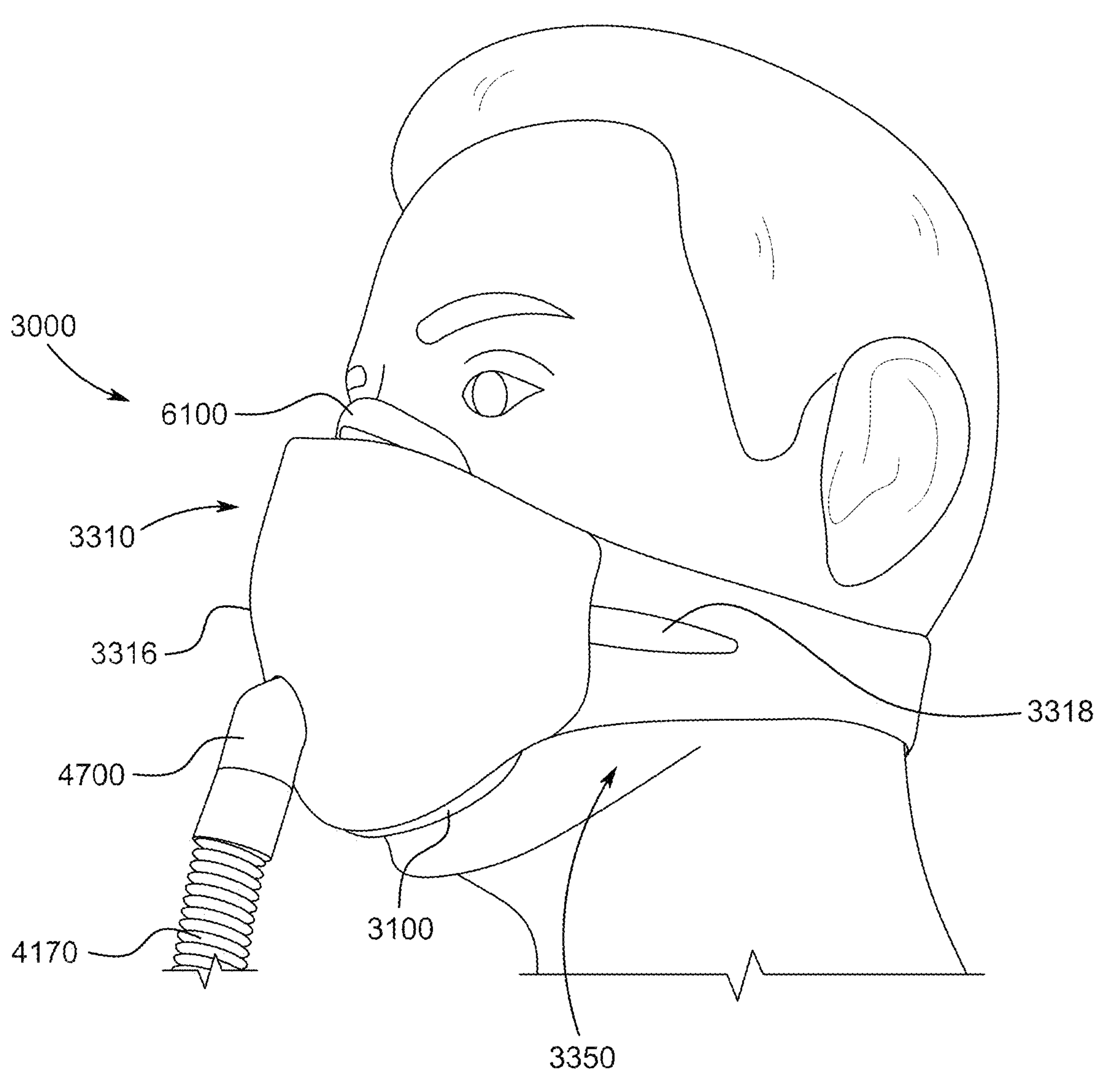

FIG. 13A shows a side view of a patient wearing a patient interface 3000 according to one form of the technology.

Figure 13B:
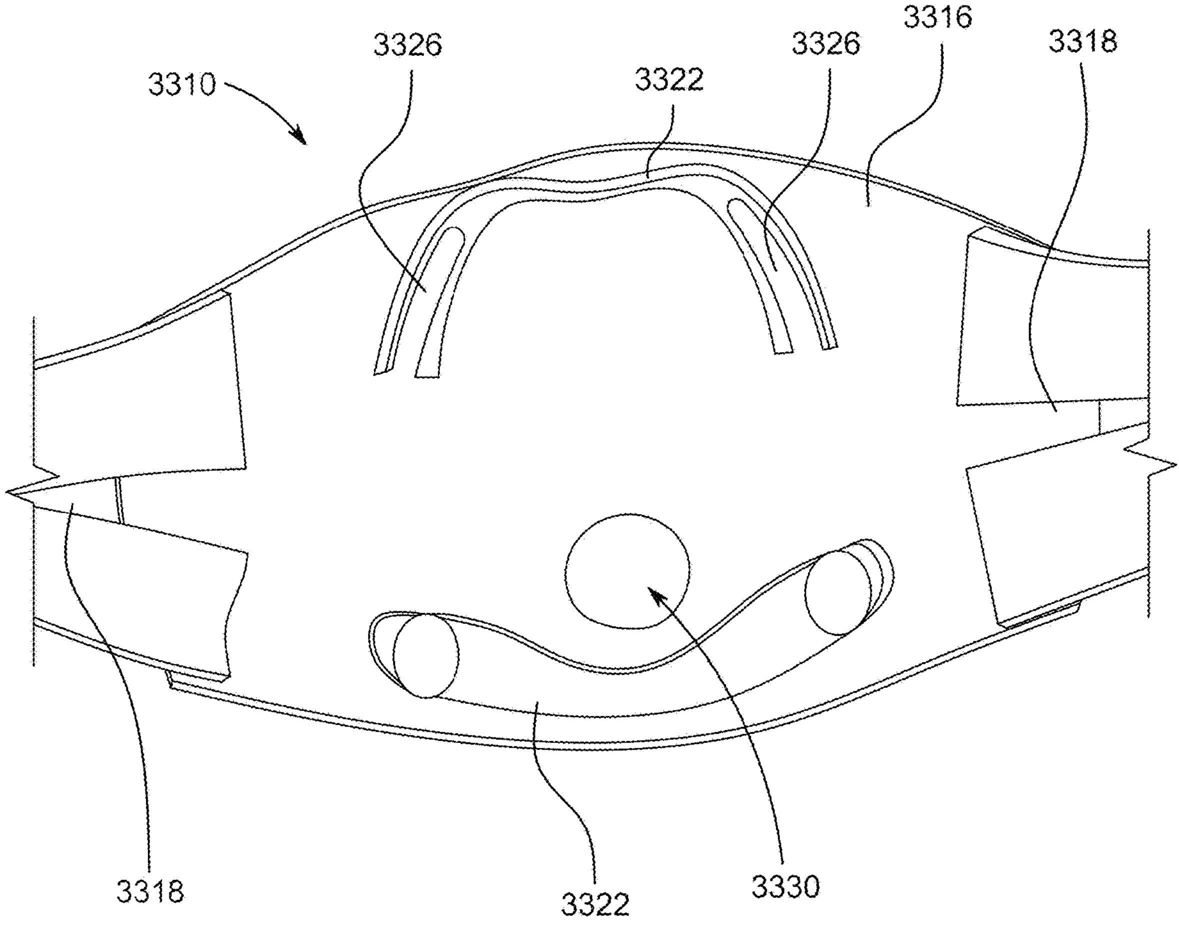

FIG. 13B shows a close-up view of a cushion engaging portion 3316 of the strap 3310 of the patient interface 3000 of FIG. 13A.

Figure 14A:
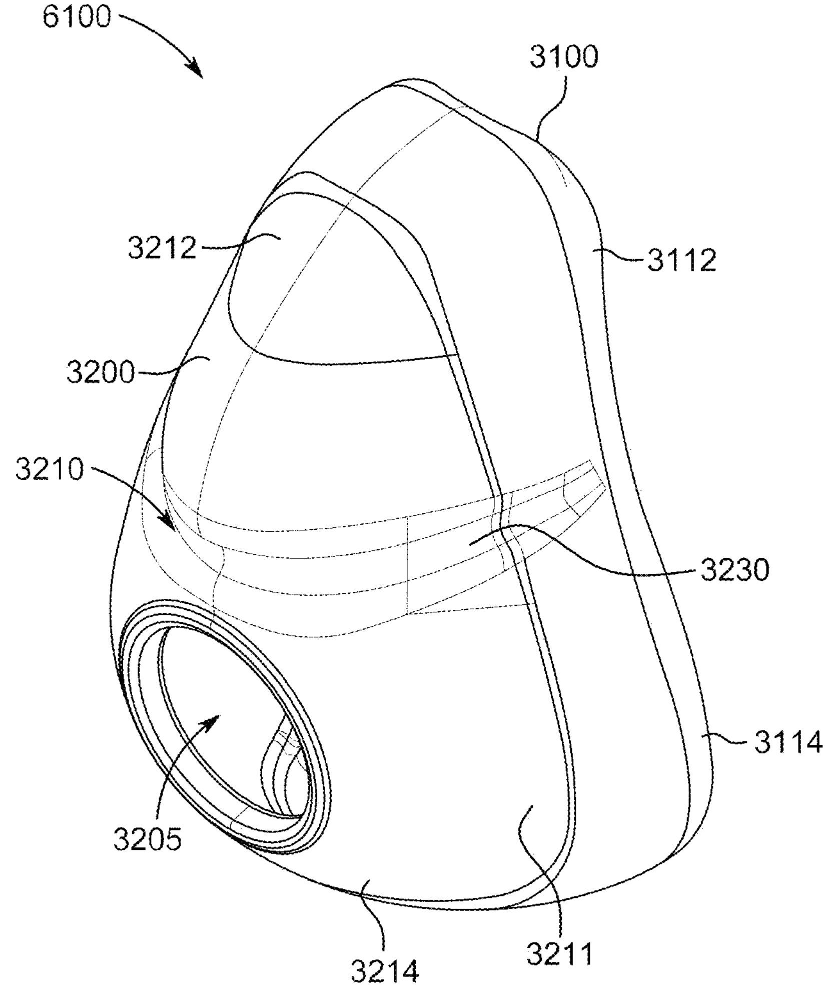

FIG. 14A shows a perspective view of a cushion module 6100 according to one form of the technology.

Figure 14B:
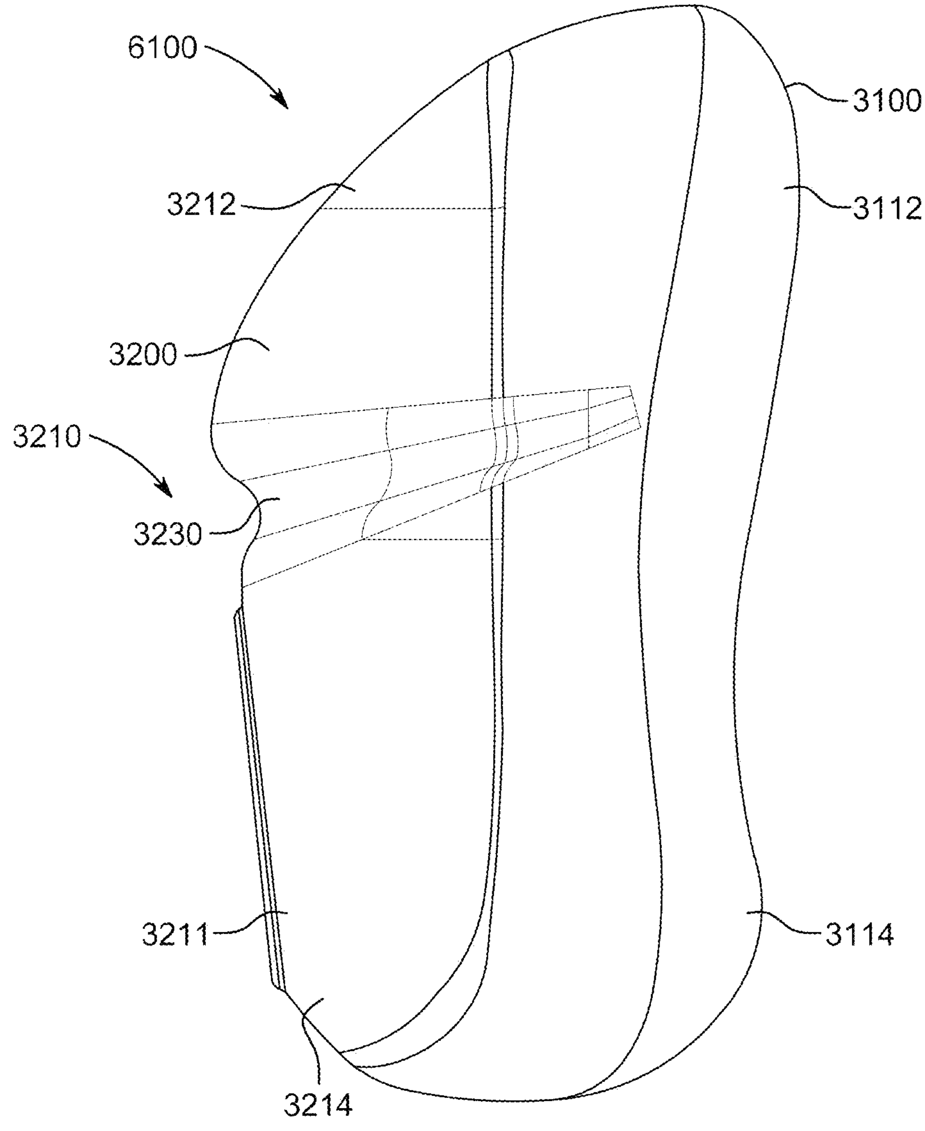

FIG. 14B shows a side view of the cushion module 6100 shown in FIG. 14A.

Figure 14C:
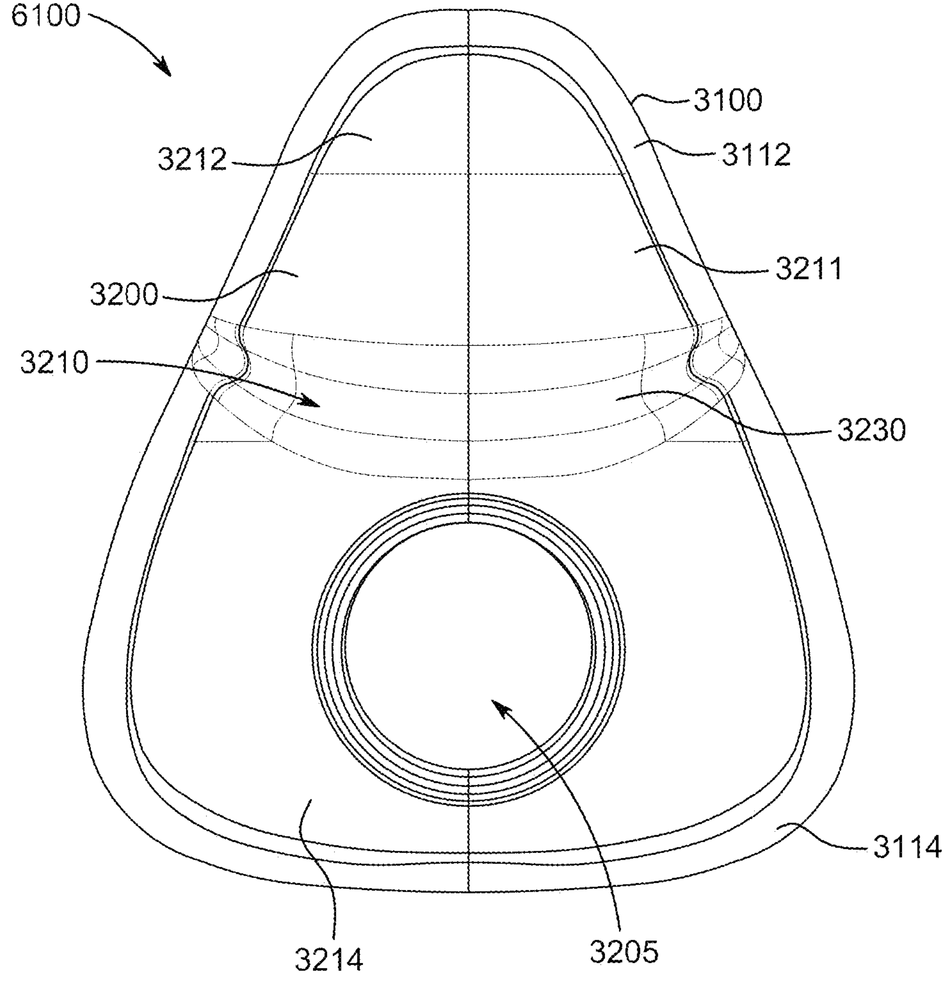

FIG. 14C shows a front view of the cushion module 6100 shown in FIG. 14A.

Figure 14D:
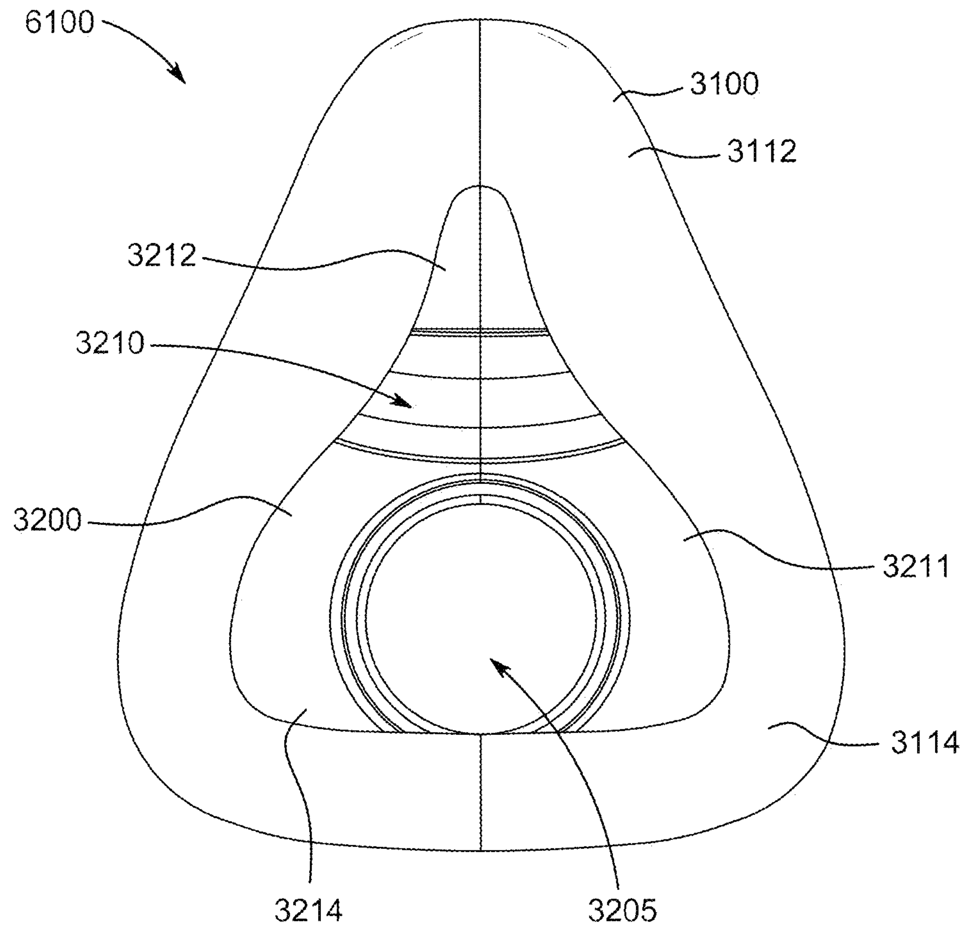

FIG. 14D shows a rear view of the cushion module 6100 shown in FIG. 14A.

Figure 15A:
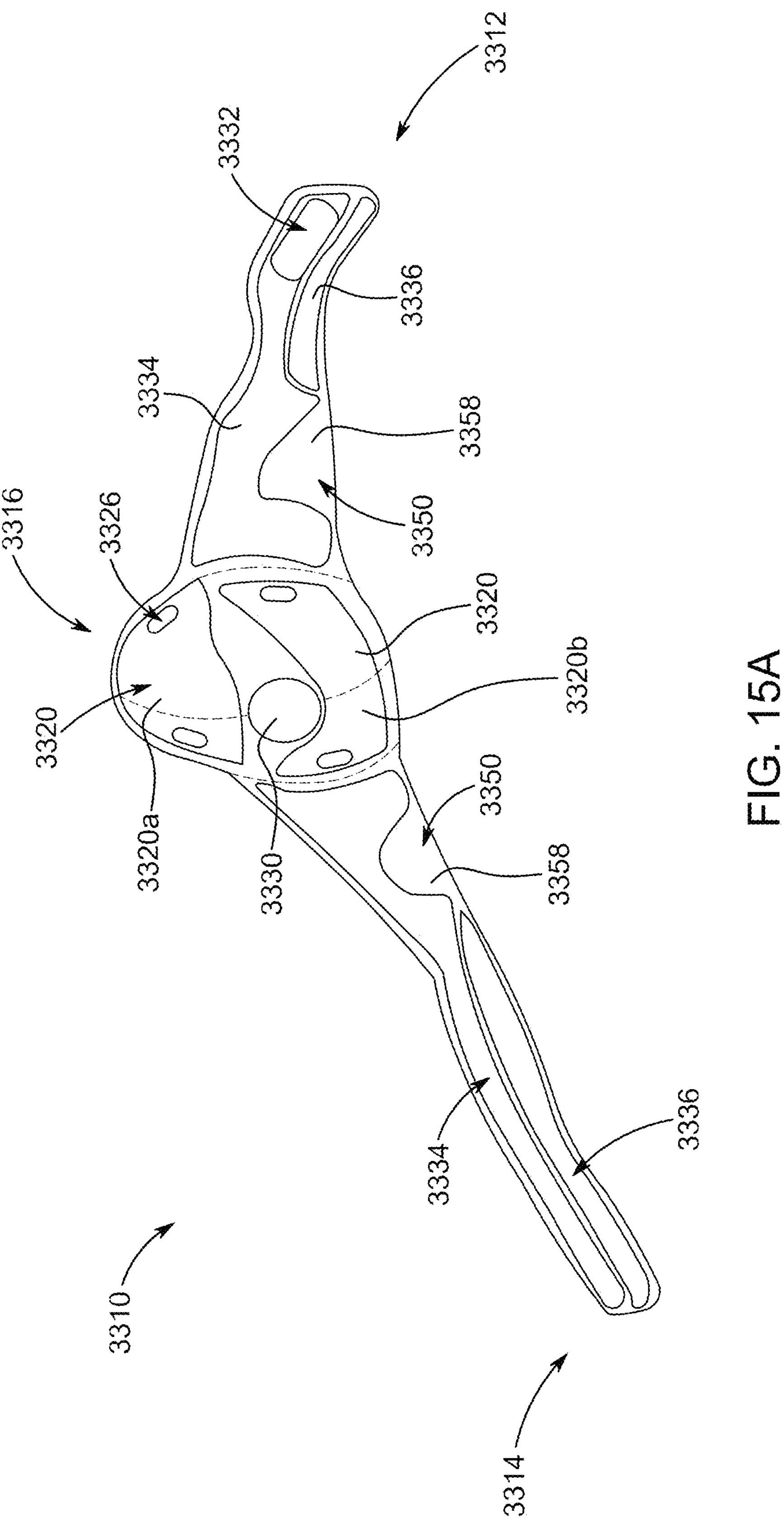

FIG. 15A shows a strap 3310 according to another example of the present technology.

Figure 15B:
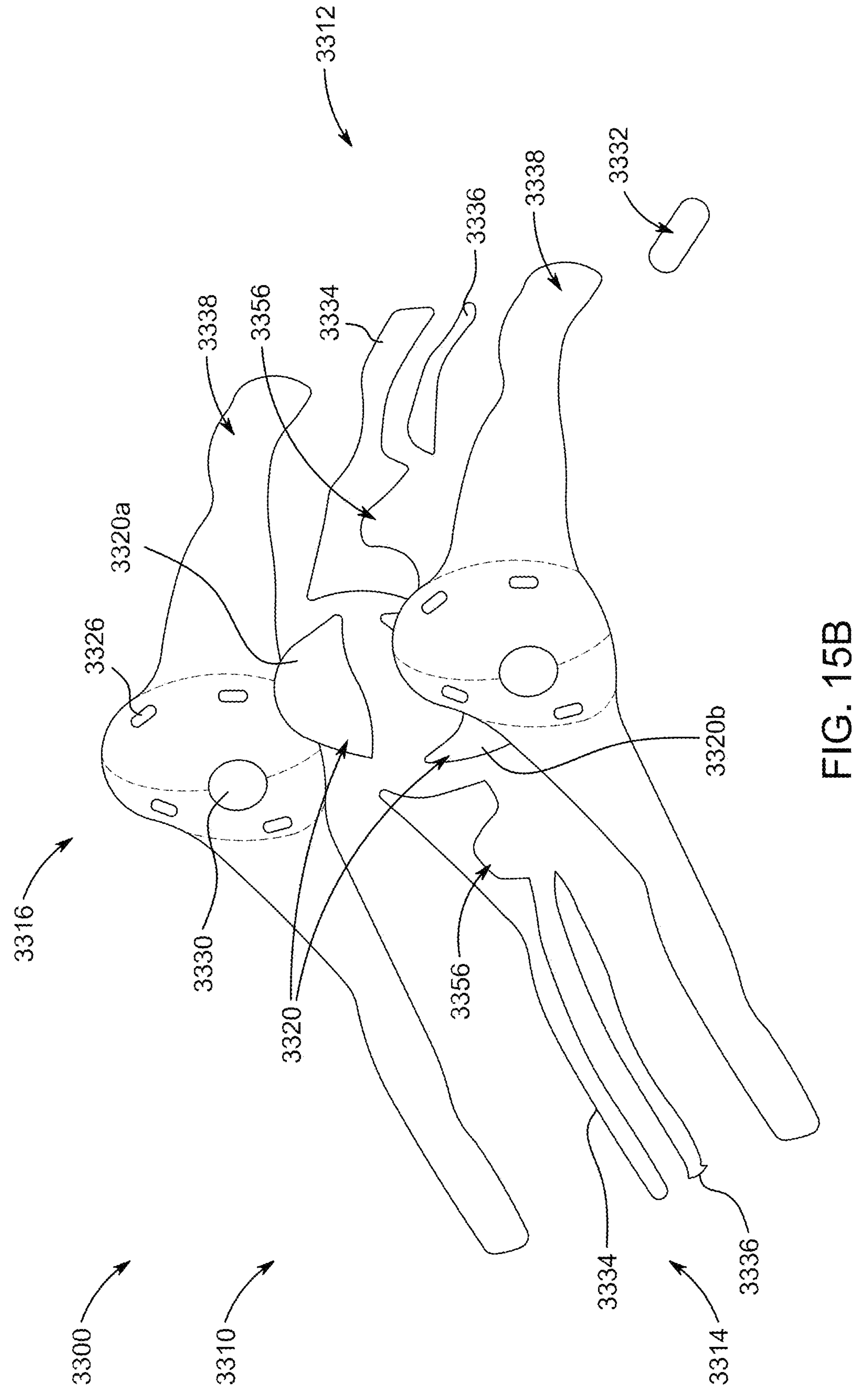

FIG. 15B shows an exploded view of the strap 3310 shown in FIG. 15A.

Figure 16A:
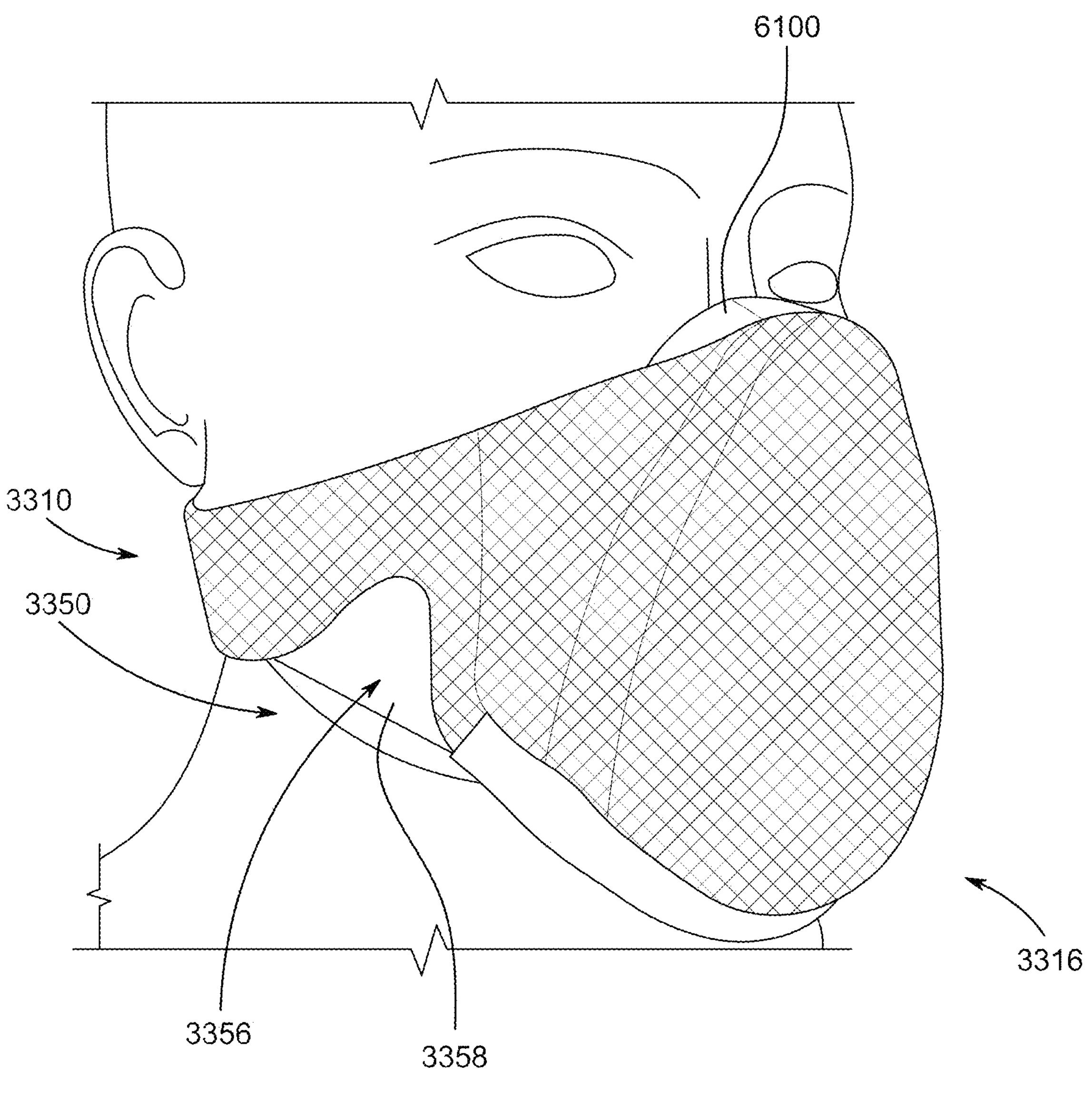

FIG. 16A shows a strap 3310 according to another example of the present technology donned by a patient.

Figure 16B:
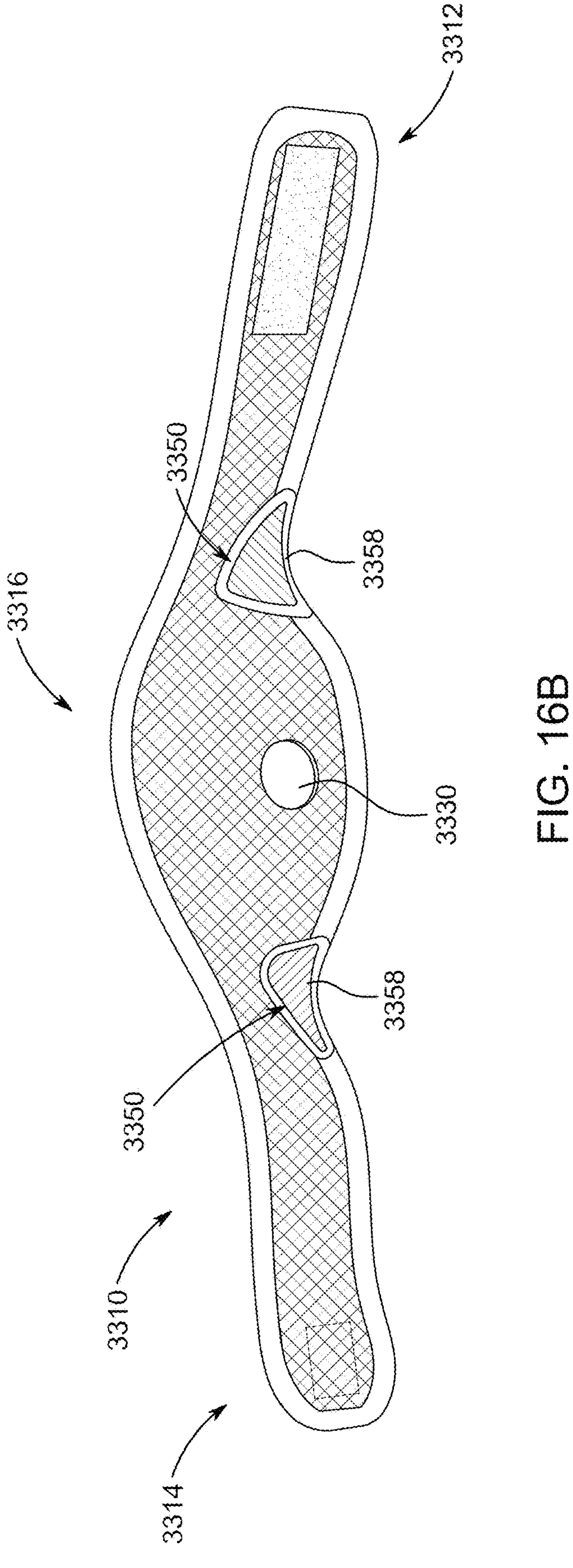

FIG. 16B shows a view of the side of the strap 3310 shown in FIG. 16A that faces towards a patient in use.

Figure 17B:
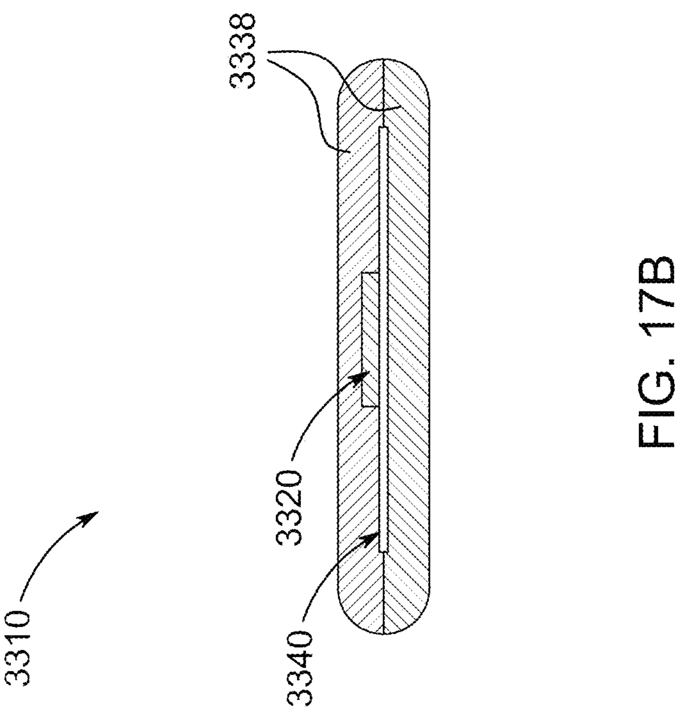
Figure 17A:
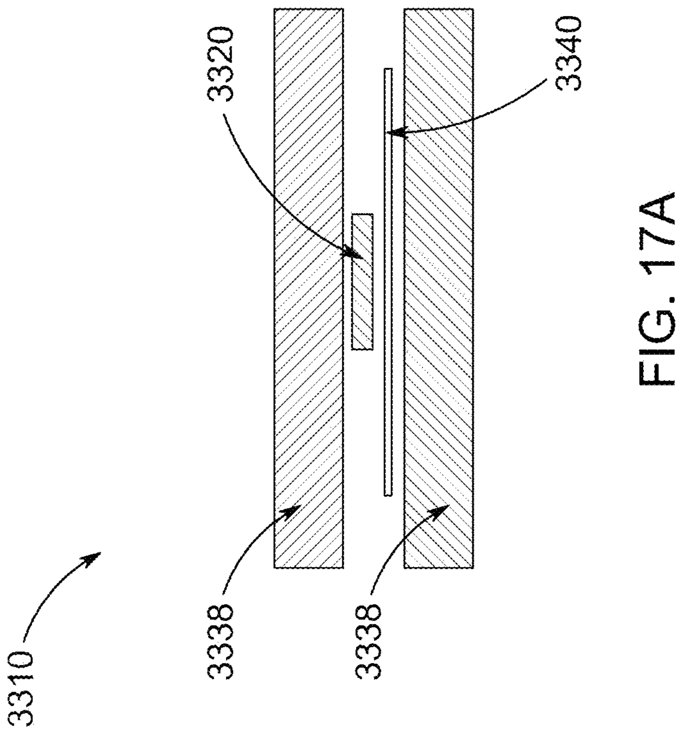

FIG. 17A shows a schematic illustration of layers of a strap 3310 according to another example of the present technology prior to a forming process during manufacturing.

FIG. 17B shows a schematic illustration of the strap 3310 depicted in FIG. 17A after the manufacturing process to join the layers.

Figure 18A:
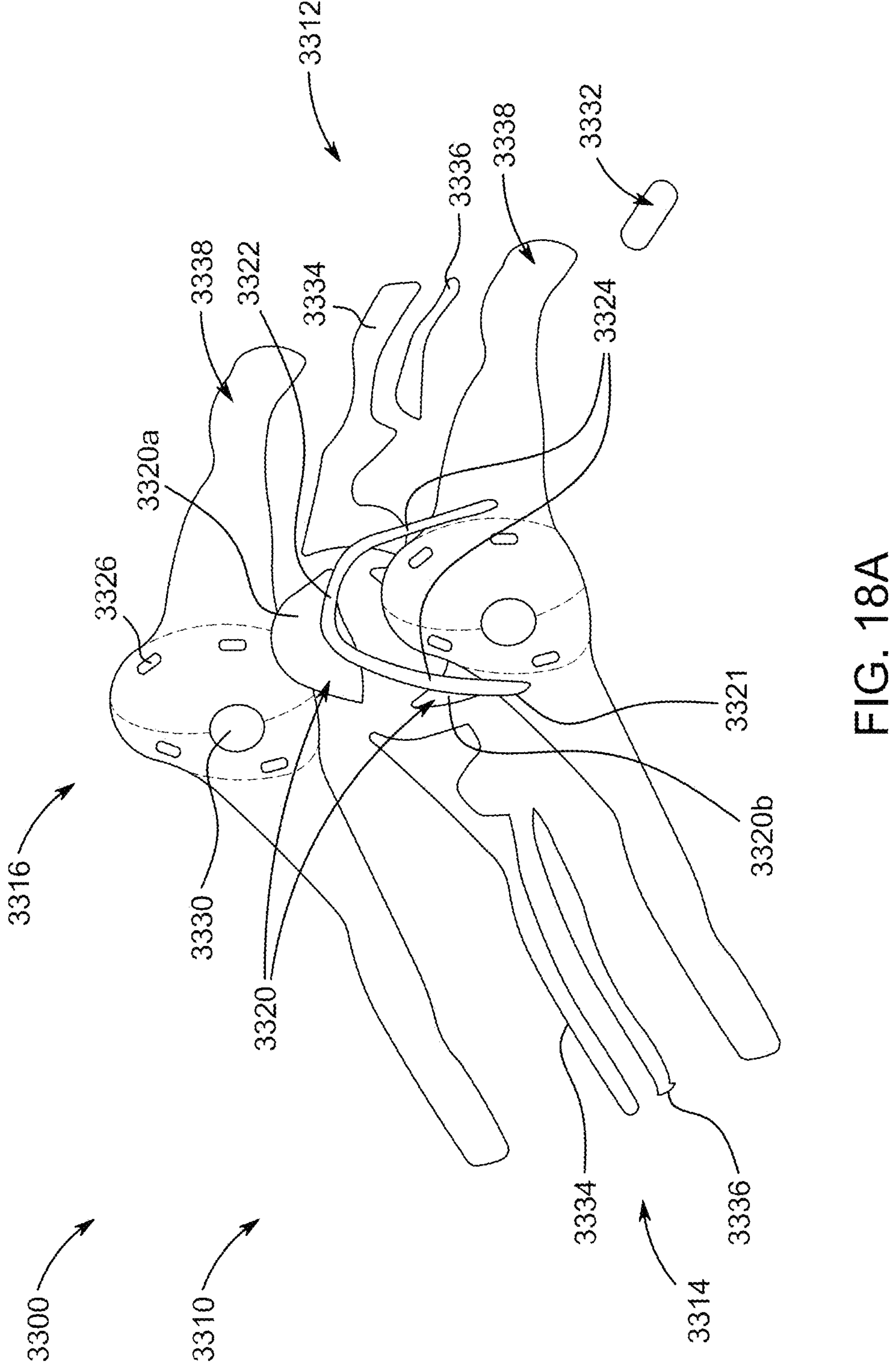

FIG. 18A shows an exploded view of a strap 3310 according to another example of the present technology.

Figure 18B:
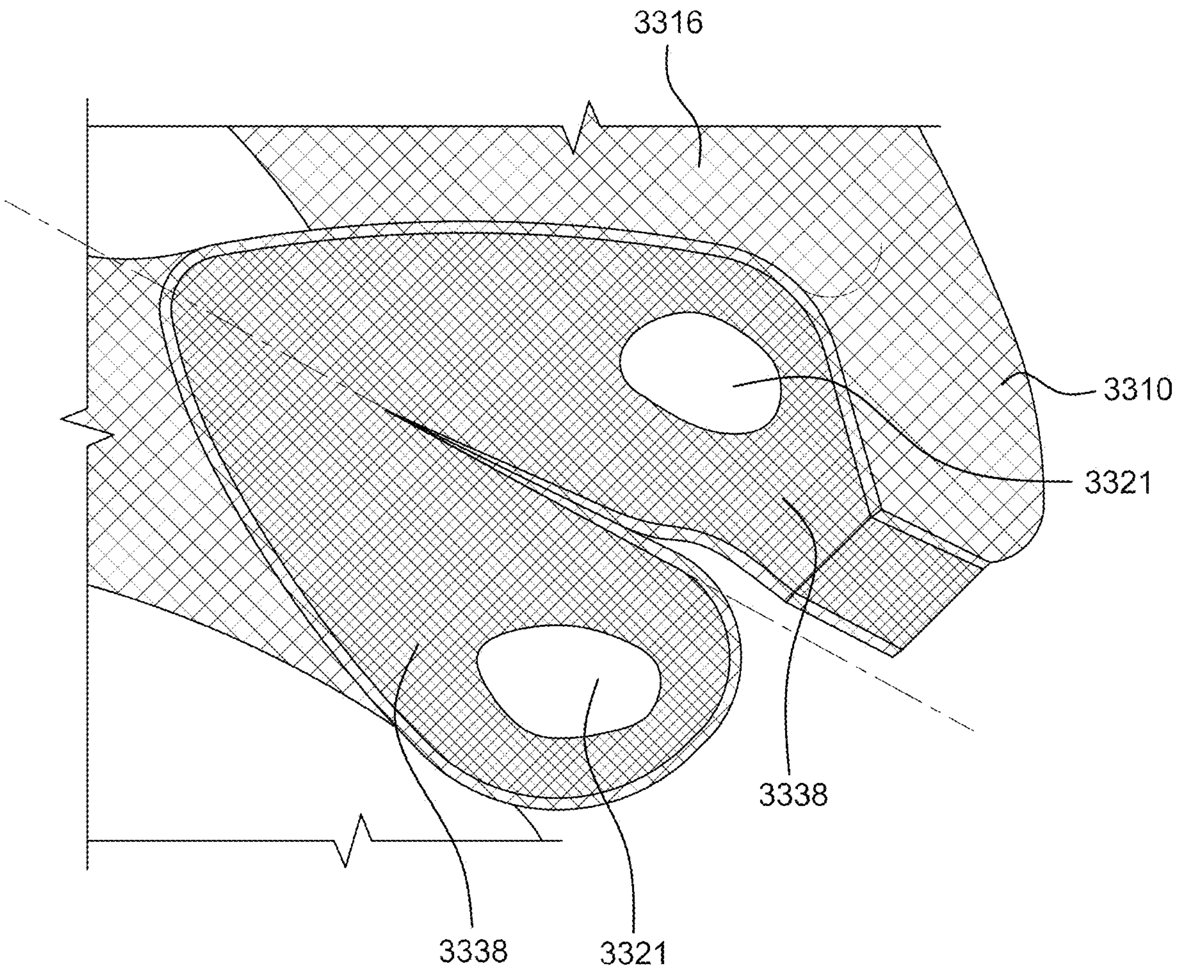

FIG. 18B shows a view of a cut in a periphery of a cushion engaging portion 3316 of the strap 3310 shown in FIG. 18A.

4 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

4.1 Therapy

In one form, the present technology comprises a method for treating a respiratory disorder comprising applying positive pressure to the entrance of the airways of a patient 1000.

In certain examples of the present technology, a supply of breathable gas (which may be referred to as "air") at positive pressure is provided to the nasal passages of the patient via one or both nares. In certain forms, the supply of breathable gas may additionally be provided to the mouth of the patient.

4.2 Respiratory Therapy Systems

In one form, the present technology comprises a respiratory therapy system for treating a respiratory disorder. The respiratory therapy system may comprise an RPT device 4000 for supplying a flow of air to the patient 1000 via an air circuit 4170 and a patient interface 3000.

4.3 Patient Interface

A non-invasive patient interface 3000 in accordance with certain aspects of the present technology comprises the following functional aspects: a seal-forming structure 3100, a plenum chamber 3200, a positioning and stabilising structure 3300, a vent 3400, and a connection port 3600 for connection to air circuit 4170.

In use the seal-forming structure 3100 is arranged to form a seal with a region surrounding an entrance to the airways of the patient so as to maintain positive pressure at the entrance(s) to the airways of the patient 1000. The sealed patient interface 3000 is therefore suitable for delivery of positive pressure therapy. The seal-forming structure 3100 has an opening to allow breathable gas to be delivered to a patient's airways.

The plenum chamber 3200 is a portion of patient interface 3000 having walls at least partially enclosing a volume of space. The plenum chamber 3200 is configured to be pressurisable to therapeutic pressures, for example in the range of 4 to 30 $cmH_2O$ with respect to ambient.

The positioning and stabilising structure 3300 is a structure configured to hold the seal-forming structure 3100 in a therapeutically effective position on the patient's head, e.g. forming a seal with a region surrounding an entrance to the patient's airways.

Connection port 3600 is an opening that allows air circuit 4170 to convey breathable gas to the plenum chamber 3200 for delivery to the patient's airways.

In some forms a functional aspect may be provided by one or more physical components. In some forms, one physical component may provide one or more functional aspects. For example, in certain forms of the technology, the functional aspects of the seal-forming structure 3100 and the plenum chamber 3200 may be provided by a physical component in the form of a cushion module 6100, which may comprise the seal-forming structure 3100 and the plenum chamber 3200.

Further description of the functional aspects and physical component of exemplary forms of the technology will be provided in the ensuing sections.

If a patient interface is unable to comfortably deliver a minimum level of positive pressure to the airways, the patient interface may be unsuitable for respiratory pressure therapy. The patient interface 3000 in accordance with one form of the present technology is constructed and arranged to be able to provide a supply of air at a positive pressure of at least 4 $cmH_2O$ with respect to ambient. The patient interface 3000 in accordance with one form of the present technology is constructed and arranged to be able to provide a supply of air at a positive pressure of at least 10 $cmH_2O$ with respect to ambient. The patient interface 3000 in accordance with one form of the present technology is constructed and arranged to be able to provide a supply of air at a positive pressure of at least 20 $cmH_2O$ with respect to ambient.

4.3.1 Cushion Module

One exemplary form of patient interface 3000 is illustrated in FIGS. 8A-8C, 10A-10B and 11A-11C, another exemplary form of patient interface 3000 is illustrated in FIGS. 9A-9C and 13A-13B, and another exemplary form of patient interface 3000 is illustrated in FIGS. 14A-14D. The patient interface 3000 in these forms of the technology comprises a cushion module 6100. Cushion module 6100 is a physical component that comprises, or an assembly of components that together comprise, the seal-forming structure 3100 and the plenum chamber 3200. In some examples the cushion module 6100 comprises a chassis portion 3211 and the seal-forming structure 3100 together forming the plenum chamber 3200. These functional aspects of the cushion module 6100 will now be described.

4.3.1.1 Seal-Forming Structure

As explained above, in use the seal-forming structure 3100 is arranged to form a seal with a region surrounding an entrance to the airways of the patient so as to maintain positive pressure at the entrance(s) to the airways of the patient 1000.

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In exemplary forms of the technology, the seal-forming structure 3100 forms a physical loop of material around the perimeter of the plenum chamber 3200 that, in use, contacts a closed path on the patient's face around one or more entrances to the patient's airways. The physical loop of material forms an opening 3110 through which the flow of breathable gas is delivered to the patient's airways from the plenum chamber 3200.

In certain forms of the present technology, a patient interface system is provided comprising more than one a seal-forming structure 3100, each being configured to correspond to a different size and/or shape range. For example the system may comprise one form of a seal-forming structure 3100 suitable for a large-sized head, but not a small-sized head and another suitable for a small-sized head, but not a large-sized head. The plurality of seal-forming structures 3100 may differ in size and/or shape. For example, a seal-forming structure 3100 suitable for a large-sized head may form a larger opening 3110 than a seal-forming structure 3100 suitable for a small-sized head. Each of the plurality of seal-forming structure 3100 may be provided to a different cushion module 6100.

In certain forms, the seal-forming structure 3100 may comprise a superior portion 3112 and an inferior portion 3114. The superior portion 3112 of the seal-forming structure 3100 is a part of the seal-forming structure 3100 that is located superiorly to the inferior portion 3114 of the seal-forming structure 3100 when the patient interface 3000 is worn by the patient.

4.3.1.1.1 Sealing Mechanisms

In certain forms of the technology, the seal-forming structure 3100 is constructed and arranged to generally be in compression in use, e.g. as a result of elastic tension in the positioning and stabilising structure 3300 compressing the seal-forming structure 3100 against the patient's face. In some forms, some portions of the seal-forming structure 3100 may nevertheless be held in tension during use, e.g. by adjacent regions.

In the exemplary form of the technology shown in FIGS. 8A-8C, 10A-10B, 11A-11C and 14A-14D, the seal-forming structure 3100 includes a sealing flange 3120 utilizing a pressure-assisted sealing mechanism. In these examples, the seal-forming structure 3100 is attached to and supported by the chassis portion 3211. For example, the sealing flange 3120 may be connected to the chassis portion 3211 and the chassis portion 3211 may support the sealing flange. In use, the sealing flange 3120 can readily respond to a system positive pressure in the interior of the plenum chamber 3200 acting on its underside to urge it into tight sealing engagement with the face. The sealing flange 3120 may be provided to a portion of the edge of the seal-forming structure 3100 and may be configured to extend radially inwardly with respect to the physical loop of the seal-forming structure 3100 so that an inner surface of the sealing flange 3120, i.e. a surface facing away from the patient's face, is in contact with pressurised gas in the plenum chamber 3200. The pressurised gas therefore acts on the inner surface of the sealing flange 3120 and urges the outer surface of the sealing flange 3120 into sealing engagement with the patient's face. In one form, the sealing flange 3120 extends around the entire perimeter of the edge of the seal-forming structure 3100 forming the opening 3110. In another form, the sealing flange 3120 extends around a part of the perimeter of the edge of the seal-forming structure 3100 forming the opening 3110. The pressure-assisted mechanism may act in conjunction with elastic tension in the positioning and stabilising structure 3300.

The seal-forming structure 3100 may, in cross-section, be curved, for example having a C-shaped profile with one end of the 'C' provided to the chassis portion 3211 and the other end of the 'C' forming the sealing flange 3120. An exemplary form of such a seal-forming structure 3100 is shown in FIGS. 6A and 6B. The sealing flange 3120 may be configured so that the end of the 'C' forming the sealing flange 3120 is orientated substantially parallel to the region of the patient's face that it contacts in use. The C-shaped profile of the seal-forming structure 3100 and/or the stated orientation may enable it to act in the manner of a spring in order to provide a cushioning effect against the patient's face, promoting comfort in addition to the pressure-assisted sealing mechanism described above. In certain forms, the end of the 'C' forming the sealing flange 3120 may be thinner than the end of the 'C' provided to the chassis portion 3211. For example, the end of the 'C' provided to the chassis portion 3211 may have a thickness of 2-3 mm and the end of the 'C' forming the sealing flange 3120 may have a thickness of less than 1 mm, for example 0.5 mm.

In another exemplary form of the technology (not illustrated), the seal-forming structure 3100 comprises a sealing flange 3120 and a support flange. The sealing flange 3120 comprises a relatively thin member with a thickness of less than about 1 mm, for example about 0.25 mm to about 0.45 mm, which extends around the perimeter of the plenum chamber 3200. Support flange may be relatively thicker than the sealing flange 3120. The support flange is disposed between the sealing flange 3120 and the marginal edge of the chassis portion 3211, and extends at least part of the way around the perimeter. The support flange is or includes a spring-like element and functions to support the sealing flange 3120 from buckling in use.

4.3.1.1.2 Regions of Sealing

In different forms of the technology, the patient interface 3000 may be configured to form a seal with different regions of a patient's face.

4.3.1.1.2.1 Full Face Mask

In the forms of the technology illustrated in FIGS. 7A-7B, 8A-8C, 9A-9C, 10A-10B, 13A-13B and 14A-14D, the seal-forming structure 3100 of patient interface 3000 is configured to form a seal with the following regions of the patient's face: a nasal bridge (or nose ridge) region; cheek regions on either side of the patient's nose and a chin region (i.e. the region between the patient's inferior lip and the inferior point of the chin). A patient interface 3000 that seals to these regions of a patient's face is typically referred to as a full-face mask. Such a patient interface forms a seal with regions of the patient's face surrounding the patient's nares and mouth, and the pressurised flow of breathable gas is provided through each of these airway entrances.

4.3.1.1.2.2 Nasal Mask

In alternative forms of the technology, the seal-forming structure 3100 of patient interface 3000 is configured to form a seal with the following regions of the patient's face: a nasal bridge (or nose ridge) region; cheek regions on either side of the patient's nose and an upper lip region (i.e. the region between the patient's nose and mouth, which includes the patient's philtrum). A patient interface 3000 that seals to these regions of a patient's face is typically referred to as a nasal mask. Such a patient interface forms a seal with regions of the patient's face surrounding the patient's nares but not the mouth, and the pressurised flow of breathable gas is provided through the nares but not the mouth.

4.3.1.1.2.3 Nasal Bridge or Nose Ridge Region

In certain forms, the patient interface 3000 comprises a seal-forming structure 3100 that forms a seal in use on a nasal bridge region or on a nose-ridge region of the patient's face. The portion of the seal-forming structure 3100 that seals with the nasal bridge region (which may be referred to as the nasal bridge portion of the seal-forming structure 3100) may be saddle-shaped to promote a sealed contact.

The nasal bridge region of a patient's face is typically sensitive and is easily abraded and marked by contact with a patient interface device. In certain forms of the technology, the nasal bridge portion of seal-forming structure 3100 is thinner than other portions of the seal-forming structure in order to reduce the amount of force imparted on the nasal bridge region of the patient's face when the patient interface 3000 is in use, as compared to other regions. In certain forms, the seal-forming structure 3100 may be approximately 0.3-0.5 mm thick in the nasal bridge portion, for example.

4.3.1.1.2.4 Cheek Region

In certain forms, the patient interface 3000 comprises a seal-forming structure 3100 that forms a seal in use with cheek regions on either side of the patient's nose.

In a full-face mask, the portions of the seal-forming structure 3100 that seals with the cheek regions (which may be referred to as the cheek portions of the seal-forming structure 3100) is longer than the cheek portions of a nasal mask that would be suitable for a patient of similar size.

In certain forms, the cheek portions of the seal-forming structure 3100 may be saddle-shaped to promote a sealed contact with the patient's face. For example, a full-face mask may comprise saddle-shaped cheek portions of the seal-forming structure 31000. In other forms, the cheek portions of the seal-forming structure 3100 may have a negative curvature in one direction and an approximately zero curvature in a perpendicular direction. For example, a nasal mask may comprise cheek portions shaped in this manner.

The cheek regions of the patient's face are typically less sensitive than, for example, the nasal bridge region. Therefore, the cheek portions of the seal-forming structure 3100 may be relatively thick compared to the nasal bridge portions of the patient interface 3000, for example approximately 2-3 mm thick.

4.3.1.1.2.5 Chin-Region

In forms of the technology in which the patient interface 3000 is a full-face mask, the seal-forming structure 3100 comprises a chin portion that forms a seal in use on a chin-region of the patient's face. In certain forms, the chin portion may comprise a saddle-shaped region to promote a sealed contact.

In certain forms of the technology, the chin portion of seal-forming structure 3100 is thinner than other portions of the seal-forming structure in order to reduce the amount of force imparted on the chin region of the patient's face when the patient interface 3000 is in use, as compared to other regions. This may be beneficial to reduce the backward loading on the jaw, compared to if the force imparted on the jaw was higher, which may lead to increased airway obstruction. A relatively thin region also promotes flex of the chin portion of the seal-forming structure 3100 if the patient's mouth opens and closes (or otherwise moves), which assists in maintaining a sealed contact with the chin region. In certain forms, the seal-forming structure 3100 may be approximately 0.3-0.5 mm thick in the chin portion, for example.

4.3.1.1.2.6 Upper Lip Region

In forms of the technology in which the patient interface 3000 is a nasal mask, the seal-forming structure 3100 comprises an upper lip portion that forms a seal in use on an upper lip region of the patient's face. In certain forms, the upper lip portion may comprise a saddle-shaped region to promote a sealed contact.

In certain forms of the technology, the upper lip portion of seal-forming structure 3100 may be thinner than other portions of the seal-forming structure in order to reduce the amount of force imparted on the upper lip region of the patient's face when the patient interface 3000 is in use, as compared to other regions. This may be beneficial as the upper lip region may be more sensitive to prolonged contact with a patient interface than some other regions of the patient's face. In certain forms, the seal-forming structure 3100 may be approximately 0.3-0.5 mm thick in the upper lip portion, for example.

4.3.1.1.3 Materials

In certain forms of the present technology, the seal-forming structure 3100 is constructed from a biocompatible material. A seal-forming structure 3100 in accordance with the present technology may additionally or alternatively be constructed from a soft, flexible, resilient material. Suitable materials that may be used to form the seal-forming structure 3100 in certain forms of the technology include elastomers, e.g. silicone (e.g. liquid silicone rubber (LSR)) and foams. For example, the seal-forming structure 3100 in the exemplary forms of the technology illustrated in FIGS. 8A-8C, 10A-10B and 14A-14D is formed from LSR and the seal-forming structure 3100 in the exemplary form of the technology illustrated in FIGS. 9A-9C and 13A is formed from foam.

In the example of FIGS. 9A-9C and 13A, the foam seal-forming structure 3100 may have a thickness in the range of approximately 5-40 mm. The thickness of the seal-forming structure 3100 may be constant around the perimeter of the opening that delivers breathable gas to the patient's airways. Alternatively, the thickness may vary around the perimeter so as to vary the compression force in different regions depending on the sensitivity of the facial region.

In one exemplary form of the technology, the seal-forming structure 3100 is formed from an LSR having a hardness of approximately 20-50 Shore A, for example approximately 40 Shore A. A higher hardness value may improve the rigidity of the seal-forming structure 3100 while a lower hardness may improve the level of comfort.

4.3.1.2 Plenum Chamber and Chassis Portion

As explained above, the plenum chamber 3200 is a portion of patient interface 3000 having walls at least partially enclosing a volume of space. The plenum chamber 3200 is configured to be pressurisable to therapeutic pressures, for example in the range of 4 to 30 $cmH_2O$ with respect to ambient. A cushion module 6100 may comprise walls forming the plenum chamber 3200. In some forms of the present technology the plenum chamber 3200 is at least partially formed by a chassis portion 3211 of the cushion module 6100 and at least partially formed by the seal-forming structure 3100. In some forms of the technology the chassis portion 3211 may be identified as the plenum chamber 3200, especially in examples of the technology in which the chassis portion 3211 defines a significant portion, or a majority, of the volume of the plenum chamber 3200.

The chassis portion 3211 or plenum chamber 3200 may have a perimeter that is shaped to be complementary to the surface contour of the face of an average person in the region where a seal will form in use. Alternatively, the chassis portion 3211 may have a perimeter that is shaped to be complementary to the surface contour of the face of an actual person in the region where a seal will form in use, i.e. the chassis portion 3211 may be customised to an individual patient. In use, a marginal edge of the chassis portion 3211 is positioned in close proximity to an adjacent surface of the face. Actual contact with the face is provided by the seal-forming structure 3100, which is provided to the chassis portion 3211. The seal-forming structure 3100 may extend in use about the entire perimeter of the plenum chamber 3200. The seal-forming structure 3100 may be overmoulded to the chassis portion 3211 or may be otherwise attached, such as by gluing or a mechanical connection (e.g. a press fit or snap fit).

4.3.1.2.1 Flexibility

In certain forms of the technology, the chassis portion 3211 is configured to be substantially flexible. That is, the structure of the chassis portion 3211 and the material from which the chassis portion 3211 is formed are such that the chassis portion 3211 is able to be deformed. In certain forms, all of the chassis portion 3211 is substantially flexible while in other forms a significant proportion of the chassis portion 3211 is substantially flexible.

Flexibility in the chassis portion 3211 may be advantageous in allowing some movement when the cushion module 6100 is placed against the patient's face in use. The seal-forming structure 3100 may form or be located on a posterior side of the cushion module 6100, and may provide flexibility to adapt to the contours of the patient's face, but flexibility in the anterior side of the cushion module 6100, for example in the chassis portion 3211 may provide additional adaptability to help ensure a sealing contact with a wide range of facial geometries. Furthermore, a flexible chassis portion 3211 may serve to dampen forces acting on the headgear, which may lessen the effect of the forces on the patient's face, which could cause discomfort or disrupt the seal between the seal-forming structure 3100 and the patient's face.

In certain exemplary forms of the technology, the flexibility of the chassis portion 3211 is achieved by forming the chassis portion 3211 from a reasonably soft material and with reasonably thin (for example a thickness of 5 mm or less) walls.

The structure of the chassis portion 3211 and/or the material it is made from may also be selected so that the chassis portion 3211 resiliently returns to its original shape, or approximately its original shape, when a deformation force is removed. For example, the chassis portion 3211 may be formed from an elastic material such as silicone. In other forms, the chassis portion 3211 may be formed to be non-resilient (e.g. non-elastically deformable) but may be mounted in use to another component (e.g. a seal-forming structure 3100) that is configured to resiliently return to its original shape, or approximately its original shape.

In certain forms of the present technology, the chassis portion 3211 is constructed from a biocompatible material.

Suitable materials that may be used to form the chassis portion 3211 in certain forms of the technology include elastomers, e.g. silicone (e.g. liquid silicone rubber (LSR)) and fabric.

In the exemplary form of the technology illustrated in FIGS. 8A-8C, 10A-10B and 14A-14D, the chassis portion 3211 is formed from an elastomeric material, such as TPE or LSR in particular examples. For example, the chassis portion 3211 may be formed from an LSR having a hardness of approximately 20-50 Shore A, for example approximately 40 Shore A. A higher hardness value may increase the rigidity of the chassis portion 3211.

In some forms of the technology, the cushion module 6100 comprising the chassis portion 3211 and the seal-forming structure 3100, and forming a plenum chamber 3200, may be formed from a single homogeneous piece of material. For example, in the forms illustrated in FIGS. 8A-8C, 10A-10B and 14A-14D, the cushion module 6100 is formed from a single piece of LSR. In such forms, the cushion module 6100 may be formed in a single moulding process, for example injection moulding, so that the chassis portion 3211 and the seal-forming structure 3100 are integrally moulded together. This may save time and cost during the manufacturing process. In other forms, the chassis portion 3211 and the seal-forming structure 3100 may both be formed from an elastomer, e.g. LSR, but have different hardnesses. For example, the chassis portion 3211 and the seal-forming structure 3100 may be co-moulded to form the cushion module 6100.

In the exemplary form of the technology illustrated in FIGS. 9A-9C and 13A, the chassis portion 3211 is formed from a fabric. In certain forms, the fabric may be impermeable to breathable gas to prevent the leakage of gas from the plenum chamber 3200 other than through desired or expected leak paths, e.g. the vent 3400 or through imperfect sealing contact of the seal-forming structure 3100 with the patient's face. In some such forms, an otherwise permeable fabric may be rendered impermeable by being treated (e.g. coated) with an impermeable material. In some examples, the chassis portion 3211 may be formed from a foam/polyester laminate material, for example of the type used in headgear straps on some CPAP masks. In other examples polyester or nylon backed with silicone or a thermo-plastic elastomer (TPE) may be used.

In other forms, a permeable fabric may be used and the permeability of the fabric may be used to allow for the washout of exhaled gases from the plenum chamber 3200. For example, the fabric may contain a plurality of pores that together act as a vent 3400 to allow for gas washout.

In the form of the technology illustrated in FIGS. 9A-9C and 13A, the foam seal-forming structure 3100 may be thermoformed or glued to the fabric chassis portion 3211.

4.3.1.2.2 Relative Movement of Superior and Inferior Portions

In certain forms of the technology, the anterior side of the cushion module 6100 and plenum chamber 3200 (e.g. the chassis portion 3211) may be configured in a manner that allows a first portion 3212 of the chassis portion 3211 to move relative to a second portion 3214 of the chassis portion 3211, where the first portion is a portion configured to be located superiorly to the second portion when the patient interface 3000 is worn by the patient. Consequently, the first portion will be referred to as the superior portion 3212 and the second portion will be referred to as the inferior portion 3214. The configuration of the chassis portion 3211 in these forms of the technology allows an orientation of a superior portion 3112 of the seal-forming structure 3100 to adjust relative to an orientation of an inferior portion 3114 of the seal-forming structure 3100. The superior portion 3112 of the seal-forming structure 3100 is a part of the seal-forming structure 3100 that is located superiorly to the inferior portion 3114 of the seal-forming structure 3100 when the patient interface 3000 is worn by the patient.

It will be appreciated that the relative movement referred to above means that, in practice, one of the portions may remain stationary while the other portion moves or both portions may move with one moving relative to the other.

In certain forms of the technology, the relative movement between the superior portion 3212 and the inferior portion 3214 of the chassis portion 3211 is a rotation. That is, the plenum chamber 3200 is configured so that the superior portion 3212 is able to rotate relative to the inferior portion 3214.

FIGS. 7A and 7B illustrate an exemplary cushion module 6100 according to one form of the technology in which the superior portion 3212 of the chassis portion 3211 rotates relative to the inferior portion 3214 around axis of rotation A. FIG. 7B illustrates the cushion module 6100 in a first configuration in which the superior portion 3112 of the seal-forming structure 3100 that is provided to the superior portion 3212 of the chassis portion 3211 and the inferior portion 3114 of the seal-forming structure 3100 that is provided to the inferior portion 3214 of the chassis portion 3211 are in a first relative position. FIG. 7A illustrates the cushion module 6100 in a second configuration in which the superior portion 3112 and the inferior portion 3114 are in a second relative position. The angle between the superior portion 3112 and the inferior portion 3114 is greater in the second configuration than in than first configuration when the cushion module 6100 is viewed from a direction perpendicular to a sagittal plane of the patient, as in FIGS. 7A and 7B.

It should be appreciated that the superior portion 3112 of the seal-forming structure 3100 and the inferior portion 3114 of the seal-forming structure 3100 form complex shapes which do not define a single angle relative to each other. Furthermore, the shape of the superior portion 3112 and the inferior portion 3114 may change between the first and second configurations. When it is described that the angle between the superior portion 3112 and the inferior portion 3114 changes between the first and second configurations, this means, in some forms of the technology, that the angle between any two given portions of the superior portion 3112 and the inferior portion 3114, when viewed in a direction perpendicular to a sagittal plane, changes between the first and second configurations.

The angle between the superior portion 3112 and the inferior portion 3114 of the seal-forming structure 3100 may, in some forms, be defined as the angle between the region of the superior portion 3112 that contacts the patient's nasal bridge in use and the region of the inferior portion 3114 that contacts the patient's medial chin region when viewed from a direction perpendicular to a sagittal plane in use. That is, the angle between a superior-most portion of the seal-forming structure 3100 lying in the mid-sagittal plane in use and an inferior-most portion of the seal-forming structure 3100 lying in the mid-sagittal plane in use, where that angle is one viewed from, or projected onto, a plane oriented parallel to the mid-sagittal plane when the patient interface 3000 is being worn. An example of this angle is shown as θ in FIG. 7A.

The range of movement permitted between the superior portion 3212 and the inferior portion 3214 of the chassis portion 3211 may, in some forms of the technology, allow the angle θ to vary between approximately 100 and approximately 45°, for example approximately 20° and approximately 35°.

The relative movement between the superior portion 3212 and the inferior portion 3214 of the chassis portion 3211 enables the shape of the cushion module 6100 to be tailored for different patients with different facial geometries. For example, for a patient with a relatively flat facial profile (for example, having a shallow nasal bridge angle and/or a prominent chin), the chassis portion 3211 may adopt a configuration in which the angle between the superior portion 3112 and the inferior portion 3114 is relatively small, such as is shown in FIG. 7B. For a patient with a relatively steep facial profile (for example, having a steep nasal bridge angle and/or a 'weak chin'), the chassis portion 3211 may adopt a configuration in which the angle between the superior portion 3112 and the inferior portion 3114 is relatively large, such as is shown in FIG. 7A. The ability of the chassis portion 3211 to adopt different configurations for patients with different facial geometries may be beneficial to help with comfort and the quality of seal. FIGS. 6A and 6B illustrate a sealing flange 3120 of a seal-forming structure 3100 contacting a nasal bridge region of a patient's face in two different orientations of the superior portion 3212 of the chassis portion 3211. The end of the sealing flange 3120 is more parallel to the surface of the patient's nasal bridge region in FIG. 6A compared to FIG. 6B where there is a greater angle between the end of the sealing flange 3120 and the surface of the patient's nasal bridge region it comes into contact with, thus meaning only the tip (or edge) of the sealing flange 3120 may contact the skin in use in the configuration shown in FIG. 6B. Consequently, a greater surface of the sealing flange 3120 may come into contact with the nasal bridge region of the patient's nose in the configuration of the chassis portion 3211 in FIG. 6A compared to FIG. 6B. This is beneficial in spreading out the force exerted by the seal-forming structure 3100 on the patient's nasal bridge region, which will improve comfort in this sensitive area. This may particularly be the case in forms of the technology in which the positioning and stabilising structure 3300 comprises a single strap 3310 (as described below) where the strap 3310 may tend to pull the cushion module 6100 in an inferior direction relative to the patient. As well as being more comfortable, there may be a reduced chance of damage to the patient's skin and the cushion may be more durable.

In use, the force that causes the cushion module 6100 to flex (in order to change the orientation between the superior portion 3212 and the inferior portion 3214 of the chassis portion 3211) may be provided by the positioning and stabilising structure 3300, for example by a strap 3310 of the positioning and stabilising structure 3300 of the type described below.

The cushion module 6100 may be configured so that the chassis portion 3211 has a 'natural' configuration (i.e. the configuration adopted by the chassis portion 3211 in the absence of forces acting upon it) in which there is a particular angle between the superior portion 3212 and the inferior portion 3214. In certain forms, the natural configuration may be one in which there is a relatively large angle between the superior portion 3212 and the inferior portion 3214, for example the configuration shown in FIG. 7A. When the patient interface 3000 is donned, in certain forms of the technology, a strap 3310 of a positioning and stabilising structure 3300 is placed across the anterior side of the chassis portion 3211 and tension is applied to the strap, causing the strap 3310 to urge the middle region of the chassis portion 3211 (with respect to the height H of the chassis portion 3211) towards the patient's face, thus reducing the angle between the superior portion 3212 and the inferior portion 3214 until the forces are in equilibrium and the seal-forming structure 3100 is in sealing engagement with the patient's face. A benefit of the natural configuration being one in which there is a relatively large angle between the superior portion 3212 and the inferior portion 3214 is that the strap 3310 of the positioning and stabilising structure 3100 only needs to apply a force to the chassis portion 3211 in the middle region proximate the axis of rotation A. In contrast, in forms of the present technology where the natural configuration is one in which there is a relatively small angle between the superior portion 3212 and the inferior portion 3214, forces may need to be applied in two locations, both superior and inferior to the axis of rotation A in order to urge the seal-forming structure 3100 into sealing engagement with the patient's face.

In the exemplary form of the technology shown in FIGS. 7A and 7B, the superior portion 3212 of the chassis portion 3211 extends superiorly from approximately a midpoint with respect to a height of the chassis portion 3211 when the cushion module 6100 is in its 'in use' orientation. The height of the chassis portion 3211 may be considered to be the extent of the chassis portion 3211 in a direction perpendicular to the Frankfort horizontal plane of the patient when the patient interface 3000 is worn in the intended position in use, i.e. distance H shown in FIGS. 7A and 7B.

Similarly, the inferior portion 3214 of the chassis portion 3211 extends inferiorly from approximately a midpoint with respect to a height of the chassis portion 3211 when the cushion module 6100 is in its 'in use' orientation. (Similarly the superior portion 3112 of the seal-forming structure 3100 may extend superiorly from approximately a midpoint with respect to a height of the seal-forming structure 3100 when the cushion module 6100 is in its 'in use' orientation, and the inferior portion 3114 of the seal-forming structure 3100 extends inferiorly from approximately a midpoint with respect to a height of the seal-forming structure 3100 when the cushion module 6100 is in its 'in use' orientation.)

In some forms of the technology, an axis of rotation around which the superior portion 3212 rotates relative to the inferior portion 3214 may be positioned between the superior portion 3212 and inferior portion 3214 of the chassis portion 3211, for example in a region separating the superior portion 3212 from the inferior portion 3214. In certain forms of the technology, the axis of rotation may be positioned at approximately a midpoint of the height of the chassis portion 3211. For example, in the form of the technology illustrated in FIGS. 7A and 7B, the axis of rotation is marked approximately as A and it extends into and out of the page. In certain forms of the technology, including the form illustrated in FIGS. 7A and 7B, the axis of rotation A is oriented perpendicular to a sagittal plane of the patient when the patent interface 3000 is worn in use.

In other forms of the technology, the superior portion 3212 and inferior portion 3214 of the chassis portion 3211 may have different extents of the height of the chassis portion 3211. For example, the axis of rotation A may be positioned closer to the superior-most portion of the chassis portion 3211 when the cushion module 6100 is in its in-use orientation than to the inferior-most portion of the chassis portion 3211. Alternatively, the axis of rotation A may be positioned closer to the inferior-most portion of the chassis portion 3211 when the cushion module 6100 is in its in use orientation than to the superior-most portion of the chassis portion 3211.

4.3.1.2.3 Flex Region

In the form of the technology illustrated in FIGS. 7A and 7B, the relative movement of the superior portion 3212 and inferior portion 3214 of the chassis portion 3211 is achieved by the chassis portion 3211 comprising a flex region 3210 having greater flexibility than other regions of the chassis portion 3211. The flex region 3210 enables the superior portion 3212 of the chassis portion 3211 to move relative to the inferior portion 3214 of the chassis portion 3211 in the manner described above. In some forms, the flex region 3210 may act as a hinge for the superior portion 3212 to rotate relative to the inferior portion 3214.

The flex region 3210 may be located in a portion of the chassis portion 3211 between the superior portion 3212 and the inferior portion 3214. For example, the flex region 3210 may be located in a middle region with respect to the height H of the chassis portion 3211.

In some exemplary forms of the technology, the flex region 3210 is located in a portion of the chassis portion 3211 so that, when the patient interface 3000 is worn, the flex region is approximately level with the patient's cheek bones. The cheek bones may provide a firm structural part of the patient's face around which the superior and inferior portions of the seal-forming structure 3100 can flex around, which helps the patient interface 3000 to be held in a stable manner on the face.

In certain forms, the flex region 3210 extends across substantially the width of the chassis portion 3211. The width of the chassis portion 3211 may be considered to be an extent of the chassis portion 3211 in a direction perpendicular to a sagittal plane of the patient when the patient interface 3000 is in the intended position and orientation in use. That is, the flex region 3210 may extend from a first lateral edge of the chassis portion 3211 on one side of the patient interface 3000, or proximate a first lateral edge of the chassis portion 3211 on one side of the patient interface 3000, to a second lateral edge of the chassis portion 3211 on the other side of the patient interface 3000, or proximate a second lateral edge of the chassis portion 3211 on the other side of the patient interface 3000.

In certain forms, the flex region 3210 may extend into a part of the seal-forming structure 3100 proximate the chassis portion 3211. That is, a part of the seal-forming structure 3100 proximate the chassis portion 3211 may also comprise a flex region. It may be advantageous for the flex region 3210 to not extend into a part of the seal-forming structure 3100 that, in use, actually contacts the patient's face. If it were to, then the seal between the seal-forming structure 3100 and the patient's face may be broken if the flex region 3210 flexes in use.

In the form of the technology shown in FIGS. 7A and 7B, the flex region 3210 is lens-shaped. That is, the tallest portion of the flex region 3210 is on the anterior side of the chassis portion 3211 in a medial location facing away from the patient in use and this tapers towards short portions of the flex region 3210 on the lateral sides of the chassis portion 3211. In the side view (i.e. view in a direction perpendicular to a sagittal plane), the lens-shaped flex region 3210 appears wedge-shaped, as shown in the figures. In other forms of the technology, the flex region 3210 has a different shape. For example, the boundary of the flex region 3210 closest to the seal-forming structure 3100, which may be the boundary of the short portions of the flex region 3210 on the lateral sides of the chassis portion 3211, or the posterior-most portion of the flex region 3210 when the patient interface 3000 is being worn, may comprise one or more rounded corners instead of the sharp point shown in some of the figures.

In certain forms, the chassis portion 3211 may comprise a plurality of flex regions 3210. For example, the chassis portion 3211 may comprise a first flex region on one lateral side and a second flex region on a second lateral side. In some forms, there may be additional flex regions arranged across the width of the chassis portion 3211.

In different forms of the technology, the greater flexibility of the flex region 3210 compared to other regions of the chassis portion 3211 may be provided in different ways. In certain forms, the material forming the flex region 3210 has a lesser thickness than material forming other regions of the chassis portion 3211. For example, in the forms shown in FIGS. 8A-8C, the flex region 3210 is made of LSR having a thickness of approximately 0.3-1 mm and the adjacent regions of the chassis portion 3211 are made of the same material with a thickness of approximately 2-3 mm.

In other forms of the technology, the flex region 3210 may comprise one or more folds configured to assist the flex region to fold or collapse in order to allow the superior portion 3212 and inferior portion 3214 to move relative to each other. For example, the flex region 3210 may comprise a series of folds in a concertina or bellows structure.

Alternatively, one part of the flex region 3210 may be configured to roll over another part of the flex region 3210, or another part of the chassis portion 3211.

In the exemplary form of the technology shown in FIGS. 14A-14D, the flex region 3210 comprises a recessed region 3230. The recessed region 3230 is recessed compared to adjacent parts of the chassis portion 3211. The recessed region 3230 extends laterally across the chassis portion 3211 from a point on one lateral side proximate the seal-forming structure 3100, around the anterior side of the chassis portion 3211, to an equivalent point on the other lateral side. Gradient minimums along the recessed region 3230 (i.e. the points of greatest recess along the width of the recessed region 3230) may form a space curve that is oriented generally parallel to, or at a small acute angle to, the Frankfort horizontal when the patient interface 3000 is being worn. The recessed region 3230 may have a height in the superior-inferior direction (with reference to when the patient interface 3000 is worn) that is shorter than the length of the recessed region 3230 in the lateral direction, for example significantly shorter as shown in FIG. 14A-14D. The recessed region 3230 provides the flex region 3210 with greater flexibility than adjacent regions of the chassis portion 3211 because it provides a natural fold or collapse point. That is, when the cushion module 6100 is placed against a patient's face, the superior and inferior portions are able to rotate through the folding, or collapse, of the recessed region 3230.

In other forms, the flex region 3210 may comprise a protruded region instead of, or in addition to, a recessed region such as that shown in FIGS. 14A-14D. A protruded region may provide flexibility through outward folding/collapse rather than inward folding/collapse as in the case of recessed region 3230.

In the form of the technology shown in FIGS. 14A-14D, the recessed region 3230 is bounded by rounded edges to transition the walls of the chassis portion 3211 into the recessed region 3230. In other forms, these edges may be angular, e.g. sharp changes in gradient of the walls of the chassis portion 3211 between the recessed region 3230 and an adjacent region of the chassis portion 3211.

In an alternative form of the technology, the flex region 3210 may comprise one or more slits or cut-outs to facilitate flexibility in the flex region 3210. For example, in the form of the technology shown in FIGS. 9A-9C, the chassis portion 3211 is formed from a fabric. There is a slit 3220 in the chassis portion 3211 which forms a superior portion 3212 of the chassis portion 3211 above the slit 3220 and an inferior portion 3214 of the chassis portion 3211 below the slit 3220.

In the illustrated form, the slit extends across at least a part of the width of the chassis portion 3211. In one form the slit may have the shape of a space curve lying in a plane that is parallel to the Frankfort horizontal of the patient when the patient interface 3000 is worn. In other forms, the space curve may lie in a plane at a relatively small angle to the Frankfort horizontal of the patient when the patient interface 3000 is worn. In other forms, the slit may have a different shape.

In the illustrated form, the slit spans across most of the width of the chassis portion 3211 but does not extend to the lateral edges of the chassis portion 3211.

In the form of the technology shown in FIGS. 9A-9C, the chassis portion 3211 comprises a gusset 3225. The gusset 3225 is attached to the main body of the chassis portion 3211 all around the slit 3220 and spans across the slit 3220. The gusset 3225 is sealingly attached to the main body of the chassis portion 3211 so that gas does not leak out of the chassis portion 3211 around the attachment region. For example, the gusset 3225 may be glued or heat sealed to the main body of the chassis portion 3211. The gusset 3225 is formed from a sheet of material that is sufficiently large that it allows the superior portion 3212 of the chassis portion 3211 to move relative to the inferior portion 324 to expand the slit 3220 before the gusset 3225 is pulled taut and prevents further extension between the superior and inferior portions.

The gusset 3225 may be formed from the same material as the main body of chassis portion 3211, for example the same fabric. Alternatively, the gusset 3225 may be formed from a different material as the main body of chassis portion 3211. In certain forms, the gusset 3225 is formed from a gas impermeable material or fabric. In other forms, the gusset 3225 is formed from a gas permeable material, for example a porous fabric, in order to allow for some washout of exhaled gases from the chassis portion 3211 during use.

In other forms of the technology, a number of different mechanisms may be used in combination to make the flex region 3210 more flexible than other regions of the chassis portion 3211. For example, the flex region 3210 in the form of the technology shown in FIGS. 14A-14D may be formed of a material having a lesser thickness than other regions of the chassis portion 3211 in addition to the flex region being able to fold as explained above.

A property of the flex region 3210 may be varied in different forms of the technology in order to vary the force required to urge the chassis portion 3211 away from its natural configuration, i.e. the stiffness of flexibility of the flex region 3210. A suitable property to vary depends on the nature of the flex region 3210. In the case of a flex region having a lesser thickness than other regions of the plenum chamber, the stiffness can be varied by altering the thickness of the flex region 3210, i.e. a thicker flex region 3210 will flex more stiffly. In other forms, the configuration of the folds may be varied to alter the stiffness. In other forms, the stiffness may be altered be adjusting other properties of the cushion module 6100, for example the stiffness of the design of the chassis portion 3211 (e.g. using a harder material or a stiffer shape/configuration).

4.3.1.2.4 Anterior Side of Plenum Chamber

In certain forms of the technology, the anterior side of the chassis portion 3211 faces away from the patient when the patient interface 3000 is worn and is on an opposite side of the cushion module 6100 to the target seal-forming region of the seal-forming structure 3100.

The anterior side of the chassis portion 3211 may comprise a superior anterior portion, for example an anterior portion of superior portion 3212. In exemplary forms, the chassis portion 3211 may be configured so that the superior portion 3212 overlays the patient's nose when the patient interface 3000 is worn. The inner surface of the superior portion 3212 is sufficiently positively curved that the inner surface of the superior portion 3212 does not contact the patient's nose when the patient interface 3000 is worn, including when the chassis portion 3211 is under compression from a force applied by the positioning and stabilising structure 3300. In other forms, where another part of the chassis portion 3211 overlays the patient's nose when the patient interface 3000 is worn, the inner surface of that other part is sufficiently positively curved that the inner surface of the chassis portion 3211 does not contact the patient's nose when the patient interface 3000 is worn, including when the chassis portion 3211 is under compression from a force applied by the positioning and stabilising structure 3300.

The anterior side of the chassis portion 3211 may comprise an inferior anterior portion, for example an anterior portion of inferior portion 3214. In exemplary forms, the chassis portion 3211 may be configured so that the inferior portion 3212 overlays the patient's mouth when the patient interface 3000 is worn. The inner surface of the inferior portion 3214 is sufficiently positively curved that the inner surface of the inferior portion 3214 does not contact the patient's mouth when the patient interface 3000 is worn, including when the chassis portion 3211 is under compression from a force applied by the positioning and stabilising structure 3300. In other forms, where another part of the chassis portion 3211 overlays the patient's mouth when the patient interface 3000 is worn, the inner surface of that other part is sufficiently positively curved that the inner surface of the chassis portion 3211 does not contact the patient's mouth when the patient interface 3000 is worn, including when the chassis portion 3211 is under compression from a force applied by the positioning and stabilising structure 3300.

In certain forms of the technology, an inferior portion of the anterior side of the chassis portion 3211 has a plenum chamber inlet port 3205 formed therein. The plenum chamber inlet port 3205 is described in more detail below.

The anterior side of the chassis portion 3211 may be shaped and structured in a manner that allows connection with the positioning and stabilising structure 3300, for example a strap 3310 of the positioning and stabilising structure 3300 of the type described below. In certain forms of the technology, the connection with the strap 3310 is in the form of a mating of parts, or an alignment of sympathetically shaped parts. For example, the anterior side of the chassis portion 3211 (i.e. the side of the chassis portion 3211 facing away from the patient in use) may comprise one or more recesses in regions configured to align with projections on the side of the strap 3310 facing towards the patient in use, for example support members of the type described in more detail below. In the form of the technology shown in FIG. 8B, the anterior portion of the chassis portion 3211 comprises a region having an abrupt change in angle between adjacent portions when viewed in side cross-section (i.e. from a direction perpendicular to the mid-sagittal plane when worn), creating a pointy feature on the anterior side of the chassis portion 3211. This may create a surface against which a strap 3310 of a positioning and stabilising structure 3300 such as described below may exert a retention force. Alternatively, the cushion module 6100 may be held in place during use through the frictional contact with the strap 3310 which applies a retention force to the cushion module 6100 alone, with any additional retention mechanism such as interlocks.

In exemplary forms of the technology in which the chassis portion 3211 is formed from LSR (for example in the form of the technology illustrated in FIGS. 8A-8C, 10A-10B and 14A-14D), the anterior side of the chassis portion 3211 may have a thickness of approximately 1-4 mm, for example 2-3 mm.

4.3.1.2.5 Plenum Chamber Inlet Port

In certain forms of the technology, the cushion module 6100 has formed therein a plenum chamber inlet port 3205 configured to receive a flow of breathable gas for breathing by the patient. The plenum chamber inlet portion 3205 may be formed in the chassis portion 3211 of the cushion module 6100, for example. The flow of gas may be received from an inlet conduit, for example an elbow 4700. The inlet conduit may form part of air circuit 4170 or may be configured to connect to air circuit 4170.

In the forms of the technology illustrated in FIGS. 8A-8C, 9A-9C, 10A-10B, 13A and 14A-14D, the plenum chamber inlet port 3205 is located on an anterior side of the cushion module 6100 when the patient interface 3000 is being worn. For example, the plenum chamber inlet port 3205 may be located in an inferior region of the chassis portion 3211, for example inferior portion 3214. The plenum chamber inlet port 3205 may be located so that it is positioned generally in front of an entrance to the patient's airways when the patient interface 3000 is worn.

In certain forms the plenum chamber inlet port 3205 is configured so that the inlet conduit fluidly connects to the plenum chamber inlet port 3205 in a fluidly sealed manner, for example with an interference fit. For example, the diameter of the plenum chamber inlet port 3205 may be equal to, or slightly smaller than the diameter of the inlet conduit to ensure an airtight fit. In certain forms, a gasket, for example O-ring 3207, may be provided to the plenum chamber inlet port 3205 to help achieve a sealed connection to the inlet conduit. An O-ring 3207 may be particularly useful in the case of the form of the technology shown in FIGS. 9A-9C and 13A, where the main body of chassis portion 3211 is formed of a fabric that may not adequately fluidly seal to an inlet conduit on its own.

4.3.1.3 Vent

In certain forms of the technology, the patient interface 3000 includes a vent 3400 constructed and arranged to allow for the washout of exhaled gases, e.g. carbon dioxide, from the plenum chamber 3200.

In certain forms the vent 3400 is configured to allow a continuous vent flow from an interior of the plenum chamber 3200 to ambient whilst the pressure within the plenum chamber is positive with respect to ambient. The vent 3400 may be configured such that the vent flow rate has a magnitude sufficient to reduce rebreathing of exhaled $CO_2$ by the patient while maintaining the therapeutic pressure in the plenum chamber in use.

In certain forms, the vent 3400 may be provided to the cushion module 6100, for example comprised as part of chassis portion 3211. For example, the vent 3400 may be located in an anterior surface of the plenum chamber.

In certain forms, the vent 3400 takes the form of a plurality of through-holes in a surface of the plenum chamber, for example, about 20 to about 80 holes, or about 40 to about 60 holes, or about 45 to about 55 holes.

In other forms, such as the form illustrated in FIGS. 9A-9C and 13A-13B, the vent 3400 takes the form of a plurality of pores in the material forming chassis portion 3211.

In other forms, the vent 3400 may be located in another part of the patient interface 3000 or respiratory therapy system, such as the inlet conduit or elbow, as described further by way of example below.

4.3.2 Positioning and Stabilising Structure

The seal-forming structure 3100 of the patient interface 3000 of the present technology may be held in a therapeutically effective position on the patient's head in use, e.g. in a position in which the seal-forming structure 3100 is sealed against the patient's face, by the positioning and stabilising structure 3300.

In certain forms the positioning and stabilising structure 3300 provides a retention force at least sufficient to overcome the effect of the positive pressure in the plenum chamber 3200 to lift off the face.

In certain forms the positioning and stabilising structure 3300 provides a retention force to overcome the effect of the gravitational force on the patient interface 3000.

In certain forms the positioning and stabilising structure 3300 provides a retention force in excess of the minimum retention force that may be required to maintain the seal-forming structure 3100 in position as a safety margin to overcome the potential effect of disrupting forces on the patient interface 3000, such as from tube drag, or accidental interference with the patient interface.

4.3.2.1 Single Strap

In certain forms of the technology, the positioning and stabilising structure 3300 comprises a strap 3310. The strap 3310 may be flat, i.e. relatively thin compared to its length and height, and may also be bendable and non-rigid, so that it can be worn comfortably when the patient is sleeping, including lying on the strap 3310.

The strap 3310 is configured to be arranged, in use, so that the strap 3310 overlies the cushion module 6100 and passes around the back of the patient's head. When worn, the strap 3310 is under tension to apply a retention force on the cushion module 6100 towards the patient's face, e.g. in a generally posterior direction, in order to hold the cushion module 6100 in an operative position.

More specifically, when worn, the strap 3310 encircles the patient's head and neck. The strap 3310 consequently has an anterior portion positioned on an anterior side of the patient's head and overlying an anterior surface of the cushion module 6100, e.g. an anterior surface of the plenum chamber 3200 and, in some examples, an anterior surface of the chassis portion 3211 of the cushion module 6100. The strap 3310 further has a posterior portion positioned on a posterior side of the patient's head and overlying the posterior of the patient's head, for example the patient's neck. The strap 3310 further has lateral portions that are positioned on the sides of the patient's head and overlie the sides of the patient's head. The anterior, posterior and lateral portions of the strap 3310 are connected together in a loop when worn. In particular, the chassis portion 3211 of the cushion module 6100 may have a width in a direction perpendicular to a sagittal plane of the patient when the patient interface 3000 is worn in use, and the anterior portion of the strap 3310 may overlie an anterior surface of the chassis portion 3211 across the width of the chassis portion 3311. In certain forms, a continuous length of the strap 3310 overlies the width of the anterior side of the chassis portion 3211, i.e. there are no full breaks (e.g. complete discontinuities or unconnected breaks) in the strap around the anterior of the chassis portion 3211.

Straps 3310 according to exemplary forms of the technology are illustrated in FIGS. 10A-10B, 11A-11C, 13A-13B, 15A-15B and 16A-16B. In the exemplary forms, the positioning and stabilising structure 3300 consists of only a single strap 3310. That is, there are no other straps that comprise part of the positioning and stabilising structure 3300 and the strap 3310 is capable of maintaining the seal-forming structure 3100 in a therapeutically effective (e.g. sealed) position on its own. Some conventional positioning and stabilising structures for patient interfaces take the form of headgear that consists of multiple straps attached together in different directions because each strap is intended to sit on a different part of the patient's head. Such headgear assemblies can be complicated for a patient to arrange and put on their head, particularly in the dark and if the patient is tired or lacks dexterity. Forms of the technology described herein that consist of a single strap 3310 are simpler and more intuitive for a patient to put on because only a single strap needs to be handled and oriented correctly. This may promote the patient to use the patient interface and conform with their therapy prescription.

In certain forms of the technology, the patient interface 3000 is configured so that the strap 3310 does not contact the breathable gas being delivered to the patient. Having no contact with the airpath may provide more options for the material from which the strap 3310 may be made, since the strap 3310 may need to conform to fewer regulatory requirements if it does not contact the airpath during use. In particular, the strap 3310 may be formed from an aesthetically pleasing material or from a material carrying an aesthetically pleasing pattern and/or colours.

The strap 3310 may be formed from one or more materials. In some forms in which the strap 3310 is formed from a plurality of materials, the materials may be blended, for example woven, together to form a single blended material. In other forms in which the strap 3310 is formed from a plurality of materials, the strap may comprise a plurality of portions, each formed from a different material, that are connected together to form the strap 3310.

4.3.2.1.1 Configuration of Strap

The exemplary straps illustrated in FIGS. 10A-10B, 11A-11C, 13A-13B, 15A-15B and 16A-16B are bands of material having a length L and a height H. These dimensions are marked on FIG. 11A by way of example.

The length L is the longest dimension of the strap 3310 and, when the patient interface 3000 is worn, extends in a loop around the patient's head. The length L of the strap 3310 is sufficiently long to circumvent the patient's head around the lower face and upper neck region. Straps 3310 may be supplied having different lengths in order to fit patients of different sizes. Alternatively, or additionally, the effective length of the strap 3310 (i.e. the length of the strap minus any overlap between the ends of the strap when worn) may be able to be adjusted as described below.

The height H of the strap 3310 (which may alternatively be referred to as its width) is a dimension of the strap in a direction approximately perpendicular to the length L. When the patient interface 3000 is worn, the height H extends in the superior-inferior direction, i.e. a direction perpendicular to the Frankfort horizontal plane of the patient.

The height H of the strap 3310 is smaller than the length L. In certain forms of the technology, the height H is significantly smaller than the length L, for example approximately an order of magnitude, or approximately 10 times smaller. The height H of the strap 3310 may vary along its length, as is the case with the strap 3310 illustrated in FIG. 11A. In exemplary forms of the technology, the strap 3310 may have a length L of approximately 400-700 mm, for example approximately 600 mm. The height H of the strap 3310 may be approximately 30-120 mm, for example 60-100 mm. In the form illustrated in FIGS. 10A-10B and 11A-11C the portions of the strap 3310 configured to overlay the sides and posterior of the patient's head have a height of approximately 40 mm and the portion of the strap 3310 configured to overlay the anterior surface of the chassis portion 3211 has a height of approximately 100 mm.

In certain forms of the technology, the strap 3310 comprises a first end 3312 and a second end 3314. The first and second ends are separated by the length L of the strap. The first end 3312 is configured to be secured to the second end 3314 to form a loop. In some forms, hook-and-loop material may be used to effect the securing of the first end 3312 to the second end 3314. For example, a first hook-and-loop material segment (which may be the hook or loop segment) may be provided to the first end 3312 and a second hook-and-loop material segment (which is the other of the hook or loop segment) may be provided to the second end 3312 on the other side of the strap 3310. The hook segment may be placed on a side of the strap 3310 facing away from the patient in use to reduce the level of discomfort experienced by the patient. In other forms, other connectors for securing the two ends of the strap 3310 together may be used, for example poppers, domes, clips and the like. A strap 3310 with detachable ends may be relatively easy for the patient to put on. A hook-and-loop securement mechanism may also be advantageous as it allows the effective length of the strap 3310 to be adjusted finely in order to fit the patient's head. In forms of the technology in which other connectors are used (e.g. poppers, domes and clips), multiple instances of the connectors may be provided to the strap 3310 in order to allow adjustment of the effective length of the strap 3310.

In the example illustrated in FIGS. 15A-15B, the strap 3310 comprises a fastening portion 3332, which may comprise a different material to other portions of the strap 3310. In this example the fastening portion 3332 is formed from hook material configured to form a hook-and-loop connection with the surface of the strap 3310 at or proximate the second end 3314 or with another (e.g. complementary) fastening portion 3332 at the second end 3314, such as a fastening portion 3332 formed from a loop material.

In other forms of the technology, the strap 3310 may be formed as a continuous loop without ends. In such a form, the strap 3310 may be donned by being pulled down over the top of the head.

The strap 3310 may comprise a cushion engaging portion 3316 between the first end 3312 and the second end 3314. The cushion engaging portion 3316 may be configured to engage the cushion module 6100 and in some examples may be approximately mid-way between the first end 3312 and the second end 3314 of the strap 3310. When the strap 3310 is worn by the patient, the cushion engaging portion 3316 may be approximately positioned on the opposite side of the patient's head from the region at which the first end 3312 overlaps the second end 3314 (or vice versa). The cushion engaging portion 3316 may have a greater height H compared to other portions of the strap 3310.

In certain forms, the strap 3310 is configured to be arranged, when worn, so that the anterior portion of the strap 3310 overlying the anterior surface of the chassis portion 3211 comprises the cushion engaging portion 3316 and the posterior portion of the strap 3310 overlying the posterior region of the patient's neck comprises the first end 3312 and/or second end 3314. In other forms, the first end 3312 and the second end 3314 may overlap in a different location with respect to a circumference around the patient's head, such as a side of the patient's head. Arranging the strap 3310 with ends that connect together around the back of the head with the cushion engaging portion 3316 directly in front of the patient may be intuitive for the patient and also moves the ends of the strap 3310, which may be more prone to rub on the patient's skin around the back of the head away from the sensitive areas of the patient's face. It is to be understood that in some examples of the technology the cushion engaging portion 3316 of the strap 3310 is not spaced midway between ends of the strap 3310. Features of the anterior portion and/or cushion engaging portion 3316 described herein are to be understood to be applicable whether the cushion engaging portion 3316 of the strap 3310 is centred between the first end 3312 and the second end 3314 along the length of the strap 3310, or not.

In certain forms of the technology, for example as shown in FIG. 13A, the strap 3310 may include a split 3318. The split 3318 may divide the strap 3310 into two portions, for example a superior portion and an inferior portion. The split 3318 may be oriented approximately longitudinally along the strap 3310. The split 3318 may extend part of the way along the strap 3310. For example, in the example of FIG. 13A, the split 3318 extends along the length of the strap between the cushion engaging portion 3316 and a portion of the strap 3310 that overlies a posterior region of the mandible when worn. Other forms may comprise a split 3318 having a different extent.

4.3.2.1.2 Positioning of Strap

In certain forms of the technology, the strap 3310 is configured to be worn so that the strap 3310 overlies the cushion module 6100 and passes around the back of the patient's head. For example, the anterior portion of the strap 3310 may comprise a cushion engaging portion 3316 configured to engage the cushion module 6100 and the strap 3310 may comprise a first end 3312 and a second end 3314, the strap 3310 being configured so that the first end 3312 is able to be secured to the second end 3314 so that the strap 3310 forms a loop. The strap 3310 is worn in an arrangement in which a longitudinal axis of the strap (i.e. an axis extending along the direction of length L) forms a loop around the patient's head approximately in the form of a plane curve with the plane oriented approximately parallel to the Frankfort horizontal plane of the patient. For example, the strap 3310 may overlie the cushion module 6100 and also overlie a region of the patient's face approximately between their chin and nasal bridge region in the case of a full face cushion module 6100, or part of that region. The strap 3310 may extend laterally across the patient's cheeks and passes around the sides of the patient's head at a level that is inferior to the ears. The posterior portion of the strap 3310 may overlie a posterior region of the patient's neck, for example a superior portion of the patient's neck.

As can be seen in FIGS. 10A-10B and 13A, which illustrate straps 3310 according to certain forms of the technology being worn, the strap 3310 overlays an anterior portion of cushion module 6100. The strap 3310 may particularly overlay a middle region of the cushion module 6100 with respect to its height, but in the illustrated forms, the strap 3310 has sufficient height in the cushion engaging portion 3316 to overlay a majority of the height of the cushion module 6100. Around the sides of the head, the strap 3310 may overlie a posterior part of the lower jaw region, for example the angle towards the posterior of the mandible. In certain forms the strap 3310 may be configured to be positioned so that a superior edge of the strap is spaced apart from the inferior portion of the ear, i.e. there is a spacing between the ear and the strap 3310. This may be useful in avoiding uncomfortable rubbing of the strap with the ear. In some forms, an edge of the strap 3310 may have formed therein indents positioned at points along the length of the strap 3310 which are aligned directly inferior to the ears in use to help create a spacing between the strap 3310 and the ears. Posterior to the neck, the strap 3310 is positioned overlying a superior region of the neck just inferior to the occipital bone, for example the strap 3310 may overlie the upper vertebrae of the cervical spine, e.g. C1, C2 and/or C3.

In certain forms of the technology, for example, the forms shown in FIGS. 10A-10B and 13A, no part of the positioning and stabilising structure 3300 is configured to be positioned superior to the patient's ears in use. For example, strap 3310 may be the only component of the positioning and stabilising structure 3300. In some forms of the technology, other straps may be used but no strap may be positioned superior to the patient's ears when worn. In these forms, the retention force of the strap 3310 acting on the cushion module 6100 is sufficient to maintain the seal-forming structure 3100 in a therapeutically effective position without the need for straps positioned superior to the ears.

A single strap 3310 passing around the patient's head inferior to the ears may be able to provide a sufficient retention force to hold the seal-forming structure 3100 in therapeutically effective (e.g. sealed) position because, in the case of a full face mask or a nasal mask, the primary direction of force that is applied by the strap 3310 (i.e. the headgear vector) is in a posterior direction, and no component of the force in a superior or inferior direction may be needed. Consequently arranging the strap 3310 in the position described produces a suitable headgear vector acting on the cushion module 6100 to promote a therapeutically effective sealed contact around the periphery of the seal-forming structure 3100.

In the described configuration, the strap 3310 may, when worn, overlie only a small amount of the patient's hair, for example the hair passing down over the neck. Consequently, a strap 3310 according to forms of the technology described herein, may avoid causing lines and creases in hair, particularly in hair on top of the head, which can occur using some conventional headgear systems for masks and is generally not desirable.

4.3.2.1.3 Anterior Portion

The anterior portion of the strap 3310 is the portion of the strap that, when the strap 3310 is positioned during use, is positioned on an anterior side of the cushion module 6100, i.e. overlying the side of the cushion module 6100 facing away from the patient. As explained above, in certain forms of the technology, the anterior portion may comprise the cushion engaging portion 3316 of the strap 3310 in the case where the ends of the strap 3310 connect around the posterior side of the patient's head. Features of the anterior portion will now be described and will be described in terms of them being features of the cushion engaging portion 3316 as is the case with the forms of the technology illustrated in FIGS. 10A-10B, 11A-11C, 13A-13B, 15A-15B and 16A-16B by way of example. It should be understood that, in other forms of the technology, the anterior portion and/or cushion engaging portion 3316 may be formed from a region of the strap other than the middle portion along the length of the strap 3310 and the description of the features provided below apply to that region in those forms.

In certain forms of the technology, a height H of the strap 3310 in the cushion engaging portion 3316 is such that, when the strap 3310 is worn during use, the central portion 3316 of strap 3310 covers a majority of the height of the plenum chamber 3200. This arrangement assists in distributing the retention force exerted by the strap 3310 on the plenum chamber 3200 across the majority of the height H of the cushion engaging portion 3316, including exerting a force proximate a superior end of the chassis portion 3211 and proximate an inferior end of the chassis portion 3211. This may help to maintain the seal-forming structure 3100 in sealed contact with the patient's face and to avoid leak points arising when pressurised gas is supplied to the plenum chamber 3200.

Furthermore, the cushion engaging portion 3316, and other parts of the strap 3310, may have a relatively consumer-friendly appearance, for example it may be made of an aesthetically pleasing material or use aesthetically pleasing patterns, colours or finishes, and therefore the strap 3310 covering the cushion module 6100, which in some examples may be more unsightly or 'medical-looking' in appearance, may be desirable for some patients. In forms of the technology in which the strap covers a smaller amount of the height of the chassis portion 3211, it may be more advantageous to ensure the strap is positioned in the middle of the chassis portion 3211 with respect to its height in order to maintain sealed contact with the face.

4.3.2.1.3.1 Curvature

In certain forms of the technology, the cushion engaging portion 3316 may be formed to have a curvature so that, in use, the cushion engaging portion 3316 cups around the chassis portion 3211. This cupping may assist in holding the cushion module 6100 in place during use and may also help to avoid wrinkles or creases arising in the strap 3310, which may impact the ability of the strap to retain the cushion module 6100 in place, may catch on bed linen or other nearby objects during use, or may be unsightly. The cupping of the cushion engaging portion 3316 of the strap 3310 may be such that it is similarly shaped, e.g. having an approximately equal degree of curvature in at least one direction, to the anterior portion of the cushion module 6100.

The curvature of the cushion engaging portion 3316 may be a positive curvature on the side of the strap 3310 facing towards the patient during use, i.e. the strap presents a concavity towards the patient. It will be appreciated that this may mean the side of the strap facing away from the patient during use has a negative curvature. The curvature may be present along the longitudinal axis of the strap 3310 (i.e. in the direction of the length L), which corresponds to the medial-lateral direction with respect to the patient when the strap is worn. Additionally, curvature may be present along a direction at an angle to this axis/direction, including at a perpendicular angle, i.e. along the direction of the height H of the strap 3310, which corresponds to the superior-inferior direction with respect to the patient when the strap is worn.

In certain forms, the cushion engaging portion 3316 is formed to have an inherent curvature by pre-forming the cushion engaging portion 3316 in an appropriate manner. For example, the cushion engaging portion 3316 may be moulded with a curved shape. Alternatively, in the case of the strap 3310 being made from a fabric, the fabric may be woven in a manner that creates inherent curvature to the material. Alternatively, or additionally, the fabric may be folded and joined in a manner that creates curvature in the strap 3310, for example by the use of one or more pleats. Alternatively, or additionally, one or more notches, e.g. V-shaped notches, may be cut into edges of the fabric and then the edges of the notches be subsequently re-joined (for example through stitching, gluing or thermoforming).

4.3.2.1.3.2 Support Members

In certain forms of the technology, the positioning and stabilising structure 3300 may comprise one or more support members 3320 provided to the cushion engaging portion 3316 of the strap 3310. The one or more support members 3320 may be configured to provide curvature to, or substantially maintain the inherent curvature of, the cushion engaging portion 3316 when the cushion engaging portion 3316 is put under tension. The support members 3320 may help to avoid the strap 3310 flattening or folding under tension. The one or more support members 3320 may be configured to be rigid or semi-rigid when subject to typical forces applied during use. The rigidity/semi-rigidity may be achieved through the stiffness of the material from which the support members 3320 are made, through the shape of the support members 3320, or through a combination of these properties. In exemplary forms the support members 3320 may be formed of a rigid or semi-rigid polymer, for example a plastic material. In some examples the support members 3320 are formed from TPU or TPE.

The support members 3320 may have a curved shape in order to provide a similar curvature to the strap 3310, i.e. so that the strap 3310 adopts the contours of the support members 3320 when the support members are provided to the strap 3310. Alternatively, or additionally, a plurality of support members 3320 may be arranged in a manner that, when arranged together, provide a curvature to the strap 3310. In this way, each support member 3320 may not be curved itself. In certain forms, the support members 3320 may be arranged together to form a frame. The support members 3320 may be connected together to form the frame. Any suitable connection mechanism may be used, for example gluing, hinging, interlocking, friction fit. In some forms, the support members 3320 may be integrally formed together in the form of a frame.

The support members 3320 may also act to transfer the retention force exerted by the strap 3310 onto the cushion module 6100, as discussed in more detail below.

The support members 3320 may be provided to one or both sides of the strap 3310. In the form of the technology shown in FIGS. 11A-11C and 13A-13B, the support members 3320 are provided to a side of the cushion engaging portion 3316 of strap 3310 configured to face towards the patient during use. This avoids the support members 3320 being outwardly visible when the patient interface 3000 is worn. It also allows the support members 3320 to directly interact with the cushion module 6100.

The support members 3320 may be connected to the strap 3310 in any suitable manner. In various forms of the technology, the support members may be glued, stitched or thermoformed to the strap 3310, for example. In some examples the support members 3320 are covered by other material(s) forming the strap 3310. The support members 3320 may be sandwiched between other layers of material, such as a layer configured to face towards the patient's skin in use and a layer configured to face away from the patient's skin in use. For example, the support members 3320 of the strap 3310 shown in FIGS. 15A-15B are positioned internally within the material forming the strap 3310. In some examples, the support members 3320 are provided to the strap 3310 between a first outer layer 3338 and a second outer layer 3338. As shown in FIG. 15B by way of one example, the support members 3320 may be provided to the anterior portion of the strap 3310 between the first outer layer 3338 and the second outer layer 3338.

In certain forms of the technology, one or more of the support members 3320 are arranged to span across a length of the cushion engaging portion 3316, i.e. they span in a lateral-medial direction when the patient interface 3000 is being worn by a patient. The support members 3320 may span across substantially the full width of the cushion engaging portion 3316 or the support members 3320 may span across a part of the width of the cushion engaging portion 3316. The support members 3320 may be arranged symmetrically with respect to the middle of the cushion engaging portion 3316 with respect to its length, i.e. when worn, the support members 3320 are arranged symmetrically with respect to the mid-sagittal plane of the patient.

4.3.2.1.3.2.1 Support Member Portions

In the forms of the technology shown in FIGS. 11A-11C and 13A-13B, the support members 3320 comprise a first spanning support member portion 3322 in a region of the cushion engaging portion 3316 that is positioned superior to the opening 3330 (described below) when the patient interface 3000 is worn by the patient, and a second spanning support member portion 3322 in region of the cushion engaging portion 3316 that is positioned inferior to the opening 3330. In some forms the first spanning support member portion 3322 is positioned proximate one edge of the cushion engaging portion 3316. In some forms the second spanning support member portion 3322 is positioned proximate the other, opposite edge of the cushion engaging portion 3316. A support member may comprise a plurality of support member portions, the support member portions being connected together (e.g. integrally formed or otherwise connected) to form the support member.

In the form of the technology shown in FIGS. 11A and 11C, the first and second spanning member portions 3322 are comprised as part of a ring-shaped support member 3320 that surrounds the opening 3330. The ring-shaped support member 3320 is generally trapezoidal in shape with rounded corners and an opening in the middle. As such, "ring-shaped" in this context will be understood to mean that the support member forms a closed loop of any shape. A ring-shaped support member in other forms of the technology may be other shapes, including generally circular, square, rectangular, triangular, or other polygonal or curved shapes, and may have rounded corners or otherwise.

The ring-shaped support member 3320, and in some forms other of the support members 3320, may be formed from members that are significantly longer than they are wide, e.g. the ring-shaped support member 3320 may have the form of a 'wire' or other skeletal frame.

In certain forms of the technology, the one or more support members 3320 comprise one or more side support member portions 3324 provided to one or more sides of the cushion engaging portion 3316. That is, the side support member portions 3324 may be positioned on the cushion engaging portion 3316 so that, when the patient interface 3000 is worn, each side support member portion overlays, or is positioned adjacent, a lateral side of the chassis portion 3211 of cushion module 6100.

In the forms of the technology shown in FIGS. 11A-11C and 13A-13B, the straps 3310 comprise side support member portions 3324 positioned on each side of the cushion engaging portion 3316, e.g. symmetrically arranged. When worn, the side support member portion 3324 on one side of the cushion engaging portion 3316 overlays one lateral side of the chassis portion 3211 and the side support member portion 3324 on the other side of the cushion engaging portion 3316 overlays the other lateral side of the chassis portion 3211. More generally, the side support member portions 3324 may form a first support member portion 3320 and a second support member portion 3320. Each of the first support member portion 3320 and the second support member portion 3320 may be positioned so that, in use, the first support member portion 3320 contacts a first lateral side of the cushion module 6100 (for example the chassis portion 3211 thereof) and the second support member portion 3320 contacts a second lateral side of the cushion module 6100, the first lateral side of the cushion module 6100 being opposite the second lateral side of the cushion module 6100. In the illustrated forms, the side support member portions 3324 are oriented transversely to the length L of the strap 3310, or with at least a part of the side support members 3324 extending at least partly in such a direction.

In certain forms, a support member 3320 may act as both a spanning support member portion 3322 and a side support member portion 3324. For example, in the form of the technology shown in FIGS. 11A and 11C, the ring-shaped support member 3320 comprises two sides extending parallel to the direction of the length of the strap 3310, i.e. spanning support member portions 3322, and two sides extending between the spanning support member 3322 and in a direction generally transverse to the length L of the strap 3310, i.e. side support member portions 3324. Furthermore, this exemplary form comprises further side support member portions 3324 positioned adjacent the side support members of the ring-shaped support member. In the form of the technology shown in FIG. 13B, one of the support members 3320 (in this case the superior-most support member) is generally U-shaped with the U-shape having an elongated trough oriented across the cushion engaging portion 3316 acting as a spanning support member portion 3322 and extending to the tips of the U-shape extending partly across the cushion engaging portion 3316 that act as side support member portions 3324.

In some examples, such as in the strap 3310 shown in FIGS. 15A-15B, the strap 3310 comprises support members 3320 in the form of a first support member portion 3320*a* and second support member portion 3320*b* each positioned within the cushion engaging portion 3316. The first support member portion 3320*a* may be located superior in use to the opening 3330 (described in more detail below) and the second support member portion 3320*b* may be located inferior in use to the opening 3330. More generally, the first support member portion 3320*a* may be provided to a superior portion of the cushion engaging portion 3316 and the second support member portion 3320*b* may be provided to an inferior portion of the cushion engaging portion 3316. In other examples the first support member portion 3320*a* may be provided to a first lateral side of the cushion engaging portion 3316 and the second support member portion 3320*b* may be provided to a second lateral side of the cushion engaging portion 3316.

The support members 3320 in some straps 3310 may occupy a majority of the space within the cushion engaging portion 3316. As shown in FIGS. 15A-15B for example, the support members 3320 span across substantially the entire width of the cushion engaging portion 3316 and also span across a majority of the height of the cushion engaging portion 3316 in the superior-inferior directions in use.

The first support member portion 3320*a* comprises a superior edge that closely follows a superior edge of the cushion engaging portion 3316. An inferior edge of the first support member portion 3320*a* is positioned superiorly adjacent the opening 3330 and spans from one lateral side of the cushion engaging portion 3316 to the other lateral side thereof. The second support member portion 3320*b* comprises an inferior edge which closely follows an inferior edge of the central portion 3316. Lateral edges of the second support member portion 3320*b* are also shaped to closely follow the shape of lateral edges of the central portion 3316. The superior edge of the second support member portion 3320*b* is located adjacent the opening 3330 and curves superiorly on either lateral side of the opening 3330 towards lateral sides of the cushion engaging portion 3316. In this particular example the support members 3320 do no occupy spaces laterally adjacent the opening 3330.

In other examples the strap 3310, the first support member portion 3320*a* and the second support member portion 3320*b* may be integrally formed as a single support member 3320. Such an integrally formed support member 3320 may occupy substantially the same space as the support members 3320 occupy in the strap 3310 shown in FIGS. 15A-15B, or in some examples a single integrally formed support member 3320 may occupy substantially all of the space with the cushion engaging portion 3316.

FIG. 18A shows a strap 3310 according to another example of the present technology. In this example the strap 3310 comprises a peripheral support member 3321. The peripheral support member 3321 may be positioned at, and may lie along, a periphery of the central portion 3316 of the strap 3310.

The peripheral support member 3321 may be configured to maintain a peripheral shape of the cushion engaging portion 3316 of the strap 3310. The peripheral support member 3321 in this example is configured to hold the cushion engaging portion 3316 of the strap 3310 in a predetermined three-dimensional shape in use. The predetermined three-dimensional shape may match or correspond to the shape of an anteriorly facing side of the cushion module 6100, e.g. of the chassis portion 3211. The peripheral support member 3321 may maintain the cushion engaging portion 3316 in a predetermined three-dimensional shape during therapy when the lateral sides of the strap 3310 are in tension. That is, the peripheral support member 3321 may prevent the lateral sides of the strap 3310 that extend towards the posterior region of the patient's neck or head from pulling the cushion engaging portion 3316 into a deformed shape. The peripheral support member 3321 may maintain the cushion engaging portion 3316 in a dome or cup shape. This may distribute the tension force evenly over the cushion module 6100 or in a predetermined manner.

In some examples, the peripheral support member 3321 may be provided at lateral sides of the cushion engaging portion 3316 and at a superior side of the cushion engaging portion 3316. The peripheral support member 3321 in some examples may extend around an entire periphery of the cushion engaging portion 3316. In the example shown in FIG. 18A the peripheral support member 3321 extends from an inferior location on one lateral side of the cushion engaging portion 3316 superiorly and around the periphery of the cushion engaging portion 3316 to an inferior location on the other lateral side of the cushion engaging portion 3316.

As illustrated, the peripheral support member 3321 is substantially U-shaped and opens inferiorly when the strap 3310 is donned by the patient. The peripheral support member 3321 in this example may be described as having a spanning support member portion 3322 (along the superior edge of the periphery of the cushion engaging portion 3316) and a pair of side support member portions 3324 (along the lateral edges of the periphery of the cushion engaging portion 3316).

In use, one of the pair of side support member portions 3324 may be configured to lie substantially over a first lateral side of the cushion module 6100, and the other pair of side support member portions 3324 may be configured to lie substantially over a second lateral side of the cushion module 6100.

In other examples of the present technology, the peripheral support member 3321 may be substantially circular, oval-shaped or the like, and/or may be shaped to extend around the entire periphery of the cushion engaging portion 3316.

The peripheral support member 3321 may be located proximate but spaced from the peripheral edge of the cushion engaging portion 3316 or may be located immediately adjacent or may form the peripheral edge of the cushion engaging portion 3316. In the FIG. 18A example the peripheral support member 3321 is located proximate but spaced from the edge of the cushion engaging portion 3316 by a small amount.

In some examples, the peripheral support member may be encapsulated between a first outer layer 3338 and a second outer layer 3338 of the strap 3310. FIG. 18B shows an image of the periphery of the cushion engaging portion 3316 cut and split open to show the peripheral support member 3321. The broken line in FIG. 18B indicates the cut, with the cross section of the periphery of the cushion engaging portion 3316 shown on either side of the broken line. In this example the peripheral support member 3321 is encapsulated by the first and second outer layers 3338 of the strap 3310, which in this particular example are formed from foam with a textile outer surface. In alternative forms, the outer layers 3338 of the strap 3310 may be made of other materials.

A strap 3310 with a peripheral support member 3321 may be manufactured in the manner described above with reference to FIGS. 17A and 17B by which a strap having support members 3320 is manufactured. That is, foam and textile laminate outer layers 3338 may be thermoformed and bonded together around the peripheral support member 3321 (and also around other support members 3320 and/or inextensible layers, in some examples). The peripheral support member 3321 may bond to the outer layers 3338 or may be encapsulated sufficiently tightly that it does not move. The peripheral support member 3321 may be substantially immovable relative to the first outer layer 3338 and the second outer layer 3338.

The peripheral support member 3321 may be substantially rigid or may be semi-rigid. The peripheral support member 3321 may be sufficiently rigid that it substantially does not deform in use. In some examples, the peripheral support member 3321 may be formed from TPU or EVA, but may also be formed from any other suitable material in other examples. In some examples the peripheral support member 3321 is held in place with TPU film or heat activated glue.

In the example shown in FIG. 18A, the strap 3310 includes all of the features of the strap 3310 shown in FIGS. 15A and 15B, with the addition of the peripheral support member 3321. In other examples a strap 3310 may comprise the peripheral support member 3321 but may not have some or all of the other features of the strap 3310 shown in FIGS. 15A-15B and 18A.

4.3.2.1.3.2.2 Interaction Between Support Members and Cushion Module

In certain forms of the technology, the support members 3320 may be arranged to come into contact with the chassis portion 3211 when the patient interface 3000 is assembled and in use. This contact transfers the retention force of the strap 3310 to the cushion module 6100. By selectively positioning the support members 3320 the force can be directed to particular areas of the cushion module 6100. For example, in some forms the side support member portions 3324 contact the sides of the cushion module 6100 in order to transfer some of the retention force to the side parts to the cushion module 6100. This may result in a greater proportion of the retention force being transferred to the patient's cheek regions compared to other forms, which may be desirable as the cheek region has bone underlying it and therefore provides a solid foundation for the seal-forming structure 3100 and is also less sensitive than other areas of the face, e.g. the nasal bridge region.

In some forms of the technology, the contact between the support members 3320 and the chassis portion 3211 may be a surface-to-surface contact. In some forms, the region of the chassis portion 3211 positioned adjacent the support members 3320 when the patient interface 3000 is worn may be shaped in a complementary way to the shape of the respective support members 3320. In some forms, the support members 3320 may be shaped to engage with the chassis portion 3211, e.g. by an interlock or by a hook-and-loop fastening. This may help to keep the components of the patient interface 3000 arranged in the intended position over the course of a therapy session. In other forms, a part of the strap 3310 other than support members 3320 may be configured to engage with the chassis portion 3211 to hold the strap 3310 and cushion module 6100 in relative position to each other.

In some forms of the technology, the cushion engaging portion 3316 has one or more regions where a support member 3320 is not provided. For example, in the forms of the technology shown in FIGS. 11A-11C and 13A-13B there are no support members provided to some central areas of the cushion engaging portion 3316. This may allow the strap 3310 to flex in these areas to accommodate movement of the cushion module 6100, for example relative movement between a superior portion 3212 and an inferior portion 3214 of the chassis portion 3211.

In the example shown in FIGS. 15A-15B the support members 3320 are thermoformed so as to be substantially rigid or semi-rigid, and may be formed from TPU or TPE by way of example. The thermoformed shape of the support members 3320 may match or complement the shape of the cushion module 6100 (e.g. the shape of a surface of the cushion module 6100 configured to face the patient-facing side of the cushion engaging portion 3316 in use, which may be a surface of the chassis portion 3211). In the example shown in FIG. 15A-15B, the support members 3320 occupy a large area within the cushion engaging portion 3316 and have a high stiffness, allowing some of the material forming the cushion module 3316 to be thinner.

The cushion engaging portion 3316 of the strap 3310 in some examples may comprise connection holes 3326 configured to facilitate connection of the strap 3310 to the cushion module 6100. In the example shown in FIGS. 15A-15B, the strap 3310 comprises four connection holes 3326 within the cushion engaging portion 3316. The cushion module 6100 of the patient interface 3000 may comprise protrusions configured to form a press fit connection with the connection holes 3326 to attach the strap 3310 to the cushion module 6100 in use. The connection holes 3326 are in this example formed in the one or more support members 3320. In other examples the connection holes 3326 may be formed as through-holes through the strap 3310 from an anterior side to a posterior side.

4.3.2.1.3.3 Opening

In certain forms of the technology, the anterior portion of the strap 3310 has an opening 3330 formed therein, for example in the cushion engaging portion 3316. The opening 3330 is configured to accommodate a conduit for conveying the flow of breathable gas to the plenum chamber inlet port 3205.

The position of the opening 3330 may be such that it aligns with the location of the conduit/plenum chamber inlet port 3205 when the patient interface 3000 is assembled and being worn. In some forms, for example those illustrated in FIGS. 11A-11C, 13A-13B and 15A-15B, the opening 3330 is located in a central part of the cushion engaging portion 3316. For example, the opening 3330 may be centrally located with respect to the length of the cushion engaging portion 3316. The opening 3330 may be located in an inferior part of the cushion engaging portion 3316 when the patient interface is worn.

The opening 3330 may be a through-hole in the material(s) forming the cushion engaging portion 3316. The opening 3330 may be circular to match the shape of a circular conduit. The diameter of the opening 3330 may be slightly larger than the diameter of the conduit that it accommodates during use. This ensures the conduit can readily be passed through the opening 3330 but the opening does not expose much of the anterior face of the chassis portion 3211.

In other forms, the opening 3300 may be a recess in an edge of the cushion engaging portion 3316 of the strap 3310. For example, the opening may be a recess in the edge of the cushion engaging portion 3316 that is the inferior edge when the patient interface 3000 is being worn.

4.3.2.1.3.4 Gas Permeability

In certain forms of the technology, the strap 3310 may contribute to the venting of gases exhaled by the patient to ambient, particularly the diffusing of such gases to reduce the velocity and/or to spread the vent flow of gases over a broader range of dispersion angles. A reduction in the velocity of the vent flow of gases may reduce the noise produced by exhaled gases vented by the patient interface 3000, which may be desirable. Furthermore, a reduction in the velocity of exhaled gases and/or a greater angular spread of exhaled vent flow may improve comfort for the patient and/or the patient's bed partner by reducing the strength of jets of venting gases leaving the patient interface 3000, which can be felt by the patient/bed partner. Since the flow of exhaled gases into objects in the sleeping area, such as pillows and bed sheets can produce noise, a more diffuse vent flow may further reduce the noise produced when using the patient interface 3000.

In certain forms of the technology, the cushion module 6100 comprises a vent structure to allow a continuous vent flow of exhaled gases to flow from an interior of the plenum chamber 3200 to ambient. For example, the vent structure may be located in the chassis portion 3211, for example an anterior surface of the chassis portion 3211 facing away from the patient during use.

In certain forms, the strap 3310 may comprise a gas permeable portion. The strap 3310 may be configured so that the gas permeable portion is located on the strap 3310 at a position where, when the patient interface 3000 is assembled and worn during use, the gas permeable portion overlies some or all of the vent structure on the cushion module 6100. Consequently, exhaled gases from the patient, after passing through the vent structure, need to pass through the gas permeable portion of the strap 3310 prior to reaching ambient. The gas permeable portion of the strap 3310 is configured in a way that it acts to diffuse the vent flow of gases leaving the vent structure.

For example, the gas permeable portion of the strap 3310 may be formed from a porous material, i.e. a material in which there are a plurality of pores through which a gas may flow. In certain forms, the pores are sufficiently large to allow the sufficient washout of exhaled $CO_2$ from the patient interface 3000 but sufficiently small that some of the vent flow impacts the material in between the pores, thereby diffusing the flow.

In certain forms of the technology, the gas permeable portion of the strap 3310 is located in the anterior portion of the strap, for example the cushion engaging portion 3316.

In certain forms, the strap 3310 may be formed of a material that is porous to allow moisture, e.g. sweat, to pass through the strap 3310.

4.3.2.1.4 Substantially Inextensible and Low-Extensibility Portions

In some examples of the present technology, the strap 3310 may comprise one or more portions having a lesser extensibility (e.g. extension stiffness) than one or more other portions of the strap 3310. In some examples the strap 3310 may comprise one or more portions that are substantially inextensible.

In the example shown in FIGS. 15A-15B, the strap 3310 comprises substantially inextensible portions 3334. More generally, the strap 3310 may comprise a first substantially inextensible portion 3334 positioned between the anterior portion of the strap 3310 and the posterior portion of the strap 3310 on a first lateral side of the patient's head in use, and a second substantially inextensible portion 3334 positioned between the anterior portion of the strap 3310 and the posterior portion of the strap 3310 on the second lateral side of the patient's head in use. In this example the substantially inextensible portions 3334 are located on either lateral side of the cushion engaging portion 3316. The strap 3310 comprises a first substantially inextensible portion 3334 located between the cushion engaging portion 3316 and the first end 3312 and a second substantially inextensible portion 3334 located between the cushion engaging portion 3316 and the second end 3314. Each substantially inextensible portion 3334 in this example extends laterally from adjacent the cushion engaging portion 3316 to the respective one of the first end 3312 and second end 3314. The substantially inextensible portions 3334 in this example are provided adjacent superior edges of the portions of the strap 3310 on either lateral side of the cushion engaging portion 3316. In other examples the substantially inextensible portions 3334 may be provided adjacent inferior edges of the strap 3310.

The substantially inextensible portions 3334 may be wider in the width W dimension of the strap 3310 at some locations along its length L than others. For example, as shown in FIG. 15A, the substantially inextensible portions 3334 are wider proximate the cushion engaging portion 3316 than proximate the first end 3312 and second end 3314 of the strap 3310. As illustrated, the substantially inextensible portions 3334 may occupy substantially an entire width of the strap 3310 proximate the cushion engaging portion 3316 and may occupy approximately half of the width of the strap proximate the ends.

The strap 3310 in some examples may comprise low extensibility portions 3336. This low extensibility portions 3336 may be located on respective lateral sides of the strap 3310. As shown in FIGS. 15A-15B, the strap 3310 in this example comprises a pair of low extensibility portions 3336, each of which is provided proximate a respective end of the strap 3310. Each low extensibility portion 3336 may extend from a respective end of the strap 3310 approximately halfway to a respective lateral edge of the cushion engaging portion 3336. The low extensibility portions 3336 may each occupy approximately half of the width of the strap 3310 proximate the ends of the strap 3310 (the width of the strap being measured in a direction substantially parallel to a superior-inferior axis of the patient's head, e.g. perpendicular to the length), with the substantially inextensible portions 3334 each occupying the other half of the width of the strap 3310 proximate the ends of the strap 3310. The low extensibility portions 3336 may be configured to reduce peak contact pressure on the neck by having some amount of extensibility. The edge of the strap is able to extend to reduce the force it exerts on the patient's skin. In examples in which the strap 3310 comprises low extensibility portions 3336, elastic regions 3350 and also substantially inextensible portions 3334, the low extensibility portions 3336 may be more extendable than the substantially inextensible portions 3334 but less extendable than the elastic regions 3350.

The substantially inextensible portion 3334 may comprise webbing and may be formed from a material and/or a stitch/pattern/weave that results in substantially no extensibility, such as a polyamide filament ultra lightweight woven interlining, by way of example. The low extensibility portion 3336 may also comprise a webbing and may be formed from a material and/or a stitch/pattern/weave that results in a low extensibility, such as lightweight fusible interlining, made out of fine polyamide yarn, by way of example. Each of the substantially inextensible portion 3334 and the low extensibility portion 3336 may be thin, for example thin in comparison to the overall thickness of the strap 3310, and may each comprise a layer of fabric.

4.3.2.1.5 Outer Layers

In some examples of the present technology the strap 3310 may comprise outer layers distinct from inner layers or portions between outer layers. In the example shown in FIGS. 15A-15B, the strap 3310 comprises a pair of outer layers 3338 as shown in the exploded view of the strap 3310 in FIG. 15B. The outer layers 3338 in this example form the entire posterior (e.g. patient-facing) and anterior (e.g. non-patient-facing) sides of the strap 3310. The outer layers 3338 may comprise a first outer layer 3338 and a second outer layer 3338.

The outer layers 3338 may be elastically extendable and, in some particular examples, may comprise foam and/or textile materials. In some examples each outer layer 3338 comprises a laminate. The laminate forming the outer layer 3338 may comprise a foam inner layer and a textile outer layer. The textile layer may provide a comfortable and aesthetically pleasing outer surface of the strap 3310 while the foam layer may provide the strap with cushioning.

The outer layers 3338 may be provided in the cushion engaging portion 3316 and also in the lateral portions of the strap 3310 extending from the cushion engaging portion 3316 to the first end 3312 and second end 3314 of the strap 3310. The outer layers 3338 may form substantially the entire surface area of the strap 3310.

The outer layers 3338 may be elastically extendable to provide for length adjustment, as discussed below. However, despite the elastically extendable nature of the outer layers 3338, the substantially inextensible portions 3334 and low extensibility portions 3336 may reduce the extensibility of targeted regions of the strap 3310.

4.3.2.1.6 Length Adjustment

In certain forms of the present technology, a patient interface system is provided that comprises more than one strap 3310, each of the straps being configured to provide a retaining force to correspond to a different size and/or shape range. For example, the system may comprise one strap 3310 suitable for a large sized head, but not a small sized head, and another strap 3310 suitable for a small sized head, but not a large sized head.

In certain forms of the technology, a strap 3310 of patient interface 3000 is configured in a manner that allows the length of the strap 3310 to be adjusted. This adjustment allows the strap 3310 to be adjusted to suit individual patients, for example to enhance the comfort and/or fit of the mask to each person.

In some forms, the length adjustment mechanism is configured to allow the effective length of the strap 3310 to be adjusted while the actual length L of the strap 3310 remains the same. As explained earlier, the effective length of the strap 3310 may be considered to be the length of the strap minus any overlap between the ends of the strap when worn. Alternatively, or equivalently in some forms, the effective length of the strap 3310 may be considered to be the circumference of the inner surface of the loop formed when the strap 3310 is formed into a loop and positioned in the operative position around the patient's head. In this regard, the hook-and-loop material provided to the first end 3312 and second end 3314 may be considered to be an adjustment mechanism that allows the effective length of the strap 3310 to be adjusted. In other forms, other length adjustment mechanisms may be used, for example a buckle, a plurality of poppers, domes or clips, etc.

In other forms the length adjustment mechanism is configured to allow the actual length L of the strap 3310 to be adjusted. For example, the strap 3310 may comprise a ladder lock.

4.3.2.1.6.1 Elastic Region(s)

Alternatively, or additionally, the strap may comprise one or more elastic regions 3350. The elastic regions 3350 may be resiliently extensible to enable the length of the strap 3310 to be adjusted. The elastic regions 3350 may also act to provide tension to the strap 3310 to create a retention force that, in use, acts on the cushion module 6100 to retain it on the patient's face and to assist in creating a seal between the seal-forming structure 3100 and the patient's face.

In certain forms of the technology, the strap 3310 comprises a first elastic region 3350 in a region of the strap 3310 that, in use, is positioned between the anterior portion of the strap 3310 and the posterior portion of the strap 3310 on a first lateral side of the patient's head. The strap 3310 may further comprise a second elastic region 3350 in a region of the strap 3310 that, in use, is positioned between the anterior portion of the strap 3310 and the posterior portion of the strap 3310 on a second lateral side of the patient's head, i.e. the side opposite the first side. That is, there may be an elastic region 3350 positioned on the strap 3310 on other side of the patient's head when the patient interface 3000 is worn.

In the exemplary forms of the present technology illustrated in FIGS. 10A-10B and 11A-11C, the elastic regions 3350 are positioned between the cushion engaging portion 3316 and the first end 3312 and second end 3314 of the strap 3310 respectively. For example, the elastic regions 3350 may be immediately adjacent the cushion engaging portion 3316 on either side of the cushion engaging portion 3316. This may assist the elastic forces generated by the elastic region 3350 in acting effectively on the cushion engaging portion 3316 and passing that force to the cushion module 6100. When worn, the elastic regions 3350 may overlie the patient's cheek regions. In other forms of the technology, the elastic regions 3350 may be positioned in other locations, for example to overlay the patient's rear jaw and/or sides of the neck regions. In some forms of the technology, the elastic regions 3350 may extend along the length of the strap 3310 from the first and second ends 3312, 3314 to the cushion engaging portion 3316. In some forms of the technology, the entire length L of strap 3310 may be elastic and thereby comprise an elastic region 3350, for example, the strap 3310 may be formed, or partly formed, from an elastic material, e.g. elastane.

In certain forms, the elastic region(s) is/are provided along an edge of the strap 3310, which may include part of the edge. For example, in the forms of the technology illustrated in FIGS. 10B, 12A and 12C, the elastic regions 3350 are provided along a portion of a superior edge 3352 of the strap 3310, where the superior edge 3352 is the edge of the strap that is most superior in relation to the patient when the patient interface 3000 is being worn. In the forms of the technology illustrated in FIGS. 12B and 12C, the elastic regions 3350 are provided along a portion of an inferior edge 3354 of the strap 3310, where the inferior edge 3354 is the edge of the strap that is most inferior in relation to the patient when the patient interface 3000 is being worn. In the form of the technology illustrated in FIG. 12C, the elastic regions 3350 are provided along both a superior edge 3352 and an inferior edge 3354.

In the illustrated exemplary forms, the elastic regions 3350 are formed from lengths of an elastic material 3358 connecting two other portions of the strap 3310, for example two other portions along an edge of the strap 3310. In the illustrated forms, the strap edges (i.e. the superior edge 3352 and/or the inferior edge 3354) are formed to define recesses 3356 in the edges. The lengths of elastic material 3358 connect across the recesses 3356 between portions of the respective edges.

When the strap 3310 is worn by a patient, the elastic regions 3350 may be stretched and act on neighbouring regions of the strap 3310. This tends to create a tension along the length of the elastic regions 3350, pulling the regions of the strap 3310 that are anterior to the elastic regions 3350 and approximately in a line with the length of the elastic regions 3350 towards the back of the patient's head.

In the case of an elastic region 3350 provided along the superior edge 3352 of the strap 3310, the elastic region 3350 acts to pull the superior edge of the anterior portion of the strap 3310 backwards (i.e. in a posterior direction relative to the patient), which is a force that is applied to the portion of cushion module 6100 lying under the anterior portion of the strap 3310. This portion of the cushion module 6100 may be the superior portion 3212 of the plenum chamber 3200 and also the superior portion 3112 of the seal-forming structure 3100, so in these forms the elastic region 3350 may assist in maintaining the seal-forming structure 3100 in sealed contact with the nasal bridge region of the patient's face.

In the case of an elastic region 3350 provided along the inferior edge 3354 of the strap 3310, the elastic region 3350 acts to pull the inferior edge of the anterior portion of the strap 3310 backwards (i.e. in a posterior direction relative to the patient), which is a force that is applied to the portion of cushion module 6100 lying under the anterior portion of the strap 3310. This portion of the cushion module 6100 may be the inferior portion 3214 of the plenum chamber 3200 and also the inferior portion 3114 of the seal-forming structure 3100, so in these forms the elastic region 3350 may assist in maintaining the seal-forming structure 3100 in sealed contact with the chin region of the patient's face (in the case of a full-face mask) or the upper lip region (in the case of a nasal mask).

In the exemplary form of the technology shown in FIG. 13A, the split 3318 in the strap 3310 serves to divide the portion of the strap 3310 immediately adjacent cushion engaging portion 3316 into superior and inferior strap portions. The superior portion of the strap 3310 exerts a retention force on a superior region of the cushion module 6100 and the inferior portion of the strap 3310 exerts a retention force on an inferior region of the cushion module 6100.

In certain forms, the elastic region 3350 and/or the length of elastic material 3358 comprised as part of the elastic region 3350 may be provided at an angle to the direction of the length L of the strap 3310. For example, in the exemplary forms shown in FIGS. 10A-10B and 11A-11C, the length of elastic material 3358 provided along the superior edge 3352 of the strap 3310 is angled relative to the length L of the strap 3310 such that, when the strap 3310 is worn, an anterior-most portion of the length of elastic material 3358 is superior to the posterior-most portion of the length of elastic material 3358. Put another way, the length of elastic material 3358 may be angled upwards from the back to the front of the head. Such an angle may assist in changing the direction of force applied on the cushion module 6100 compared to the direction of the tension force that can be created along the length of the strap by the tension placed in the strap as a whole when secured around the patient's head. This tension force may generally tend to be in a posterior direction approximately parallel to the Frankfort horizontal plane. An angled length of elastic material 3358 may alter the direction of such a retention force so that the retention force acts on a part of the cushion module 6100 in a direction that forms an angle with the Frankfort horizontal lane in the inferior and/or superior directions. In some forms, an angled length of elastic material 3358 may be particularly useful along a superior edge 3352 as it may be more difficult to configure the strap 3310 in a way that there is a direct line of force through the strap 3310 to around the back of the head from a superior portion of the cushion module 6100 while avoiding contact of the strap 3310 with the patient's ears than it is from an inferior portion of the cushion module 6100. Consequently, there may be a greater need to use an angled length of elastic material 3358 to effectively change the direction of the retention force acting along the length of the strap 3310 on a superior part of the cushion module 6100 than on an inferior part of the cushion module 6100.

When the strap 3310 is being worn in use, movement of the patient's head or neck may change the shape and size of the region around which the strap 3310 wraps. This may cause the strap 3310, or regions thereof, to gain or lose tension. It is desirable if seal-forming structure 3100 is maintained in sealing contact with the patient's face throughout any such movements. In forms of the technology in which the strap 3310 comprises one or more elastic regions 3350, the elastic regions 3350 may act to retain a residual tension in the strap 3310 even if there is some loss of tension as a result of head/neck movements, retaining a retention force on the cushion module 6100.

In certain forms of the technology, the strap 3310 may be provided with multiple elastic regions 3350 having differing levels of elasticity in order to create the desired force profile acting on the cushion module 6100. The configuration of the elastic regions 3350 (including their position, shape and the amount of elasticity) may be customised to suit individual patients. Alternatively, a range of straps 3310 configured to apply a range of different retention force profiles may be provided for the patient and/or their healthcare practitioner to choose the strap from the range of straps that most suits the patient.

In the example shown in FIGS. 15A-15B the strap 3310 comprises a pair of elastic regions 3350 (see FIG. 15A) on respective lateral sides of the cushion engaging portion 3316. The elastic regions 3350 are each located proximate an inferior edge of the strap 3310 in this particular example. The elastic regions 3350 in this example may help provide sealing pressure when the patient interface 3000 is donned, as well as preload force on the cushion module 6100 into the chin region during head movement. This arrangement may also advantageously relieve high pressure on the back of the neck during head extension.

The elastic regions 3350 in the example shown in FIGS. 15A-15B are formed by elastically extendable outer layers 3338 together with a lack of other components or layers in the elastic regions 3350 which would resist extension of the outer layers 3338. As shown in FIGS. 15A-15B and in particular in FIG. 15B, the strap 3310 comprises recesses 3356 formed in the substantially inextensible portions 3334 at the locations of the elastic regions 3350 such that the outer layers 3338 (e.g. the first outer layer 3338 and the second outer layer 3338) define the strap 3310 at the elastic regions 3350. The material of the outer layers 3338 at the locations of the elastic regions 3350 and (recesses 3356) is free to elastically extend and may therefore be considered elastic material 3358 in the elastic regions 3350.

Accordingly, in some examples, such as that shown in FIGS. 15A-15B, a strap 3310 may comprise first and second elastic regions 3350 and first and second substantially inextensible portions. The first elastic region 3350 may be positioned between the anterior portion of the strap 3310 and the posterior portion of the strap 3310 on a first lateral side of the patient's head in use. The second elastic region 3350 may be positioned between the anterior portion of the strap 3310 and the posterior portion of the strap 3310 on a second lateral side of the patient's head in use. The first substantially inextensible portion 3334 may be positioned between the anterior portion of the strap 3310 and the posterior portion of the strap 3310 on a first lateral side of the patient's head in use. The second substantially inextensible portion 3334 may be positioned between the anterior portion of the strap and the posterior portion of the strap 3310 on the second lateral side of the patient's head in use. The first and second elastic regions 3350 may be provided adjacent one of a superior edge and an inferior edge of the strap 3310 and the first and second substantially inextensible portions 3334 may be provided adjacent the other of the superior edge and the inferior edge of the strap 3310. As shown in FIGS. 15A and 15B, the first and second substantially inextensible portions 3334 are provided adjacent (e.g. extending along) the superior edge of the strap 3310 and the first and second elastic regions 3350 are provided adjacent the inferior edge of the strap 3310.

In the example shown in FIGS. 16A-16B, the strap 3310 comprises elastic regions 3350 in approximately the same locations as those of the strap 3310 shown in FIGS. 15A-15B, however, the elastic regions are formed by added elastic material 3358 which fills a recess 3356 formed in the main body of the strap 3310.

4.3.2.1.7 Layered Construction

As described above with reference to FIGS. 15A-15B in particular the strap 3310 in some examples may comprise a layered construction. The strap 3310 may comprise a plurality of layers each having different properties, such as different elastic extension stiffnesses. FIGS. 17A-17B show schematically how a multi-layer strap 3310 may be constructed.

FIG. 17A shows a pair of outer layers 3338, which may each comprise a foam inner layer and a textile outer layer, a support member 3320 and a webbing 3340. The outer layers 3338 and support member 3320 may be as described above, for example. The webbing 3340 may be a substantially inextensible portion 3334 or a low extensibility portion 3338 as described above, for example.

During forming of the strap 3310 the various layers may be thermally compressed and bonded together. In some examples, the strap 3310 may be formed by thermoforming. For examples, the first outer layer 3338, the second outer layer 3338 and one or more support members 3320 may be thermoformed together. FIG. 17B shows an exemplary strap 3310 following the bonding step. After thermal compression the outer layers 3338 are bonded together, encapsulating the support member 3320 and webbing 3340. Advantageously, the outward surface of the strap 3310 on all sides is formed by a comfortable foam layer and textile skin of the outer layer 3338.

In some examples, each layer may include an adhesive backing to provide for locating and holding the layer during the forming process. In some examples, adhesives are not required if each layer thermally bonds to the others during the compression process. Alternatively, in some examples some inner layers or components (e.g. the support member 3320, webbing 3340, or other inner layer or component as the case may be) may not form a bond to the outer layers 3338 and may instead become encapsulated and mechanically restrained within the foam inner layers of the outer layers 3338.

These methods of construction advantageously provide for straps 3310 comprising rigidisers or other added layers or components which are built into the straps 3310 without being visible on the outer surfaces thereof.

4.3.3 Vent

It has already been described above that, in certain forms of the technology, the patient interface 3000 includes a vent 3400 constructed and arranged to allow for the washout of exhaled gases, e.g. carbon dioxide, from the plenum chamber 3200.

The vents 3400 described earlier in this specification are vents that are provided to the cushion module 6100, for example comprised as part of plenum chamber 3200. In other forms of the technology, the vent 3400 may be comprised as part of another part of patient interface 3000 or another part of the respiratory system with which patient interface 3000 operates in use. For example, the vent 3400 may be provided to the inlet conduit that supplies breathable gas to the plenum chamber 3200 through the plenum chamber supply port 3205. The vent 3400 may be provided to an elbow 4700 or other decoupling structure, e.g. swivel, configured to connect to the plenum chamber supply port 3205.

4.3.4 Decoupling Structure(s)

In certain forms the patient interface 3000 includes at least one decoupling structure, for example, a swivel or a ball and socket. The decoupling structure may, in some forms, take the form of an elbow, such as elbow 4700.

4.3.5 Connection Port

In certain forms, the patient interface comprises a connection port 3600, which allows for fluid connection to the air circuit 4170. The connection port 3600 may be a port on a downstream end of the inlet conduit or elbow 4700, with an upstream end connecting to the plenum chamber supply port 3205. In alternative forms, the connection port 3600 and plenum chamber supply port 3205 may be provided by the same opening in the plenum chamber 3200.

4.3.6 Forehead Support

In the illustrated forms of the technology, the patient interface 3000 does not include a forehead support, i.e. there is no component that, in use, is configured to rest against the patient's forehead in order to assist positioning and stabilising the seal-forming structure 3100 on the patient's face. The effect of the strap 3310 may provide sufficient positioning and stabilising for effective therapeutic use of the patient interface 3000. The lack of forehead support may mean that, when worn, the superior-most component of the patient interface 3000 is the superior end of the cushion module 6100 which, in some forms, is located over the nasal bridge region of the patient's face. Some patients may find a patient interface 3000 without a forehead support less intrusive and/or claustrophobic to wear.

In other forms of the technology, the patient interface 3000 may include a forehead support 3700, for example of the type shown in FIG. 3.

4.3.7 Anti-Asphyxia Valve

In certain forms, the patient interface 3000 includes an anti-asphyxia valve. An anti-asphyxia valve may function to provide an air path with ambient for the patient to breathe in the event that the RPT device 4000 ceases supplying breathable gas to the patient. An anti-asphyxia valve may particularly be provided in the case of a full-face mask.

4.3.8 Ports

In one form of the present technology, a patient interface 3000 includes one or more ports that allow access to the volume within the plenum chamber 3200. In one form this allows a clinician to supply supplementary oxygen. In one form, this allows for the direct measurement of a property of gases within the plenum chamber 3200, such as the pressure.

4.4 RPT Device

An RPT device 4000 in accordance with one aspect of the present technology comprises mechanical, pneumatic, and/or electrical components. The RPT device 4000 may be configured to generate a flow of air for delivery to a patient's airways, such as to treat one or more of the respiratory conditions described elsewhere in the present document.

4.5 Air Circuit

An air circuit 4170 in accordance with an aspect of the present technology is a conduit or a tube constructed and arranged to allow, in use, a flow of air to travel between two components such as RPT device 4000 and the patient interface 3000 or 3800.

In particular, the air circuit 4170 may be in fluid connection with the outlet of the RPT device 4000 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller of the RPT device 4000. One example of an air circuit 4170 comprising a heated wire circuit is described in U.S. Pat. No. 8,733,349, which is incorporated herewithin in its entirety by reference.

4.6 Humidifier

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

4.7 Glossary

For the purposes of the present technology disclosure, in certain forms of the present technology, one or more of the following definitions may apply. In other forms of the present technology, alternative definitions may apply.

4.7.1 General

Air: In certain forms of the present technology, air may be taken to mean atmospheric air, and in other forms of the present technology air may be taken to mean some other combination of breathable gases, e.g. oxygen enriched air.

Ambient: In certain forms of the present technology, the term ambient will be taken to mean (i) external of the treatment system or patient, and (ii) immediately surrounding the treatment system or patient.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

Flow therapy: Respiratory therapy comprising the delivery of a flow of air to an entrance to the airways at a controlled flow rate referred to as the treatment flow rate that is typically positive throughout the patient's breathing cycle.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Pressure: Force per unit area. Pressure may be expressed in a range of units, including $cmH_2O$, g-f/cm$^2$ and hectopascal. 1 $cmH_2O$ is equal to 1 g-f/cm$^2$ and is approximately 0.98 hectopascal (1 hectopascal=100 Pa=100 N/m$^2$=1 millibar~0.001 atm). In this specification, unless otherwise stated, pressure is given in units of $cmH_2O$.

Respiratory Pressure Therapy: The application of a supply of air to an entrance to the airways at a treatment pressure that is typically positive with respect to atmosphere.

Ventilator: A mechanical device that provides pressure support to a patient to perform some or all of the work of breathing.

4.7.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

4.7.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

- 'Soft' materials may include silicone or thermo-plastic elastomer (TPE), and may, e.g. readily deform under finger pressure.
- 'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions. The inverse of stiffness is flexibility.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 cmH2O pressure.

As an example, an I-beam may comprise a different bending stiffness (resistance to a bending load) in a first direction in comparison to a second, orthogonal direction. In another example, a structure or component may be floppy in a first direction and rigid in a second direction.

4.7.2 Anatomy 4.7.2.1 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius):

Lip, upper (labrale superius):

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion

4.7.2.2 Anatomy of the Skull

Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

4.7.3 Patient Interface

Anti-asphyxia valve (AAV): The component or sub-assembly of a mask system that, by opening to atmosphere in a failsafe manner, reduces the risk of excessive CO2 rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

4.7.4 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 4A to FIG. 4E, which illustrate examples of cross-sections at point p on a surface, and the resulting plane curves. FIGS. 4A to 4E also illustrate an outward normal vector at p. The outward normal vector at p points away from the surface. In some examples we describe the surface from the point of view of an imaginary small person standing upright on the surface.

4.7.4.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 4A (relatively large positive curvature compared to FIG. 4B) and FIG. 4B (relatively small positive curvature compared to FIG. 4A). Such curves are often referred to as concave.

Zero curvature: If the curve at p is a straight line, the curvature will be taken to be zero (if the imaginary small person leaves the point p, they can walk on a level, neither up nor down). See FIG. 4C.

Negative curvature: If the curve at p turns away from the outward normal, the curvature in that direction at that point will be taken to be negative (if the imaginary small person leaves the point p they must walk downhill). See FIG. 4D (relatively small negative curvature compared to FIG. 4E) and FIG. 4E (relatively large negative curvature compared to FIG. 4D). Such curves are often referred to as convex.

4.7.4.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 4A to 4E could be examples of such multiple cross-sections at a particular point.

4.8 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

4.9 Reference Signs List

1000 Patient
3000 Patient interface
3100 Seal-forming structure
3112 Superior portion
3114 Inferior portion
3110 Opening
3120 Sealing flange
3200 Plenum chamber
3205 Plenum chamber inlet port
3207 O-ring
3210 Flex region
3211 Chassis portion
3212 Superior portion
3214 Inferior portion
3220 Slit
3225 Gusset
3230 Recessed region
3300 Positioning and stabilising structure
3310 Strap
3312 First end
3314 Second end
3316 Cushion engaging portion
3318 Split
3320 Support members
3321 Peripheral support member
3322 Spanning support member portion
3324 Side support member portions
3326 Connection holes
3330 Opening
3332 Fastening portion
3334 Substantially inextensible portion
3336 Low extensibility portion
3338 Outer layer
3340 Webbing
3350 Elastic region
3352 Superior edge
3354 Inferior edge
3356 Recesses
3358 Elastic material
3400 Vent
3600 Connection port
3700 Forehead support
4000 RPT device
4170 Air circuit
4700 Elbow
5000 Humidifier
5002 Humidifier inlet
5004 Humidifier outlet
5006 Humidifier base
5110 Humidifier reservoir
5130 Humidifier reservoir dock
5240 Heating element
6100 Cushion module

The invention claimed is:

1. A patient interface for use in delivering breathable gas to a patient, the patient interface comprising:

a cushion module comprising a chassis portion and a seal-forming structure together forming a plenum chamber pressurisable to a therapeutic pressure of at least 4 $cmH_2O$ above ambient air pressure, the chassis portion having a width in a direction perpendicular to a sagittal plane of the patient when the patient interface is worn in use, and the chassis portion including a plenum chamber inlet port configured to receive a flow of breathable gas at the therapeutic pressure for breathing by the patient, the seal-forming structure being configured to form a seal with a region of the patient's face surrounding an entrance to the patient's airways, said seal-forming structure having an opening therein such that the flow of breathable gas is delivered to the entrance to the patient's airways, the seal-forming structure being configured to maintain said therapeutic pressure in the plenum chamber throughout the patient's respiratory cycle in use;

a vent structure to allow a continuous flow of gases exhaled by the patient from an interior of the plenum chamber to ambient, said vent structure being configured to maintain the therapeutic pressure in the plenum chamber in use; and a positioning and stabilising structure to provide a force to hold the seal-forming structure in a therapeutically effective position on the patient's head, the positioning and stabilising structure comprising:

a strap configured to be arranged, in use, so that an anterior portion of the strap positioned anteriorly to and overlies an anterior surface of the chassis portion across the width of the chassis portion to position the anterior surface of the chassis portion between the anterior portion of the strap and the patient's face, the strap passes around the sides of the patient's head inferior to the patient's ears, and a posterior portion of the strap overlies a posterior region of the patient's neck, wherein no part of the positioning and stabilising structure is configured to be positioned superior to the patient's ears in use, wherein the patient interface does not include a forehead support.

2. The patient interface of claim 1, wherein the strap comprises a first end and a second end and the strap is configured so that the first end is able to be secured to the second end so that the strap forms a loop.

3. The patient interface of claim 2, wherein the strap comprises a cushion engaging portion between the first end and the second end, and wherein the strap is arranged, in use, so that the anterior portion of the strap overlying the anterior surface of the chassis portion comprises the cushion engaging portion, and the posterior portion of the strap overlying the posterior region of the patient's neck comprises the first end and the second end.

4. The patient interface of claim 3, wherein the chassis portion has a height in a direction perpendicular to the Frankfort horizontal plane of the patient when the patient interface is worn in use, and a height of the strap in the cushion engaging portion being such that, in use, the strap covers a majority of the height of the chassis portion.

5. The patient interface of claim 1, wherein the anterior portion of the strap has an opening formed therein, the opening being configured to accommodate a conduit for conveying the flow of breathable gas to the plenum chamber inlet port.

6. The patient interface of claim 1, wherein the anterior portion of the strap has a curvature so that, in use, the anterior portion of the strap cups around the chassis portion.

7. The patient interface of claim 1, wherein the positioning and stabilising structure comprises one or more support members provided to the anterior portion of the strap, the support members being rigid or semi-rigid and being configured to provide or substantially maintain the curvature of the anterior portion of the strap when the anterior portion of the strap under tension.

8. The patient interface of claim 7, wherein the one or more support members are provided to a side of the anterior portion of the strap configured to face towards the patient in use.

9. The patient interface of claim 7, wherein at least one of the one or more support members is arranged to span across a length of the anterior portion of the strap.

10. The patient interface of claim 7, wherein the one or more support members comprise a first support member portion and a second support member portion, each of the first support member portion and second support member portion is positioned so that, in use, the first support member portion contacts a first lateral side of the chassis portion and the second support member portion contacts a second lateral side of the chassis portion, the first lateral side of the chassis portion being opposite the second lateral side of the chassis portion.

11. The patient interface of claim 1, wherein the strap comprises a first elastic region in a region of the strap that, in use, is positioned between the anterior portion of the strap and the posterior portion of the strap on a first lateral side of the patient's head, and a second elastic region in a region of the strap that, in use, is positioned between the anterior portion of the strap and the posterior portion of the strap on a second lateral side of the patient's head, the first lateral side of the patient's head being opposite the second lateral side of the patient's head, and wherein the strap comprises a first substantially inextensible portion positioned between the anterior portion of the strap and the posterior portion of the strap on the first lateral side of the patient's head in use, and a second substantially inextensible portion positioned between the anterior portion of the strap and the posterior portion of the strap on the second lateral side of the patient's head in use.

12. The patient interface of claim 11, wherein the first elastic region and the second elastic region are provided along an edge of the strap.

13. The patient interface of claim 11, wherein the strap comprises a pair of low extensibility portions located on respective lateral sides of the strap, the low extensibility portions being more extendable than the first substantially inextensible portion and the second substantially inextensible portion but less extendable than the first elastic region and the second elastic region.

14. The patient interface of claim 13, wherein the strap comprises a first end and a second end and the strap is configured so that the first end is able to be secured to the second end so that the strap forms a loop, wherein the strap comprises a cushion engaging portion between the first end and the second end, and wherein the strap is arranged, in use, so that the anterior portion of the strap overlying the anterior surface of the chassis portion comprises the cushion engaging portion, and the posterior portion of the strap overlying the posterior region of the patient's neck comprises the first end and the second end, and wherein each of the low extensibility portions extends from a respective end of the strap along the strap approximately halfway to a respective lateral edge of the cushion engaging portion.

15. The patient interface of claim 1, wherein the chassis portion is flexible.

16. The patient interface of claim 1, wherein the chassis portion comprises a flex region having greater flexibility than other regions of the chassis portion, the flex region being configured to enable a superior portion of the chassis portion to move relative to an inferior portion of the cushion module.

17. The patient interface of claim 16, wherein the flex region extends across substantially the width of the chassis portion.

18. The patient interface of claim 1, wherein the vent structure is in the anterior surface of the chassis portion and the strap comprises a gas permeable portion, the strap being configured so that, in use, the gas permeable portion overlies the vent structure so that the continuous flow of gases exhaled by the patient passes through the gas permeable portion.

19. A patient interface for use in delivering breathable gas to a patient, the patient interface comprising:

a cushion module comprising a plenum chamber and a seal-forming structure, the plenum chamber pressurisable to a therapeutic pressure of at least 4 $cmH_2O$ above ambient air pressure and the plenum chamber including a plenum chamber inlet port configured to receive a flow of breathable gas at the therapeutic pressure for breathing by the patient, the seal-forming structure being configured to form a seal with a region of the patient's face surrounding an entrance to the patient's airways, said seal-forming structure having an opening therein such that the flow of breathable gas is delivered to the entrance to the patient's airways, the seal-forming structure being configured to maintain said therapeutic pressure in the plenum chamber throughout the patient's respiratory cycle in use;

a vent structure to allow a continuous flow of gases exhaled by the patient from an interior of the plenum chamber to ambient, said vent structure being configured to maintain the therapeutic pressure in the plenum chamber in use; and a positioning and stabilising structure to provide a force to hold the seal-forming structure in a therapeutically effective position on the patient's head, the positioning and stabilising structure comprising:

a strap comprising an anterior portion positioned anteriorly to and structured to overlie an anterior surface of the cushion module to position the anterior surface of the cushion module between the anterior portion of the strap and the patient's face, and a posterior portion structured to overlie a posterior region of the patient's neck;

wherein the strap is structured and arranged to maintain the seal-forming structure in the therapeutically effective position when the plenum chamber is pressurised to a therapeutic pressure in the absence of other straps, wherein the patient interface does not include a component that, in use, is configured to rest against the patient's forehead in order to assist positioning and stabilising the seal-forming structure on the patient's face.

20. The patient interface of claim 19, wherein the strap comprises a first end and a second end, wherein the first end is attachable to the second end so that the strap forms a loop, and the strap comprises a cushion engaging portion mid-way between the first end and the second end.

21. The patient interface of claim 20, wherein the cushion module has a height in a direction perpendicular to the Frankfort horizontal plane of the patient when the patient interface is worn in use, and a height of the strap in the cushion engaging portion is such that the strap is structured and arranged to cover a majority of the height of the cushion module in use.

22. The patient interface of claim 19, wherein the anterior portion of the strap has a curvature structured to cup around the cushion module.

23. The patient interface of claim 19, wherein the positioning and stabilising structure comprises one or more support members provided to the anterior portion of the strap.

24. The patient interface of claim 23, wherein the one or more support members may be configured to provide or substantially maintain a curvature of the anterior portion of the strap when the anterior portion of the strap under tension.

25. The patient interface of claim 19, wherein the strap comprises a first elastic region positioned between the anterior portion of the strap and the posterior portion of the strap on a first lateral side of the patient's head in use, and a second elastic region positioned between the anterior portion of the strap and the posterior portion of the strap on a second lateral side of the patient's head in use.

26. The patient interface of claim 25, wherein the strap comprises a first substantially inextensible portion positioned between the anterior portion of the strap and the posterior portion of the strap on the first lateral side of the patient's head in use, and a second substantially inextensible portion positioned between the anterior portion of the strap and the posterior portion of the strap on the second lateral side of the patient's head in use.

27. The patient interface of claim 26, wherein the strap comprises a pair of low extensibility portions located on respective lateral sides of the strap, the low extensibility portions being more extendable than the first substantially inextensible portion and the second substantially inextensible portion but less extendable than the first elastic region and the second elastic region.

28. The patient interface of claim 27, wherein the strap comprises a first end and a second end, wherein the first end is attachable to the second end so that the strap forms a loop, and the strap comprises a cushion engaging portion mid-way between the first end and the second end, wherein each of the low extensibility portions extends from a respective end of the strap along the strap approximately halfway to a respective lateral edge of the cushion engaging portion.

29. The patient interface of claim 26, wherein the first elastic region and the second elastic region are provided adjacent one of a superior edge and an inferior edge of the strap and the first substantially inextensible portion and the second substantially inextensible portion are provided adjacent the other of the superior edge and the inferior edge of the strap.

30. The patient interface of claim 19, wherein the cushion module comprises a chassis portion, the chassis portion and the seal-forming structure at least partly forming the plenum chamber, wherein the chassis portion comprises a flex region having greater flexibility than other regions of the chassis portion, the flex region being configured to enable a superior portion of the chassis portion to move relative to an inferior portion of the cushion module.

31. The patient interface of claim 30, wherein the flex region extends across substantially the width of the chassis portion.

* * * * *